US007611854B2

(12) United States Patent
Fowlkes et al.

(10) Patent No.: US 7,611,854 B2
(45) Date of Patent: Nov. 3, 2009

(54) YEAST CELLS ENGINEERED TO PRODUCE PHEROMONE SYSTEM PROTEIN SURROGATES, AND USES THEREFOR

(75) Inventors: Dana M. Fowlkes, Chapel Hill, NC (US); Jim Broach, Princeton, NJ (US); John Manfredi, Ossining, NY (US); Christine Klein, Ossining, NY (US); Andrew J. Murphy, Montclair, NJ (US); Jeremy Paul, South Nyack, NY (US); Joshua Trueheart, South Nyack, NY (US)

(73) Assignee: Cadus Technologies, Inc., New York, NY (US)

( * ) Notice: Subject to any disclaimer, the term of this patent is extended or adjusted under 35 U.S.C. 154(b) by 1909 days.

(21) Appl. No.: 10/600,003

(22) Filed: Jun. 18, 2003

(65) Prior Publication Data

US 2004/0197840 A1 Oct. 7, 2004

Related U.S. Application Data

(63) Continuation of application No. 09/286,166, filed on Apr. 5, 1999, now Pat. No. 7,416,881, which is a continuation-in-part of application No. 08/322,137, filed on Oct. 13, 1994, now Pat. No. 6,100,042, which is a continuation-in-part of application No. 08/309,313, filed on Sep. 20, 1994, now abandoned, which is a continuation-in-part of application No. 08/190,328, filed on Jan. 31, 1994, now abandoned, which is a continuation-in-part of application No. 08/041,431, filed on Mar. 31, 1993, now abandoned.

(51) Int. Cl.
*C12N 1/19* (2006.01)
*G01N 33/53* (2006.01)
(52) U.S. Cl. .................................. 435/7.31; 435/254.2
(58) Field of Classification Search ........................ None
See application file for complete search history.

(56) References Cited

U.S. PATENT DOCUMENTS

| 5,096,815 | A | 3/1992 | Ladner et al. |
| 5,283,173 | A | 2/1994 | Fields et al. |
| 5,284,746 | A | 2/1994 | Sledziewski et al. |
| 5,468,614 | A | 11/1995 | Fields et al. |
| 5,580,736 | A | 12/1996 | Brent et al. |
| 5,691,188 | A | 11/1997 | Pausch et al. |
| 6,100,042 | A | 8/2000 | Fowlkes et al. |

FOREIGN PATENT DOCUMENTS

| WO | WO-8810308 | 12/1988 |
| WO | WO-9112273 | 8/1991 |
| WO | WO-9205244 | 4/1992 |
| WO | WO-9530012 | 11/1995 |
| WO | WO-9711159 | 3/1997 |
| WO | WO-9813513 | 4/1998 |

OTHER PUBLICATIONS

Dohlman-HG, Annu. Rev. Biochem. 60(653-88)1991.*
Kaziro-Y et al, Annu. Rev. Biochem. 60(349-400)1991.*
Stevenson-BJ et al., Genes Dev. 6(1293-304)1992.*
Artemyev et al., "Sites of Interaction between Rod G-Protein a -Subunit and cGMP-Phosphodiesterase Gamma-Subunit," *The Journal of Biological Chemistry*, vol. 267(35). pp. 25067-25072 (1992).
Awramik et al., "New Fossil find in Old Rocks," *Nature*, vol. 319, pp. 446-447 (1986).
Bender et al., Pheromones and Pheromone Receptors are the Primary Determinants of Mating Specificity in the Yeast Saccharomyces Cerevisiae, *Genetics*, vol. 121, pp. 463-476 (1989).
Cavallini et al., A Yeast Activity can Substitute for the HeLa Cell TATA box factor, *Nature*, vol. 334, pp. 77-80 (I1988).
Chan et al., "Isolation and Genetic Analyusis of Saccharomyces Cerevisiae Mutants Supersensitive to G1 Arrest by a Factor and a Factor," *Molecular and Cellular Biology*, vol. 13(1), pp. 1-8 (1993).
Chang et al., "Identification of a Gene Necessary for Cell Cycle Arrest by a Negative Growth Factor of Yeast: FAR1 is an inhibitor of a G1 Cyclin, CLN2," *Cell*, vol. 63, pp. 999-1011 (1990).
Clark et al., "Interactions Among the Subunits of the G-Protein Involved in Saccharomyces Cerevisiae Mating," *Molecular and Cellular biology*, vol. 13(1), pp. 1-8 (1993).
Coleman et al., "Structures of Active Conformation of G-ia1 and the Mechanism of GTP Hydrolysis," *Science*, vol. 265, pp. 1405-1412 (1994).
Conklin et al., "Substitution of Three Amino Acids Switches Receptor Specificity of G-qa to that of G-ia," *Nature*, 363, pp. 274-276 (1993).
Dietzel et al., "The Yeast SCG1 Gene: a Ga-like Protein Implicated in the a- and a-Factor Dietzel Response Pathway," *Cell*, vol. 50, pp. 1001-1010 (1987).
Dmochowska et al., "Yeast KEX1 Gene Encodes a Putative Protease with a Carboxypeptidase B-like Function Involved in Killer Toxin and a-Factor Precursor Processing," *Cell*, vol. 50, pp. 573-584 (1987).
Etienne et al., "A Screening Method for Antifungal Substances using Saccharomyces Cerevisiae Strains Resistant to Polyene Macrolides," *The Journal of Antibiotics*, vol. XLIII(2), pp. 199-206 (1990).
Fasullo et al., "Direction of Chromosome Rearrangements in Saccharomyces Cerevisiae by use of his3 Recombination Substrates," *Molecular and Cellular Biology*, vol. 8(10, pp. 4370- 4380 (1988).
Franke et al., "Human C5a Anaphylatoxin: Gene Synthesis, Expression, and REcovery of Biologically Active Material from *Escherichia coli*, "*Methods in Enzymology*, vol. 162, pp. 653- 668 (1988).

(Continued)

*Primary Examiner*—John D Ulm
(74) *Attorney, Agent, or Firm*—Edwards Angell Palmer & Dodge LLP; Peter C. Lauro, Esq.; Melissa Hunter-Ensor, Esq.

(57) ABSTRACT

Yeast cells are engineered to express both a surrogate of a pheromone system protein (e.g., enzymes involved in maturation of α-factor, transporters of a-factor, pheromone receptors, etc.) and a potential peptide modulator of the surrogate, in such a manner that the inhibition or activation of the surrogate affects a screenable or selectable trait of the yeast cells. Various additional features improve the signal-to-noise ratio of the screening/selection system.

10 Claims, 11 Drawing Sheets

OTHER PUBLICATIONS

Gallego et al., "Myristoylation of the Gai2 Polypeptide, a G Protein a Subunit, is Required for its Signaling and Transformation Functions," *Proc. Natl. Acad. Sci . USA*, vol. 89, pp. 9695-9699 (1992 ).

Garritsen et al., "The N-Terminal Coiled-Coil Domain of B is Essential for Gamma Association: A Model for G-Protein B-Gamma Subunit Interaction, "*Proc Natl. Acad. Sci. USA*, vol. 90, pp. 7706-7710 (1993).

Gerard et al., "Construction and Expression of a Novel Recombinant Anaphylatoxin, C5a-N19, a Probe for the Human C5a Receptor," *Biochemistry*, vol. 29(39), pp. 9274-9281 (1990).

Graf et al., "A Truncated Recombinant a Subunit of G-i13 with a Reduced Affinity for B-Gamma Dimers and Altered Guanosine 5'-3-O-(Thio) Triphosphate Binding," *The Journal of Biological Chemistry*, vol. 267(34), pp. 24307-24314(1986).

Gros et al., "Mammalian Multidrug Resistance Gene: Complete cDNA Sequence Indicates Strong Homology to Bacterial Transport Proteins," *Cell*, vol. 47, pp. 371-380 (1986).

Hagen et al., Evidence the Yeast STE3 Gene Encodes a Receptor for the Peptide Pheromone a Factor: Gene Sequence and Implications for the Structure of the Presumed Receptor, *Proc. Natl. Acad. Sci, USA*, vol. 83, pp. 1418-1422 (1986).

Harbury et al., "A Switch Between Two-, Three- and Four- Stranded Coiled Coils in GCN4 Leucine Zipper Mutants," *Science*, vol. 262, pp. 1401-1407 (1993).

Hartwell, "Mutants of Saccharomyces Cervisiae Unresponsive to Cell Division Control by Polypeptide Mating Hormone," *J. Cell Biology*, vol. 85, pp. 811-822 (1980).

He et al., "RAM2, an Essential Gene of Yeast, and RAM1 Encode the Two Polypeptide Components of the Farnesyltransferase that Prenylates a-Factor and Ras proteins," *Proc. Natl. Acad. Sci. USA*, vol. 88, pp. 11373-11377 (1991).

Hrycyna et al., The Saccharomyces Cerevisiae STE14 Gene Encodes a Methyltransferase the Mediates C-Terminal Methylation of a-Factor nd RAS Proteins, *The Embo Journal*, vol. 10(7), pp. 1699-1709 (1991).

Jabbar et al., "Influenza Viral (A/WSN/33) Hemagglutinin is Expressed and Glyosylated in the Yeast Saccharomyces Cerevisiae," *Proc. Natl. Acad. Sci USA*, vol. 82, pp. 2019-2023 (1985).

Journot et al., "Amino Acids 367-376 of the Gs a Subunit Induce Membrane Association when Fused to Soluble Amino-Terminal Deleted Gil a subunit," *Proc. Natl. Acad. Aci. USA*, vol. 88, pp. 10054-10058 (1991).

Julius et al., "Glycosylation and Processing of Prepro-a-Factor through the Yeast Secretory Pathway," *Cell*, vol. 36, pp. 309-318 (1984).

Julius et al., "Isolation of the Putative Structural Gene for the Lysine-Arginine-Cleaving Endopeptidase Required for Processing of Yeast Prepro-a-Factor," *Cell*, vol. 37, pp. 1075-1089 (1984).

Julius et al., "Yeast a factor is Processed from a Larger Precursor Plypeptide: The Essential Role of a Membrane-Bound Dipeptidyl Aminopeptidase," *Cell*, vol. 32, pp. 839-852 (1983).

Kaiser et al., "Many Random Sequences Functionally Replace the Secretion Signal Sequence of Yeast Invertase," *Science*, vol. 235, pp. 312-317 (1987).

Kingsman et al., "The Production of Mammalian Protein in Saccharomyces Cerevisiae," *Tibtech*, vol. 5, pp. 53-57 (1987).

Kramer et al., "HTLV-III gag Protein is Processed in Yeast Cells by the Virus pol-Protease," *Science*, vol. 231, pp. 1580-1585 (1986).

Kuchler et al., "Functional Expression of Human mdr1 in the Yeast Saccharomyces Cerevisiae," *Proc. Natl. Acad. Sci. USA*, vol. 89, pp. 2302-2306 (1992).

Kuchler et al., "Saccharomyces Cerevisiae STE6 Gene Product: A Novel Pathway for Protein Export in Eukaryotic Cells," *The Embo Journal*, vol. 8(13), pp. 3973-3984 (1989).

Kurjan, "a-Factor Structural Gene Mutations in Saccharomyces Cerevisiae: Effects on a-Factor Production and Mating," *Molecular and Cellular Biology*, vol. 5(4), pp. 787-796 (1985).

Kurjan et al., "Structure of Yeast Pheromone Gene (MFa): A Putative a-Factor Precursor Contains Four Tandem Copies of Mature a-Factor," *Cell*, vol. 30, pp. 933-943 (1982).

Lambright et al., "Structural Determinants for Activation of the a-Subunit of a Heterotrimeric G Protein," *Nature*, vol. 369, pp. 621-628 (1994).

Leberer et al., "Dominant-Negative Mutants of a Yeast G-Protein B Subunit Identify tow Functional Regions Involved in Pheromone Signaling," *The Embo Journal*, vol. 11(13), pp. 4805-4813 (1992).

Lee et al., "The G22A Mutant of Gsa Highlights the Requirement for Dissociation of G Protein Subunits," *The Journal of Biological Chemistry*, vol. 267(2), pp. 1212-1218 (1992).

Lemire et al., The Mitochondrial Targeting Function of Randomly Generated Peptide Sequences Correlates with Predicted Helical Amphiphilicity, *The Journal of Biological Chemistry*, vol. 264(34), pp. 20206-20212 (1989).

Linder et al.,"Lipid Modifications of G Protein Subunits," *The Journal of Biological Chemistry*, vol. 266(7), pp. 4654-4659 (1991).

Lupas et al., "Do G Protein Subunits Associate via a Three-Stranded Coiled Coil?" *FEBS*, vol. 314(2), pp. 105-108 (1992).

Mackay et al., "Mutations Affecting Sexual Conjugation and Related Processes in Saccharomyces Cerevisiae. II. Genetic Analysis of Nonmating Mutants," *Genetics*, vol. 76, pp. 273-288 (1974).

Markby et al., "Separate GTP Binding and GTPase Activiating Domains of a Ga Subunit," *Science*, vol. 262, pp. 1895-1901 (1993).

Michaelis et al., " The a-Factor Pheromone of Saccharomyces Cerevisiae is Essential for Mating," *Molecular and Cellular Biology*, vol. 8(3), pp. 1309-1318 (1988).

Milano et al., " Enhanced Myocardial Function in Transgenic Mice Overexpressing the B2-Adrenergic Receptor," *Science*, vol. 264, pp. 582-586 (1994).

Mumby et al., "G-Protein a-subunit Expression, Myristoylation, and Membrane Association in COS Cells," *Proc. Natl. Acad. Sci. USA*, vol. 87, pp. 728-732 (1990).

Nakafuku et al., "Occurrence in Saccharomyces Cerevisiae of a Gene Homologous to the cDNA Coding for the a-subunit of Mammalian G Proteins," *Proc. NatL Acad. Sci. USA*, vol. 84, pp. 2140-2144 (1987).

Nakayama et al., "Common Signal Transduction System Shared by STE2 and STE3 in Haploid Cells of Saccharomyces Cerevisiae: Autocrine Cell-Cycle Arrest Results from Forced Expression of STE2," *The Embo Journal*, vol. 6(1), pp. 249-254 (1987).

Neer et al., "The Amino Terminus of a G Protein a Subunits is Required for Interaction with Beta-Gamma," *The Journal of Biological Chemistry*, vol. 263(18), pp. 8996-9000 (1988).

Noel et al., "The 2.2 A Crystal Structure of Transducin-a Complexed with GTP-Gamma-S," *Nature*, vol. 366, pp. 654-663 (1993).

Oeda et al., "Expression of Rat Liver Cytochrome p-450MC cDNA in Saccharomyces Cerevisiae," *DNA*, vol. 4(3), pp. 201-203 (1985).

Ogden et al., "Efficient Expression of the Saccharomyces Cerevisiae PGK Gene Depends on an Upstream Activation Sequence but does not require TATA Sequences," *Molecular and Cellular Biology*, vol. 6(12), pp. 4335-4343 (1986).

Pronin et al., "Interaction Between G-Protein B and Gamma Subunit Types is Selective," *Proc. Natl. Acad. Sci. USA*, vol. 89, pp. 6220-6224 (1992).

Rarick et al., "A Site on Rod G Protein a Subunit that Mediates Effector Activation," *Science*, vol. 256, pp. 1031-1033 (1992).

Schafer et al., "Enzymatic Coupling of Cholesterol Intermediates to a Mating Pheromone Precursor and to the Ras Protein," *Science*, vol. 249, pp. 1133-1139 (1990).

Schafer et al., "Genetic and Pharmacological Suppression of Oncogenic Mutations in RAS Genes of Yeast and Humans," *Science*, vol. 245, pp. 379-385 (1989).

Scharer et al., "Mammalian p53 can Function as a Transcription Factor in Yeast," *Nucleic Acids Research*, vol. 20(7), pp. 1539-1545 (1992).

Sikorski et al., "A System of Shuttle Vectors and Yeast Host Strains Designed for Efficient Manipulation of DNA in Saccharomyces Cerevisiae," *Genetics*, vol. 122, pp. 19-27 (1989).

Singh et al., "Saccharomyces Cerevisiae Contains two Discrete Genes Coding for the a-Factor Pheromone," *Nucleic Acids Research*, vol. 11(12), pp. 4049-4063 (1983).

Slepak et al., "Mutational Analysis of G Protein a Subunit GOa Expressed in *Escherichia Coli*," *The Journal of Biological Chemistry*, Vol. 268(2), pp. 1414-1423 (1993).

Spiegel et al., "The G Protein Connection Molecular Basis of Membrane Association," *TIBS*, vol. 16, pp. 338-341 (1991).

Steube et al., "a-Factor-Leader-Directed Secretion of Recombinant Human-Insulin-like Growth Factor I from Saccharomyces Cerevisiae," *Eur. J. Biochem.*, vol. 198, pp. 651-657 (1991).

Stevenson et al., "Constitutive Mutants of the Protein STE11 Activate the Yeast Pheromone Response Pathway in the Absence of the G Protein," *Genes & Development*, vol. 6, pp. 1293-1304 (1992).

Strubin et al., "Yeast and Human TFIID with Altered DNA-Binding Specificity of TATA Elements," *Cell*, vol. 68, pp. 721-730 (1992).

Struhl, "Constitutive and Inducible Saccharomyces Cerevisiae Promoters: Evidence of Two Distinct Molecular Mechanisms," *Molecular and Cellular Biology*, vol. 6(11), pp. 3847-3853 (1986).

Struhl et al., "High-Frequency Transformation of Yeast: Autonomous Replication of Hybrid DNA Molecules," *Proc. NatL Acad. Sci. USA*, vol. 76(3), pp. 1035-1039 (1979).

Struhl et al., "Two Related Regulatory Sequences are Required for Maximal Induction of Saccharomyces Cerevisiae his3 Transcription," *Molecular and Cellular Biology*, vol. 7(1), pp. 104-110(1987).

Sullivan et al., "Identification of Receptor Contact Site Involved in Receptor-G Protein Coupling," *Nature*, vol. 330, pp. 758-760 (1987).

Teem et al., "Identification of Revertants for the Cystic Fibrosis F508 Mutation using STE6- CFTR Chimeras in Yeast," *Cell*, vol. 73, pp. 335-345 (1993).

Thomas et al., "G-Protein ao Subunit: Mutation of Conserved Cysteines Identifies a Subunit Contact Surface and Alters GDP Affinity," *Proc. NatL Acad. Sci. USA*, vol. 90, pp. 10295-10299 (1993).

Walker et al., "Distantly Related Sequences in the a-and-B-subunits of ATP Synthase, Myosin, Kinases and Other ATP-requiring Enzymes and a Common Nucleotide Binding Fold," *The Embo Journal*, vol. 1(8), pp. 945-951 (1982).

Waters et al., "Prepro-a-Factor has a Cleavable Signal Sequence," *The Journal of Bilogical Chemistry*, vol. 263(13), pp. 6209-6214 (1988).

Whiteway et al., "Genetic Identification of Residues Involved in Association of a and B G-Protein Subunits," *Molecular and Cellular Biology*, vol. 14(5), pp. 3223-3229 (1994).

Stedman's Medical Dictionary 27th Edition, 2000, Lippincott Williams and Wilkins, entry: Heterologous (definition, p. 817).

Kang et al., "Effects of Expression of Mammalian Gα and Hybrid Mammalian-Yeast Gα Proteins on the Yeast Pheromone Response Signal Transduction Pathway," *Moleculat and Cellular Biology*, vol. 10(6), pp. 2582-250 (1990).

Manfredi et al., "Autocrine Stimulation of Yeast Through Human G-coupled Receptors," *J. Cell. Biochem.*, vol. 18B, pp. 224 (1994).

King et al., "Control of Yeast Mating Signal Transduction by a Mammalian beta2-Adrenergic Receptor and Gs Alpha Subunit," *Science*, vol. 250, pp. 121-123 (1990).

Cwirla et al., "Peptides on Phage: A Vast Library of Peptides for Identifying Ligands," *Prov. NatL Acad. Sci. USA*, vol. 87, pp. 6378-6382 (1990).

Devlin et al., "Random Peptide Libraries: A Source of Specific Protein Binding Molecules," *Science*, vol. 249, pp. 404-406 (1990).

Lew et al., "Isolation of Three Novel Human Cyclins by Rescue of G1 Cyclin (Cln) Function in Yeast," *Cell*, vol. 66, pp. 1197-1206 (1991).

Scott et al., "Searching for Peptide Ligands with an Epitope Library," *Science*, vol. 249, pp. 386-390 (1990).

Pausch, *TIBTECH*, vol. 15, pp. 487-494 (1997).

\* cited by examiner

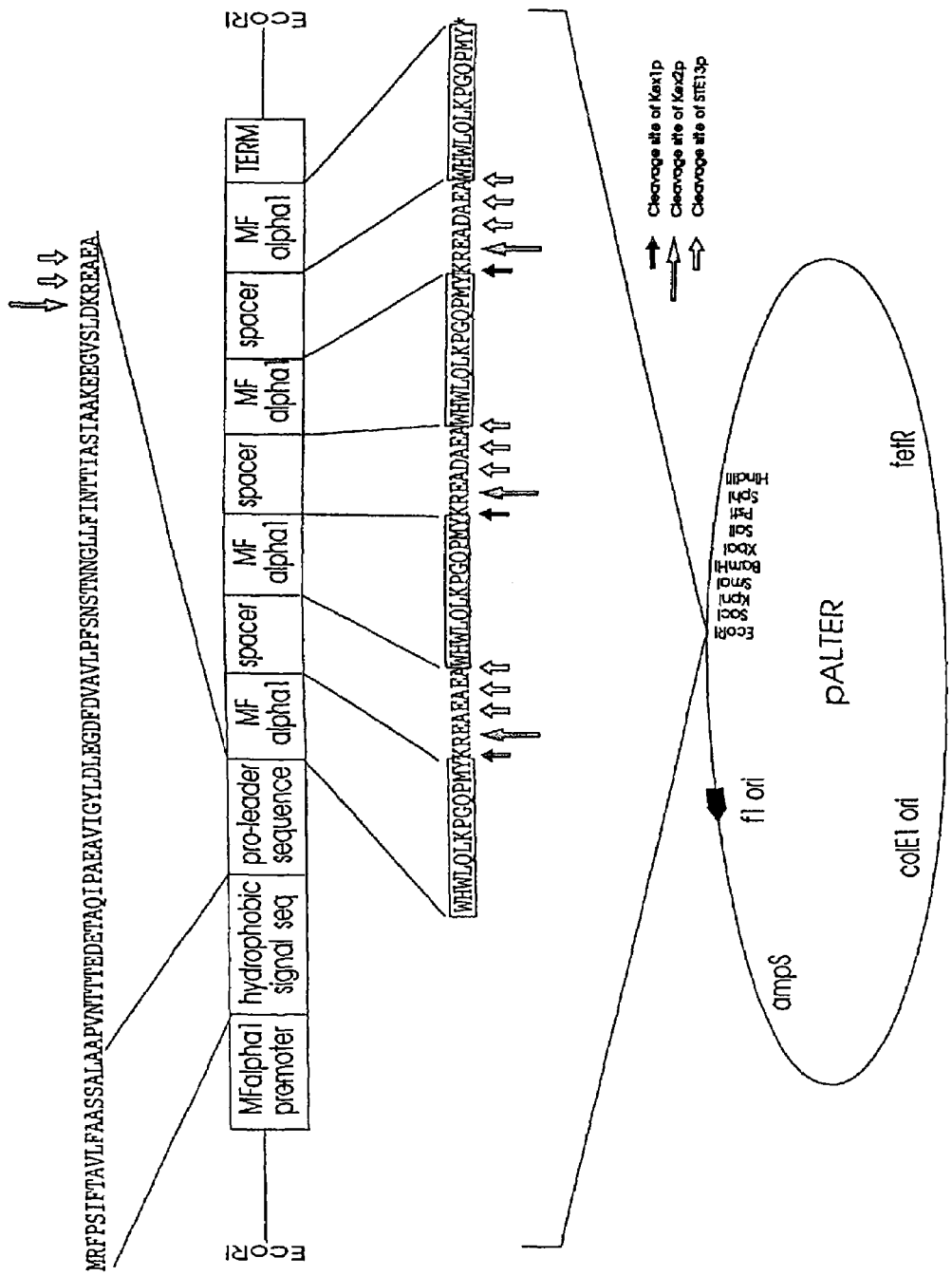
Figure 2. Schematic diagram to illustrate: 1. the structure of MFalpha1; 2. the amino acid sequence of the MFalpha1 coding region; 3. the sites of proteolytic processing of the precursor; 4. orientation of the EcoRI fragment in pALTER.

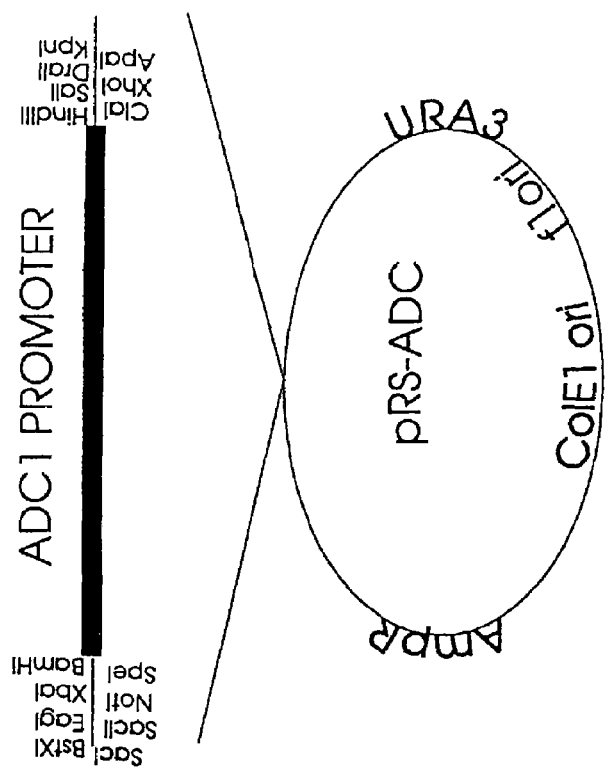
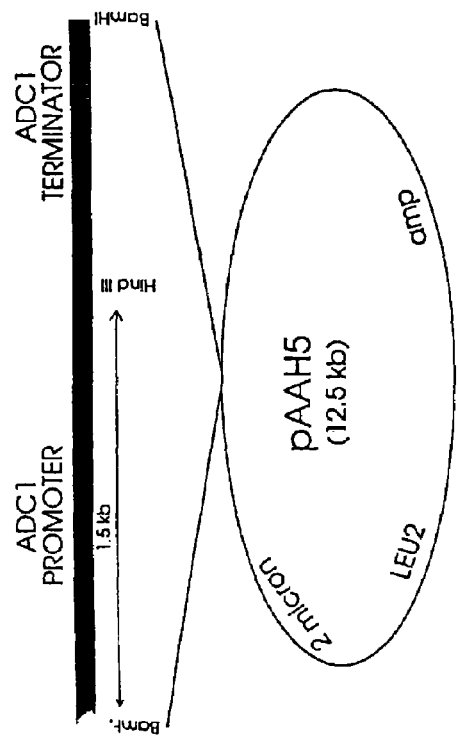
Figure 3. Structures of pAAH5 and pRS-ADC.

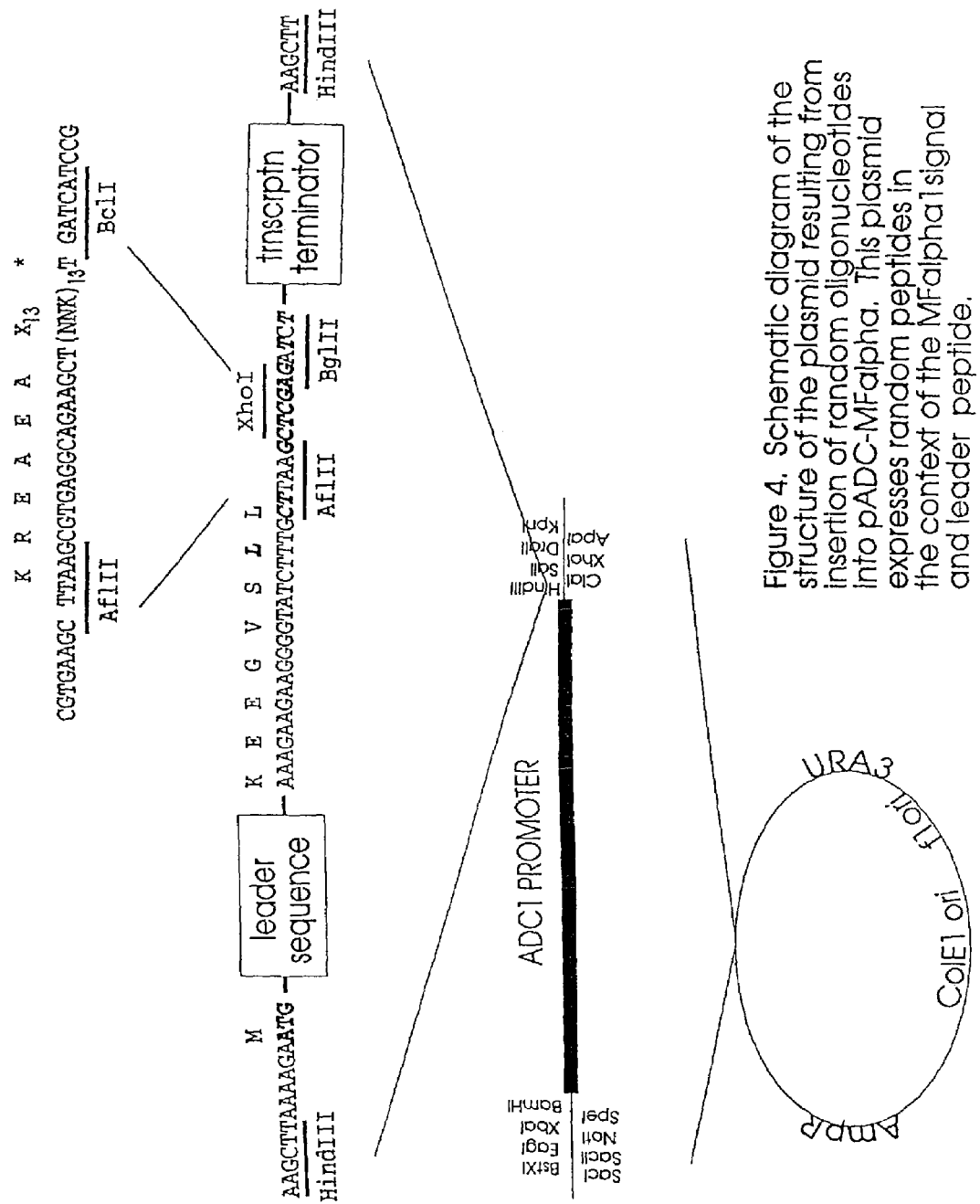
Figure 4. Schematic diagram of the structure of the plasmid resulting from insertion of random oligonucleotides into pADC-MFalpha. This plasmid expresses random peptides in the context of the MFalpha1 signal and leader peptide.

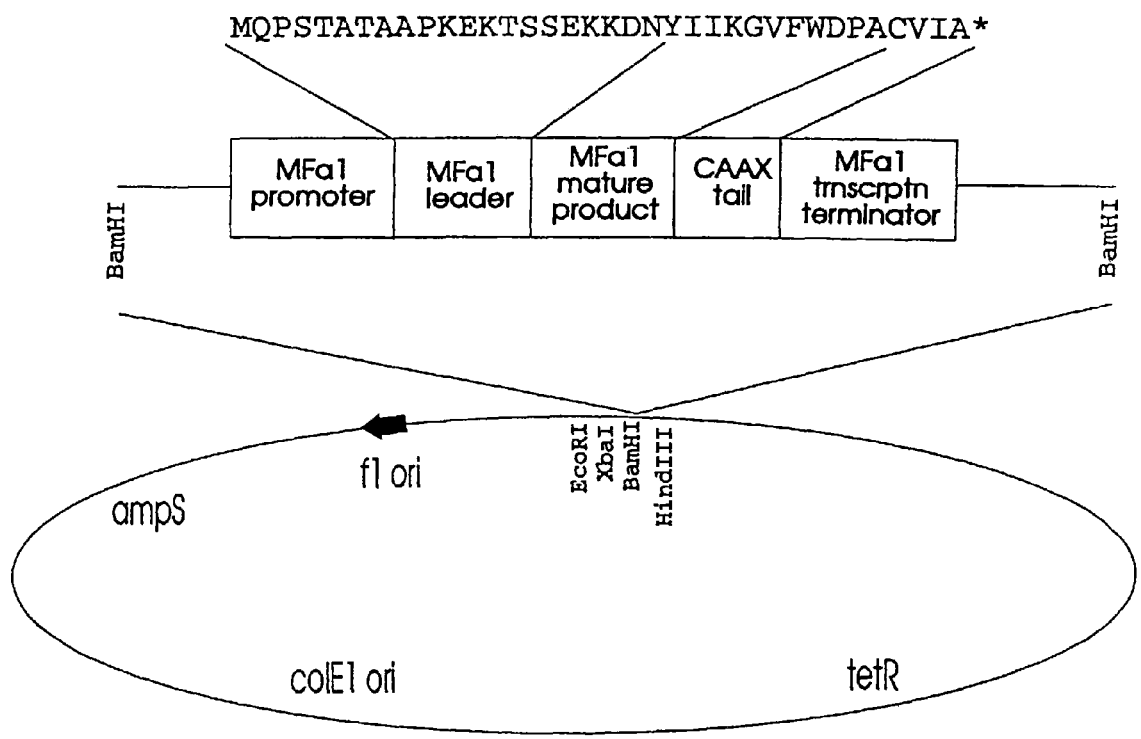
Figure 5. Schematic to illustrate: 1. the organization of MFa1;
2. the amino acid sequence of the MFa1 coding region;
3. the point of insertion of the fragment in pALTER.

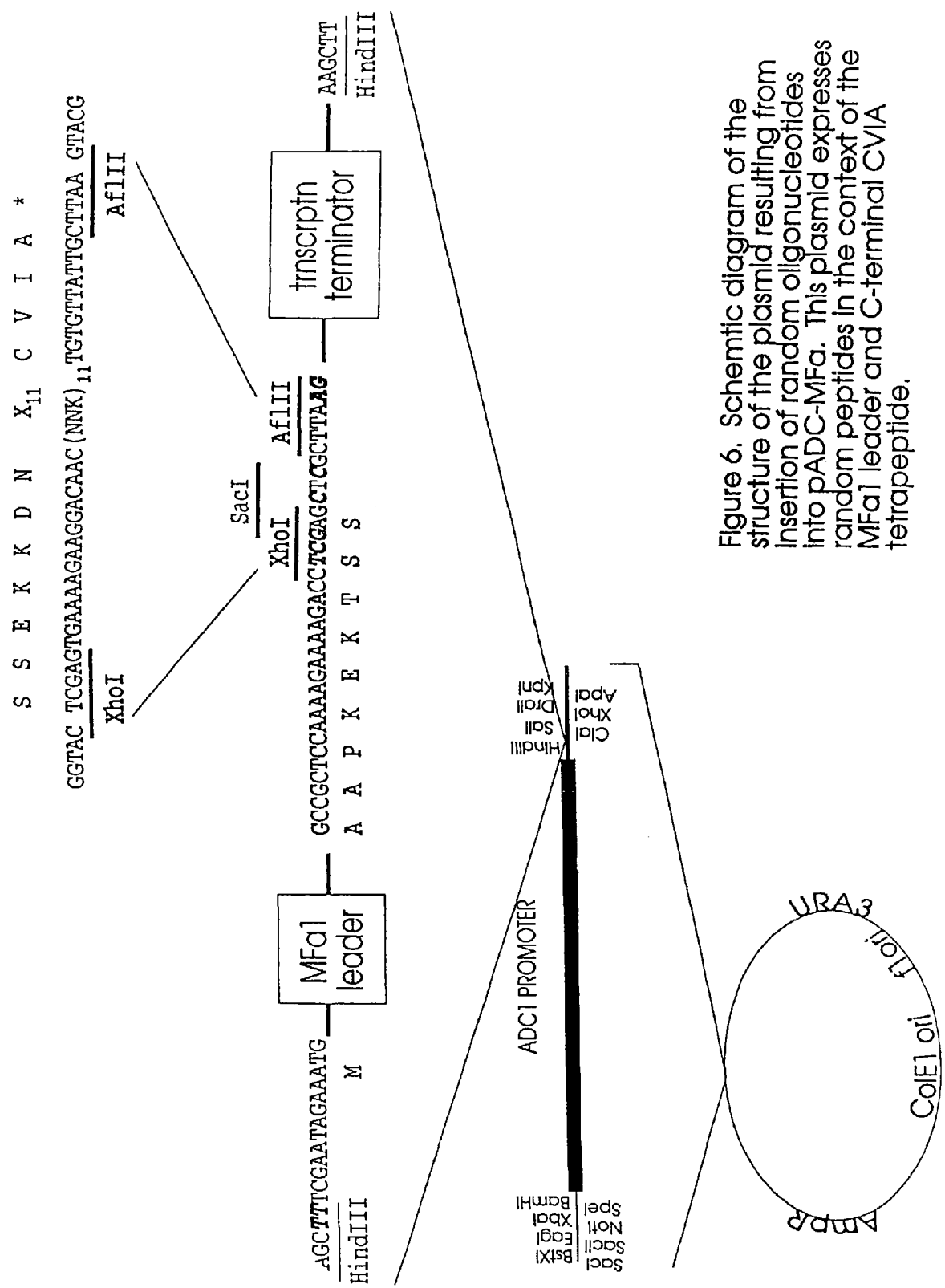
Figure 6. Schematic diagram of the structure of the plasmid resulting from insertion of random oligonucleotides into pADC-MFα. This plasmid expresses random peptides in the context of the MFα1 leader and C-terminal CVIA tetrapeptide.

Autocrine Mata Strain Secretes and Responds to Signalling by alpha-Factor

Autocrine MATa Strain Secretes and Responds to Signalling by a-Factor

Figure 9. pYMA177 containing human MDR1 mutant (G185V mutation)

Activity of a fus1 promoter in response to signalling by human C5a expressed in autocrine strains of yeast.

Gα switch region hybrids.

YEAST CELLS ENGINEERED TO PRODUCE PHEROMONE SYSTEM PROTEIN SURROGATES, AND USES THEREFOR

This is a continuation of application Ser. No. 09/286,166, filed Apr. 5, 1999 now U.S. Pat. No. 6,100,042, which is a continuation-in-part of Ser. No. 08/322,137, filed Oct. 13, 1994, now U.S. Pat. No. 7,416,881 which is a continuation-in-part of Ser. No. 08/309,313, filed Sep. 20, 1994, (abandoned), which is a continuation-in-part of Ser. No. 08/190,328, filed Jan. 31, 1994, now abandoned, which is a continuation-part of 08/041,431, filed Mar. 31, 1993 (abandoned).

BACKGROUND OF THE INVENTION

1. Field of the Invention

The present invention relates to the screening of drugs, especially random peptides, in yeast cells for the ability to interact with proteins involved in the post-translational modification, transport of and response to yeast pheromones or substitutes therefore.

2. Description of the Background Art

Drug Screening.

The identification of biological activity in new molecules has historically been accomplished through the use of in vitro assays or whole animals. Intact biological entities, either cells or whole organisms, have been used to screen for anti-bacterial, anti-fungal, anti-parasitic and anti-viral agents in vitro. Cultured mammalian cells have also been used in screens designed to detect potential therapeutic compounds. A variety of bioassay endpoints are exploited in mammalian cell screens including the stimulation of growth or differentiation of cells, changes in cell motility, the production of particular metabolites, the expression of specific proteins within cells, altered protein function, and altered conductance properties. Cytotoxic compounds used in cancer chemotherapy have been identified through their ability to inhibit the growth of tumor cells in vitro and in vivo. In addition to cultures of dispersed cells, whole tissues have served in bioassays, as in those based on the contractility of muscle.

In vitro testing is a preferred methodology in that it permits the design of high-throughput screens: small quantities of large numbers of compounds can be tested in a short period of time and at low expense. Optimally, animals are reserved for the latter stages of compound evaluation and are not used in the discovery phase; the use of whole animals is labor-intensive and extremely expensive.

Microorganisms, to a much greater extent than mammalian cells and tissues, can be easily exploited for use in rapid drug screens. Yeast provide a particularly attractive test system; extensive analysis of this organism has revealed the conservation of structure and function of a variety of proteins active in basic cellular processes in both yeast and higher eukaryotes.

The search for agonists and antagonists of cellular receptors has been an intense area of research aimed at drug discovery due to the elegant specificity of these molecular targets. Drug screening has been carried out using whole cells expressing functional receptors and, recently, binding assays employing membrane fractions or purified receptors have been designed to screen compound libraries for competitive ligands. Duke University, WO92/05244 (Apr. 2, 1992) describes the expression of mammalian G protein-coupled receptors in yeast and a means of identifying agonists and antagonists of those receptors using that organism.

In addition, yeast are, of course, used in the discovery of antifungal compounds; Etienne et al. (1990) describe the use of Saccharomyces cerevisiae mutant strains, made highly sensitive to a large range of antibiotics, for the rapid detection of antifungals.

Yeast Pheromone System Proteins and their Metabolic Function

Haploid yeast cells are able not only to grow vegetatively, but also to mate to form a diploid cell. The two mating types ("sexes") of haploid cells are designated a and α. The a cells produce the dodecapeptide a-factor, and the α cells, the tridecapeptide α-factor. Because a-factor and α-factor elicit a mating response in the yeast cell of the opposite "sex", they are called "pheromones". These pheromones, as well as other proteins specifically involved in the production or transport of, or response to, pheromones, are considered "pheromone system proteins".

The gene encoding a-factor pheromone, like the α-factor receptor gene, is an a cell-specific gene; a cell-specific genes are only expressed in a cells. The gene encoding α-factor pheromone, like the a-factor receptor gene, is an α cell-specific gene; α cell-specific genes are only expressed in α cells. Other yeast genes belong to a haploid-specific gene set and are expressed in haploid cells (a cells or α cells) but not in diploid (a/α) cells. In addition, there exists a diploid cell-specific gene set, including those genes involved in sporulation.

In eukaryotic cells, RNA polymerase II promoters contain a specific sequence (the TATA box) to which the transcription factor TFIID (TATA binding protein or TBP) binds. An active transcription initiation complex includes TFIID, accessory initiation proteins, and RNA Pol II. As in higher eukaryotic cells, the TATA box is an essential control sequence in yeast promoters. Yeast TATA-box-binding protein (TBP) was identified by its ability to substitute in function for mammalian TFIID [Buratowski et al., Nature 334, 37 (1988); Cavallini et al., Nature 334, 77 (1988)]. With only a few apparent exceptions [transcription of some glycolytic enzyme genes, see Struhl, Mol. Cell. Biol. 6, 3847 (1986) and Ogden et al., Mol. Cell Biol. 6, 4335 (1986)] transcription of yeast genes requires the proximal TATA box element and TFIID binding for initiation of transcription. Also required for efficient transcription are gene-specific activator proteins; the precise mechanism whereby these gene-specific regulatory proteins influence transcription has not been completely elucidated.

MCM1p (encoded in the MCM1 gene) is a non-cell-type-specific transcription factor in yeast. MCM1p acts alone or in concert with other regulatory proteins to control expression of a- and α-cell specific genes. Yeast mating type loci encode the regulatory proteins that contribute to the control of cell type-specific expression. These proteins are Mata1p (encoded by the MATa gene) and Matα1p and Matα2p (encoded by the MATα locus). MCM1p activates transcription of a-specific genes by binding to an upstream activation sequence (UAS) located in the control region of a-specific genes. Matα1p and MCM1p interact to enhance each other's binding to specific UAS binding sites to activate α-cell-specific gene transcription in α-cells. Matα2p associates with MCM1p to repress a-specific gene transcription in α-cells. In diploid (a/α) cells, Matα1p and Matα2p associate to repress the transcription of haploid-specific genes. The Matα1p/Matα2p regulatory entity is found only in diploid cells.

Yeast contain two genes encoding the α-factor pheromone, MFα1 and MFα2. Analysis of yeast bearing mutations in these sequences indicates that MFα1 gives rise to the majority of α-factor produced by cells. Expression occurs at a higher level from MFα1 than from MFα2 (Kurjan, Mol. Cell. Biol. 5, 787 (1985). The MFα1 gene of yeast encodes a 165 aa precursor protein containing an 85 aa leader sequence at the N-terminus. The leader includes a 19 aa signal sequence and a 66 aa sequence which contains sites for the addition of three oligosaccharide side chains (Kurjan and Herskowitz, Cell 39, 933 (1982); Singh et al. Nuc. Acids Res. 11, 4049 (1983); Julius et al. Cell 36, 309 (1984). Four tandem copies of the 13 aa α-factor are present in the C-terminal portion of the precursor; 6-8 aa spacer peptides precede the α-factor sequences (see FIG. 2).

After translocation of the nascent α-factor polypeptide to the ER, the signal sequence is cleaved from the precursor protein to yield pro-α-factor (Waters et al. J. Biol. Chem. 263, 6209 (1988). The core N-linked carbohydrate is added to three sites in the N-terminus of pro-α-factor (Emter et al. Biochem. Biophys. Res. Commun. 116, 822 (1983); Julius et al. Cell 36, 309 (1984); Julius et al. Cell 37, 1075 (1984). Additional glycosylation occurs in the Golgi prior to cleavage of pro-α-factor by the KEX2 endopeptidase. This enzyme cleaves within each of the spacer repeats leaving a Lys-Arg sequence attached to the C-terminus of α-factor peptide (Julius et al. Cell 37, 1075 (1984). The Lys-Arg sequence is removed by the action of the KEX-1 protease (Dmochowska et al. Cell 50, 573 (1987). The additional spacer residues present at the N-terminus of α-factor peptide are removed by the dipeptidyl aminopeptidase encoded by STE13 (Julius et al. Cell 32, 839 (1983). Four α-factor peptides are released from each precursor protein via the proteolytic processing outlined above and the mature α-factor is secreted from the cell.

Precursors of the 12 aa mature a-factor peptide are encoded in the MFa1 and MFa2 genes and are 36 aa and 38 aa residues, respectively (for schematic of MFa1 gene see FIG. 5). The precursors contain one copy of a-factor and the products of the two genes differ in sequence at one amino acid. The two forms of a-factor are produced in equal amounts by a cells (Manney et al. in *Sexual interactions in eukaryotic microbes*, p 21, Academic Press, New York (1981).

Processing of a-factor entails a process that differs in every detail from that of α-factor. The processing of a-factor begins in the cytosol and involves the farnesylation of the C-terminal cysteine residue near the carboxyl terminus (-CVIA) by a farnesyl transferase (Schafer et al. Science 245, 379 (1989); Schafer et al. Science 249, 1133 (1990). The α and β subunits of the farnesyl transferase are encoded by the RAM2 and RAM1 genes, respectively (He et al. Proc. Natl. Acad. Sci. 88, 11373 (1991). Subsequent to farnesylation is the proteolytic removal of the three amino acids that are C-terminal to the modified cysteine by a membrane-bound endoprotease. Next, the carboxy-terminal farnesylated cysteine residue is modified further: the carboxyl group is methylated by the product of the STE14 gene. STE14p is a membrane-bound S-farnesyl-cysteine carboxyl methyl transferase (Hrycyna et al. EMBO. J. 10, 1699 (1991). The mechanisms of the N-terminal processing of a-factor have not been elucidated. After processing of the precursors is complete, mature a-factor is transported to the extracellular space by the product of the STE6 gene (Kuchler et. al. EMBO J. 8, 3973 (1989), an ATP-binding cassette (ABC) transporter.

In normal *S. cerevisiae* (budding yeast) a cells, the α-factor binds the G protein-coupled membrane receptor STE2. The G protein dissociates into the $G_\alpha$ and $G_{\beta\gamma}$ subunits, and the $G_{\beta\gamma}$ binds an unidentified effector, which in turn activates a number of genes. STE20, a kinase, activates STE5, a protein of unknown function. STE5 activates STE11 kinase, which stimulates STE7 kinase, which induces the KSS1 and/or FUS3 kinases. These switch on expression of the transcription factor STE12. STE12 stimulates expression of a wide variety of genes involved in mating, including FUS1(cell fusion), FAR1 (cell-cycle arrest), STE2 (the receptor), MFA1 (the pheromone), SST2 (recovery), KAR3 (nuclear fusion) and STE6 (pheromone secretion). Other genes activated by the pathway are CHS1, AGα1, and KAR3. The multiply tandem sequence TGAAACA (SEQ ID NO: 128) has been recognized as a "pheromone response element" found in the 5'-flanking regions of many of the genes of this pathway.

One of the responses to mating pheromone is the transient arrest of the yeast cell in the G1 phase of the cell cycle. This requires that all three G1 cyclins (CLN1, CLN2, CLN3) be inactivated. It is believed that FUS3 inactivates CLN3, and FAR1 inhibits CLN2. (The product responsible for inactivating CLN1 is unknown).

The growth arrest is terminated by a number of different mechanisms. First, the α-factor receptor is internalized following binding of the pheromone, resulting in a transient decrease in the number of pheromone binding sites. Second, the C-terminal tail of the receptor is phosphorylated consequent to ligand binding, resulting in uncoupling of the receptor from the transducing G proteins. Third, pheromone-induced increases in expression of GPA1p (the Gα-subunit of the heterotrimeric G protein) increase the level of the α subunit relative to the $G_\beta$ and $G_\gamma$ subunits, resulting in reduction in the level of free $G_{\beta\gamma}$ and consequent inactivation of the pheromone response pathway. Additional mechanisms include induction of the expression of SST2 and BAR1 and phosphorylation of the α subunit (perhaps by SVG1).

Signaling is inhibited by expression of a number of genes, including CDC36, CDC39, CDC72, CDC73, and SRM1. Inactivation of these genes leads to activation of the signaling pathway.

A similar pheromone signaling pathway may be discerned in α cells, but the nomenclature is different in some cases (e.g., STE3 instead of STE2).

Other yeast also have G protein-mediated mating factor response pathways. For example, in the fission yeast *S. pombe*, the M factor binds the MAP3 receptor, or the P-factor the MAM2 receptor. The dissociation of the G protein activates a kinase cascade (BYR2, BYR1, SPK1), which in turn stimulates a transcription factor (STE11). However, in *S. pombe*, the Gα subunit transmits the signal, and there are of course other differences in detail.

Pheromone Pathway Mutants

The effects of spontaneous and induced mutations in pheromone pathway genes have been studied. These include the α-factor (MFα1 and MFα2) genes, see Kurjan, Mol. Cell. Biol., 5:787 (1985); the a-factor (MFa1 and MFa2) genes, see Michaelis and Herskowitz, Mol. Cell. Biol. 8:1309 (1988); the pheromone receptor (STE2 and STE3) genes, see Mackay and Manney, Genetics, 76:273 (1974), Hartwell, J. Cell. Biol., 85:811 (1980), Hagen, et al., P.N.A.S. (USA), 83:1418 (1986); the FAR1 gene, see Chang and Herskowitz, Cell, 63:999 (1990); and the SST2 gene, see Chan and Otte, Mol. Cell. Biol., 2:11 (1982).

Expression of Foreign Proteins in Yeast Cells

A wide variety of foreign proteins have been produced in *S. cerevisiae*, either solely in the yeast cytoplasm or through exploitation of the yeast secretory pathway (Kingsman et al. TIBTECH 5, 53 (1987). These proteins include, as examples, insulin-like growth factor receptor (Steube et al. Eur. J. Biochem. 198, 651 (1991), influenza virus hemagglutinin (Jabbar et al. Proc. Natl. Acad. Sci. 82, 2019 (1985) , rat liver cytochrome P-450 (Oeda et al. DNA 4, 203 (1985) and functional mammalian antibodies (Wood et al. Nature 314, 446 (1985). Use of the yeast secretory pathway is preferred since it increases the likelihood of achieving faithful folding, glycosylation and stability of the foreign protein. Thus, expression of heterologous proteins in yeast often involves fusion of the signal sequences encoded in the genes of yeast secretory proteins (e.g., α-factor pheromone or the SUC2 [invertase] gene) to the coding region of foreign protein genes.

A number of yeast expression vectors have been designed to permit the constitutive or regulated expression of foreign proteins. Constitutive promoters are derived from highly expressed genes such as those encoding metabolic enzymes like phosphoglycerate kinase (PGK1) or alcohol dehydrogenase I (ADH1) and regulatable promoters have been derived from a number of genes including the galactokinase (GAL1) gene. In addition, supersecreting yeast mutants can be derived; these strains secrete mammalian proteins more efficiently and are used as "production" strains to generate large quantities of biologically active mammalian proteins in yeast (Moir and Davidow, Meth. in Enzymol. 194, 491 (1991).

A variety of heterologous proteins have been expressed in yeast cells as a means of generating the quantity of protein required for commercial use or for biochemical study (Kingsman et al. TIBTECH 5, 53 (1987). In addition, a number of mammalian proteins have been expressed in yeast in order to determine whether the proteins (1) will functionally substitute for cognate proteins normally expressed within that organism or (2) will interact with accessory yeast proteins to accomplish a specific function. Thus it has been determined that a human TBP with altered binding specificity will function to initiate transcription in yeast [Strubin and Struhl, Cell 68, 721 (1992)]. In addition, mammalian steroid hormone receptors [Metzger et al. (1988); Schena and Yamamoto (1988)] and human p53 [Schärer and Iggo, Nuc. Acids Res. 20, 1539 (1992)] were shown to activate transcription in yeast.

Expression in yeast of the gag-pol gene of HIV-1 results in the processing of the gag protein precursor to yield the products which normally arise within the virion; processing in yeast, as in the virus, is due to the action of the protease encoded within the gag-pol gene (Kramer et al. Science 231, 1580 (1986).

A number of mammalian ABC transporters have been expressed in yeast to determine their ability to substitute for yeast Ste6p in the transport of pheromone. The mammalian proteins thus far tested include human Mdr1 (Kuchler and Thorner, Proc. Natl. Acad. Sci. 89, 2302 (1992)) and murine Mdr3 (Raymond et al. Science 256, 232 (1992), proteins involved in multidrug resistance; in addition, a chimeric protein containing human CFTR (cystic fibrosis transmembrane conductance regulator) and yeast STE6 sequence has been shown to transport a-factor pheromone in yeast (Teem et al. Cell 73, 335 (1993)

An a cell may be engineered to produce the a-factor receptor, and an α cell to make α-factor receptor. Nakayama, et al., EMBO J., 6:249-54 (1987); Bender and Sprague, Jr., Genetics 121: 463-76 (1989).

Heterologous G protein-coupled receptors have been functionally expressed in *S. cerevisiae*. Marsh and Hershkowitz, Cold Spring Harbor Symp., Quant. Biol., 53: 557-65 (1988) replaced the *S. cerevisiae* STE2 with its homologue from *S. Kluvven*. More dramatically, a mammalian beta-adrenergic receptor and Gα subunit have been expressed in yeast and found to control the yeast mating signal pathway. King, et al., Science, 250: 121-123 (1990).

Duke University, WO92/05244 (Apr. 2, 1992) describes a transformed yeast cell which is incapable of producing a yeast G protein α subunit, but which has been engineered to produce both a mammalian G protein α subunit and a mammalian receptor which is "coupled to" (i.e., interacts with) the aforementioned mammalian G protein α subunit. Specifically, Duke reports expression of the human beta-2 adrenergic receptor (hβAR), a seven transmembrane receptor (STR), in yeast, under control of the GAL1 promoter, with the hβAR gene modified by replacing the first 63 base pairs of coding sequence with 11 base pairs of noncoding and 42 base pairs of coding sequence from the STE2 gene. (STE2 encodes the yeast α-factor receptor). Duke found that the modified hβAR was functionally integrated into the membrane, as shown by studies of the ability of isolated membranes to interact properly with various known agonists and antagonists of hβAR. The ligand binding affinity for yeast-expressed hβAR was said to be nearly identical to that observed for naturally produced hβAR.

Duke co-expressed a rat G protein α subunit in the same cells, yeast strain 8C, which lacks the cognate yeast protein. Ligand binding resulted in G protein-mediated signal transduction.

Duke teaches that these cells may be used in screening compounds for the ability to affect the rate of dissociation of Gα from Gβγ in a cell. For this purpose, the cell further contains a pheromone-responsive promoter (e.g. BAR1 or FUS1), linked to an indicator gene (e.g. HIS3 or LacZ). The cells are placed in multi-titer plates, and different compounds are placed in each well. The colonies are then scored for expression of the indicator gene.

Duke's yeast cells do not, however, actually produce the compounds to be screened. As a result, only a relatively small number of compounds can be screened, since the scientist must ensure that a given group of cells is contacted with only a single, known compound.

Yeast have been engineered to express foreign polypeptide variants to be tested as potential antagonists of mammalian receptors. Libraries encoding mutant glucagon molecules were generated through random misincorporation of nucleotides during synthesis of oligonucleotides containing the coding sequence of mammalian glucagon. These libraries were expressed in yeast and culture broths from transformed cells were used in testing for antagonist activity on glucagon receptors present in rat hepatocyte membranes (Smith et al. 1993).

Drugs which overcome the multiple drug resistance (MDR) of cancer cells may be identified by using transformed yeast cells expressing P-glycoprotein (Suntory Ltd., patent application JP 2257873 entitled "Multiple drug resistance-relating gene-comprises P-glycoprotein accumulated in cell membrane part of transformed yeast"). The drugs were not produced by the yeast cells in question.

A yeast strain has been derived to allow the identification of inhibitors of protein farnesyltransferase which exhibit activity against mammalian Ras and which may therefore function as antitumor drugs (Hara et al. 1993).

Genetic Markers in Yeast Strains

Yeast strains that are auxotrophic for histidine (HIS3) are known, see Struhl and Hill), Mol. Cell. Biol., 7:104 (1987); Fasullo and Davis, Mol. Cell. Biol., 8:4370 (1988). The HIS3 (imidazoleglycerol phosphate dehydratase) gene has been used as a selective marker in yeast. See Sikorski and Heiter, Genetics, 122:19 (1989); Struhl, et al., P.N.A.S. 76:1035 (1979); and, for FUS1-HIS3 fusions, see Stevenson, et al., Genes Dev., 6:1293 (1992 ).

Peptide Libraries. Peptide libraries are systems which simultaneously display, in a form which permits interaction with a target, a highly diverse and numerous collection of peptides. These peptides may be presented in solution (Houghten), or on beads (Lam), chips (Fodor), bacteria (Ladner U.S. Pat. No. 5,223,409), spores (Ladner U.S. Pat. No. '409), plasmids (Cull) or on phage (Scott, Devlin, Cwirla, Felici, Ladner '409). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

Ladner, U.S. Pat. No. 5,096,815 describes a method of identifying novel proteins or polypeptides with a desired DNA binding activity. Semi-random ("variegated") DNA encoding a large number of different potential binding proteins is introduced, in expressible form, into suitable host cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a pheromone system protein surrogate.

Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., J. Biol. Chem. 264, 20206 (1989) and Kaiser et al. Science 235, 312 (1987), respectively).

All references cited in this specification are hereby incorporated by reference. No admission is made that any reference constitutes prior art.

SUMMARY OF THE INVENTION

In the present invention, a yeast cell is engineered to express an exogenous protein which is, however, capable of substituting for a yeast protein which is involved in the post-translational modification, transport, recognition or signal transduction of a yeast pheromone, sufficiently, to be able, at least under some circumstances, to carry out that role of the yeast protein. For the sake of convenience, these yeast proteins will be referred to as "pheromone system proteins" (PSP), and their cognate non-yeast proteins as PSP surrogates.

The pheromone system of a yeast cell is thus subverted so that the response of the cell to a yeast pheromone (or a ligand of the yeast pheromone receptor) is at least partially determined by the activity of the surrogate PSP. In a preferred embodiment, the cognate yeast PSP is not produced in functional form, so that the response is essentially entirely dependent on the activity of the surrogate PSP.

Such yeast cells may be used to identify drugs which inhibit or activate, to a detectable degree, the ability of the surrogate to substitute for the cognate yeast PSP. To screen for an inhibitor, a normally functional surrogate is expressed, and the presence of an inhibitor is indicated by a depression of the cellular response. To screen for an activator, a surrogate functional in yeast, or one normally not functional in yeast but which is activatable (the latter is preferred, to minimize background) is used, and the activator is detected through its elevation of the cellular response.

In a preferred embodiment, the candidate drug is a peptide, and the yeast cell is engineered to express the candidate drug as well as the surrogate PSP.

Another consideration is that with wild-type yeast cells, to achieve pheromone secretion and response, both α and a cells must be provided. In some preferred embodiments, α cells are engineered to express α-factor receptor or a cells are engineered to express a-factor receptor. These modified cells may be considered "autocrine" because they are "self-stimulatory". Cells which express both a surrogate for the pheromone receptor, and a heterologous peptide agonist for the surrogate receptor, are also considered "autocrine", because they will respond to the co-produced agonist.

The classes of PSPs and PSP surrogates are numerous. In one embodiment, the PSP surrogate is a surrogate for a PSP involved in the upstream processing of the pheromone prior to its interaction with the receptor. In sub-embodiments, the PSP may be one involved in the post-translational modification of the precursor protein to yield mature pheromone (e.g., proteases, carboxymethyltransferases or farnesyltransferases) or one involved in the secretion or transport of the pheromone (e.g., an ABC transporter). The pheromone itself, and its precursor, may also be considered an upstream PSP.)

In another embodiment, the PSP surrogate is a surrogate for a G protein-coupled receptor.

In a third embodiment, the PSP surrogate is a surrogate for a G protein or G protein subunit, especially the alpha subunit.

In a fourth embodiment, the PSP surrogate is a surrogate for a PSP involved in the downstream transduction of a signal received by the pheromone receptor. Such PSPs include kinases and cyclins. Examples of these embodiments are discussed in more detail below.

Farnesyltransferases and Carboxymethyltransferases. After expression, a-factor is farnesylated by RAM1p and RAM2p and carboxymethylated by Ste14p. These modifications are required for activity.

RAM1p and RAM2p are homologous to the subunits of the heterodimeric mammalian farnesyltransferase, which itself is necessary for membrane association of mammalian Ras proteins. If a yeast cell is engineered to express the mammalian farnesyltransferase, it may be used to identify drugs which interact with that enzyme by determining whether a functional a-factor is produced. Similarly, Ste14p is homologous to mammalian carboxymethyltransferases, which play regulatory roles in controlling the function of low molecular weight G proteins (Ras, Rho, Rab).

Proteases. The PSP may be a yeast protease, such as KEX2, STE13 or KEX1. Yeast α-factor pheromone is generated through the controlled and limited proteolysis of precursor proteins by these proteases. A yeast cell may be engineered to express an inactive precursor of yeast α-factor in which a peptide linker, corresponding to the cleavage site of a surrogate non-yeast protease, is incorporated so that cleavage will liberate mature α-factor (or its functional homologue). For example, the PSP surrogate may be HIV protease, with the cleavage site of HIV protease being substituted for the yeast protease cleavage sites in the α-factor precursor. The precursor and the HIV protease are co-expressed in the yeast cell. Proteolysis by HIV protease will give rise to production of mature α-factor and initiation of signal transduction. This system may be used to identify inhibitors of HIV protease.

Preferably, unlike yeast cells occurring in nature, the yeast cell is engineered not only to express the α-factor precursor, but also the α-factor receptor, so that a single haploid type of yeast is all that is required to conduct the assay.

ABC Transporters. Ste6 is the yeast ABC transporter necessary for the export of a-factor. The yeast cell is engineered to express) both a-factor and a foreign ABC transporter. This transporter may be one which is not, by itself, able to transport a-factor, but which in the presence of a drug of interest, is capable of doing so, or it may be one which is already functional.

Preferably, the yeast cell is engineered to express not only a-factor, but also the a-factor receptor.

G Protein-Coupled Receptors. The PSP may be a yeast pheromone receptor. The surrogate is a non-yeast, G protein-coupled receptor. In order to achieve coupling to the pheromone signal transduction pathway, it may be necessary to provide a foreign or chimeric $G_\alpha$ or $G_{\beta\gamma}$ subunit.

The engineered yeast cell may be used to screen for agonists as well as antagonists. When used to screen for agonists, it is preferable that the yeast pheromone not be produced in functional form.

Protein Kinases. The PSP may be a protein kinase, such as the FUS1, KSS1, STE11 or STE7 proteins, which participate in the cellular response to pheromones. The PSP surrogate would be, e.g., a mammalian, mitogen-activated protein kinase. Yeast cells engineered to express the surrogate protein kinase could be used to screen for activators or inhibitors thereof.

Cyclins. The PSP may be a cyclin, such as CLN1, CLN2 or CLN3. The cyclins regulate the progression of cells through the cell cycle. The human C, D1 and E cyclins are capable of substituting functionally for the CLN proteins of yeast. Inhibitors of mammalian cyclins may be useful in cancer chemotherapy. Yeast cells engineered to express a surrogate cyclin may be used to identify molecules which inhibit (or enhance) its activity.

Peptide Libraries

While others have engineered yeast cells to facilitate screening of exogenous drugs as receptor agonists and antagonists, the cells did not themselves produce both the drugs and the receptors. Yeast cells engineered to produce the receptor, but that do not produce the drugs themselves, are inefficient. To utilize them one must bring a sufficient concentration of each drug into contact with a number of cells in order to detect whether or not the drug has an action. Therefore, a microtiter plate well or test tube must be used for each drug. The drug must be synthesized in advance and be sufficiently pure to judge its action on the yeast cells. When the yeast cell produces the drug, the effective concentration is higher.

In a preferred embodiment, the yeast cells collectively produce a "peptide library", preferably including at least $10^7$ different peptides, so that diverse peptides may be simultaneously assayed for the ability to interact with the PSP surrogate.

In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

Detection of Signal Transduction

Yeast cells may also be engineered so that their pheromone signal transduction pathways provide a more readily detectable evidence of the activity of a suspected drug. In these embodiments, the drug need not be a peptide produced by the same yeast cell, or even a peptide at all.

As previously mentioned, one of the consequences of activation of the pheromone signal pathway in wild-type yeast is growth arrest. If one is testing for an antagonist of a G protein-coupled receptor, or of other pheromone system proteins, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

However, when searching for peptides which can function as agonists. of G protein-coupled receptors, or other pheromone system proteins, the growth arrest consequent to activation of the pheromone response pathway is an undesirable effect for this reason: cells that bind peptide agonists stop growing while surrounding cells that fail to bind peptides will continue to grow. The cells of interest, then, will be overgrown or their detection obscured by the background cells, confounding identification of the cells of interest. To overcome this problem the present invention teaches engineering the cell such that: 1) growth arrest does not occur as a result of pheromone signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

It is, of course, desirable that the exogenous receptor (or other PSP surrogate) be exposed on a continuing basis to the peptides. Unfortunately, this is likely to result in desensitization of the pheromone pathway to the stimulus. Desensitization may be avoided by mutating (which may include deleting) the SST2 gene so that it no longer produces a functional protein, or by mutating other genes which may contribute to desensitization, e.g., BAR1 in the case of a cells and SVG1 for either a or α cells.

If the endogenous pheromone receptor (or other cognate PSP) is produced by the yeast cell, the assay will not be able to distinguish between peptides which interact with the pheromone receptor (or other cognate PSP) and those which interact with the exogenous receptor (or other PSP surrogate). It is therefore desirable that the endogenous gene be deleted or otherwise rendered nonfunctional.

The claims are hereby incorporated by reference as a further description of the preferred embodiments.

Figure 1:
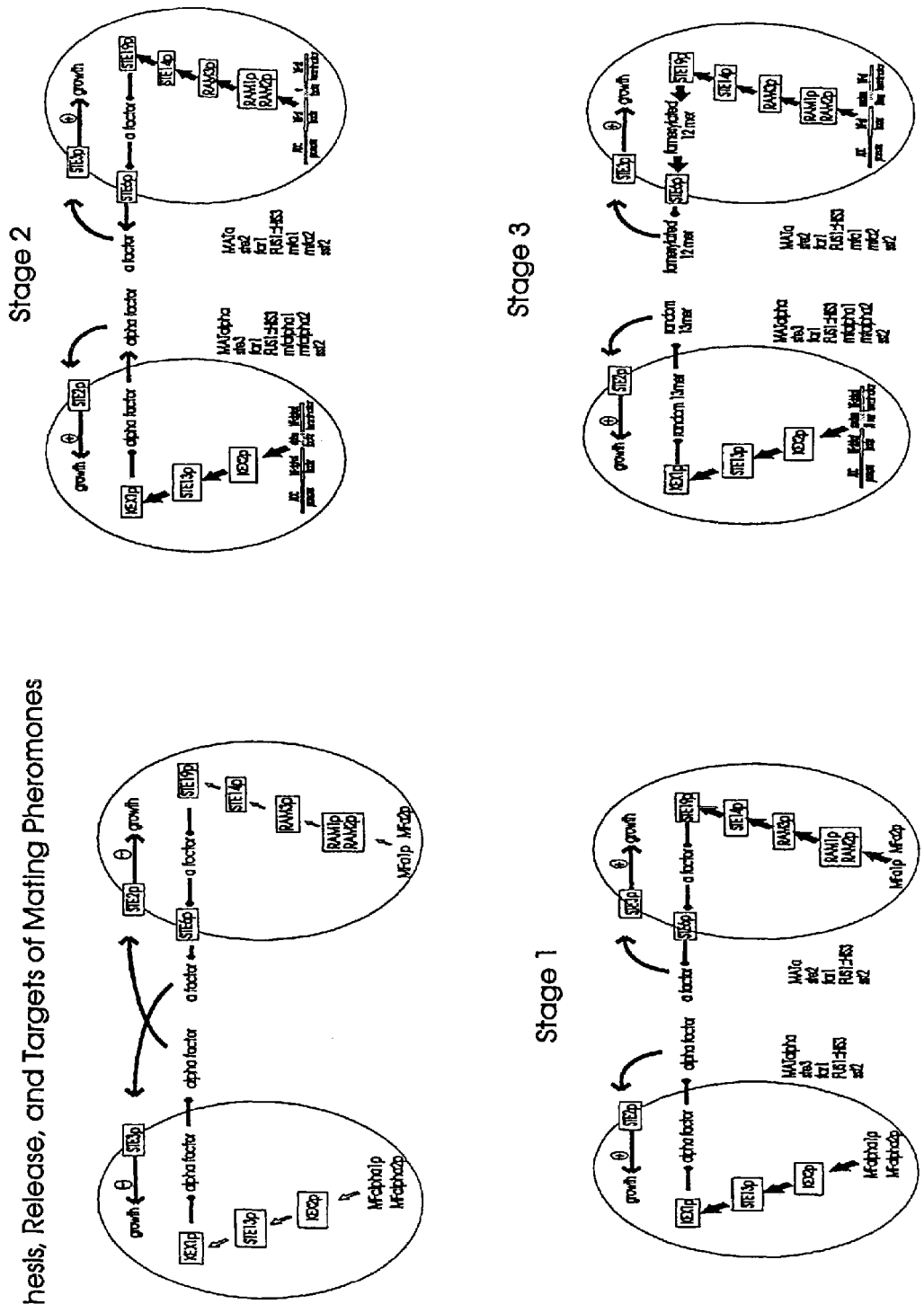
FIG. 1. Outline of successive stages in the development of yeast autocrine systems.

An outline of the normal synthesis and release of mating pheromones is diagrammed in the upper left. Two genes, MFα1 and MFα2, encode precursor proteins (MFα1p and MFα2p) containing four and two repeats, respectively, of the tridecapeptide representing mature α-factor. These precursors are processed proteolytically in a series of enzymatic reactions that begin with cleavage of the signal sequence in the endoplasmic reticulum and involve both glycosylation of the leader peptide and cleavage by the proteases KEX2p, STE13p, and KEX1P. The result is the secretion of mature α-factor which, upon binding to STE2p normally expressed on the surface of a cells, elicits a number of changes in the a cells, including growth arrest. The a cells, in turn, express two genes, MFa1 and MFa2, which encode precursors (MFa1p and MFa2p) for a-factor. These precursors undergo farnesylation by RAM1 and RAM2, proteolytic trimming of the C-terminal three amino acids (by a protein tentatively identified as RAM3p), carboxymethylation of the newly exposed C-terminal cysteine by STE14p, and endoproteolytic removal of the N-terminal leader sequence by an activity provisionally identified as STE19p. Upon export of the mature a-factor from the cell via STE6p, it binds to STE3p expressed on the surface of α cells and stops their growth.

Stage 1 involves the development of yeast strains in which SST2, FAR1, and HIS3 are inactivated and a suitable reporter construct like fus1::HIS3 is integrated into the genomes of both α and a cells. α cells are further altered by replacement of the normally expressed STE3p with STE2p, while a cells are further modified by replacement of the normally expressed STE2p with STE3p. The resulting strains should show growth on histidine-deficient media in the absence of exogenous pheromone.

Stage 2 involves, first, inactivation of MFα1 and MFα2 in cells and inactivation of MFa1 and MFa2 in a cells developed in Stage 1. These modifications will result in strains which are auxotrophic for histidine. Next, the appropriate expression plasmid will be introduced: the expression plasmid pADC-MF (see FIG. 4) containing an oligonucleotide encoding α-factor should confer upon α cells the ability to grow on histidine-deficient media; the expression plasmid pADC-MFa (see FIG. 6) containing an oligonucleotide encoding a-factor should enable a cells to grow on histidine-deficient media.

Stage 3 uses the cells developed in Stage 2 for the insertion of expression plasmids. However, instead of using plasmids which contain oligonucleotides that encode genuine pheromone, the yeast will be transformed with expression plasmids that contain random or semi-random oligonucleotides. Transformants which can grow on histidine-deficient media will be expanded and their plasmids isolated for sequencing of the inserted oligonucleotide.

FIG. 2. Diagram of the plasmid used for mutagenesis of MFα1. A 1.8 kb EcoRI fragment containing MFα1 is cloned into the EcoRI site of pALTER such that single-stranded DNA containing the MFα1 minus strand can be synthesized. The diagram illustrates the different regions of MFα1, including the promoter, transcription terminator, and different domains of the precursor protein: the signal peptide, the pro peptide, the four repeats of mature α-factor, and the three spacers which separate these repeats. Above the block diagram of the regions of MFα1 are the amino acid sequences (SEQ ID NO:1) of the signal peptide and the pro peptide; below it are those of the pheromone repeats and the spacers (SEQ ID NO:2). The sites of proteolytic processing of the precursor protein are indicated by arrows, with each proteolytic activity represented by a different arrow, as indicated in the figure.

FIG. 3. Diagram of the plasmids used in the construction of the MFα expression cassette. pAAH5 contains the ADC1 promoter which will be used to drive expression of synthetic oligonucleotides inserted into the MFα expression cassette. The 1.5 kb BamHI to HindIII fragment containing the ADC1 promoter will be cloned into pRS426, a plasmid which functions as a high-copy episome in yeast, to yield pRS-ADC. pRS-ADC will be the recipient of MFα1 sequences which have been mutated as follows: the region of MFα1 which encodes mature α-factor will be replaced with restriction sites that can accept oligonucleotides with Afl II and BglII ends. Insertion of oligonucleotides with AflII and BglII ends will yield a plasmid which encodes a protein containing the MFα1 signal and leader sequences upstream of the sequence encoded by the oligonucleotide. The MFα1 signal and leader sequences should direct the processing of this precursor protein through the pathway normally used for the secretion of mature α-factor.

FIG. 4. Diagram of constructs used for the expression of random oligonucleotides in the context of MFα1. Oligonucleotides containing a region of 39 random base pairs (shown at the top of the figure) will be cloned into the AflII and BglII sites of the MFα1 expression cassette. These oligonucleotides will encode the six amino acids immediately N-terminal to the first repeat of the α-factor in MFα1, followed in succession by a tridecapeptide of random sequence and a stop codon. Yeast transformed with these constructs and selected for an ability to grow on media deficient in uracil will use the ADC1 promoter to express a protein consisting of the MFα1 leader (both pre and pro peptides) followed by 13 random amino acids. Processing of the leader sequences will result in secretion of the tridecapeptide. A nucleotide sequence (SEQ ID NO:3) is presented upstream of the leader sequence and a second nucleotide sequence (SEQ ID NO:4) containing AflII, XhoI and BglII sites and coding for a peptide with an amino acid sequence (SEQ ID NO:5) is presented downstream from the leader sequence. A nucleotide sequence (SEQ ID NO:6) containing an AflII and a BclI site encodes for a peptide with an amino acid sequence (SEQ ID NO:7).

FIG. 5. Diagram of the plasmid used for mutagenesis of MFa1. A 1.6 kb BamHI fragment containing MFa1 is cloned into the BamHI site of pALTER such that single-stranded DNA containing the MFa1 minus strand can be synthesized. The diagram illustrates the different regions of MFa1, including the promoter, transcription terminator, and different domains of the precursor protein: the leader peptide; the dodecapeptide that represents the peptide component of mature a-factor and whose C-terminal cysteine becomes farnesylated and carboxymethylated during processing; and the C-terminal three amino acids that are removed during processing of the precursor. Above the block diagram of the regions of MFa1 is the amino acid sequence (SEQ ID NO:8) of the primary translation product.

FIG. 6. Diagram of constructs used for the expression of random oligonucleotides in the context of MFa1. Oligonucleotides containing a region of 33 random base pairs (shown at the top of the figure) will be cloned into the XhoI and AflII sites of the MFa1 expression cassette. These oligonucleotides will encode the seven amino acids immediately N-terminal to the first amino acid of mature a-factor, followed in succession by a monodecapeptide of random sequence, a cysteine which is farnesylated and carboxymethylated during processing of the precursor, three amino acids (VIA) which are proteolytically removed during processing, and a stop codon. Yeast transformed with these constructs and selected for an ability to grow on media deficient in uracil will use the ADC1 promoter to express a precursor protein consisting of the MFa1 leader followed by 11 random amino acids and a C-terminal tetrapeptide CVIA. Processing of this precursor will result in secretion of a C-terminally farnesylated, carboxymethylated dodecapeptide which consists of 11 random amino acids and a C-terminal cysteine. A nucleotide sequence (SEQ ID NO:9) is presented upstream of the MFaI leader and a second nucleotide sequence (SEQ ID NO:10) containing an AflII and a XhoI site and encoding for a peptide with an amino acid sequence (SEQ ID NO:11) is presented downstream from the MFaI leader. A nucleotide sequence (SEQ ID NO:12) containing corresponding AflII and XhoI sites for cloning into SEQ ID NO:10 encodes for a peptide with an amino acid sequence (SEQ ID NO:13).

Figure 7:
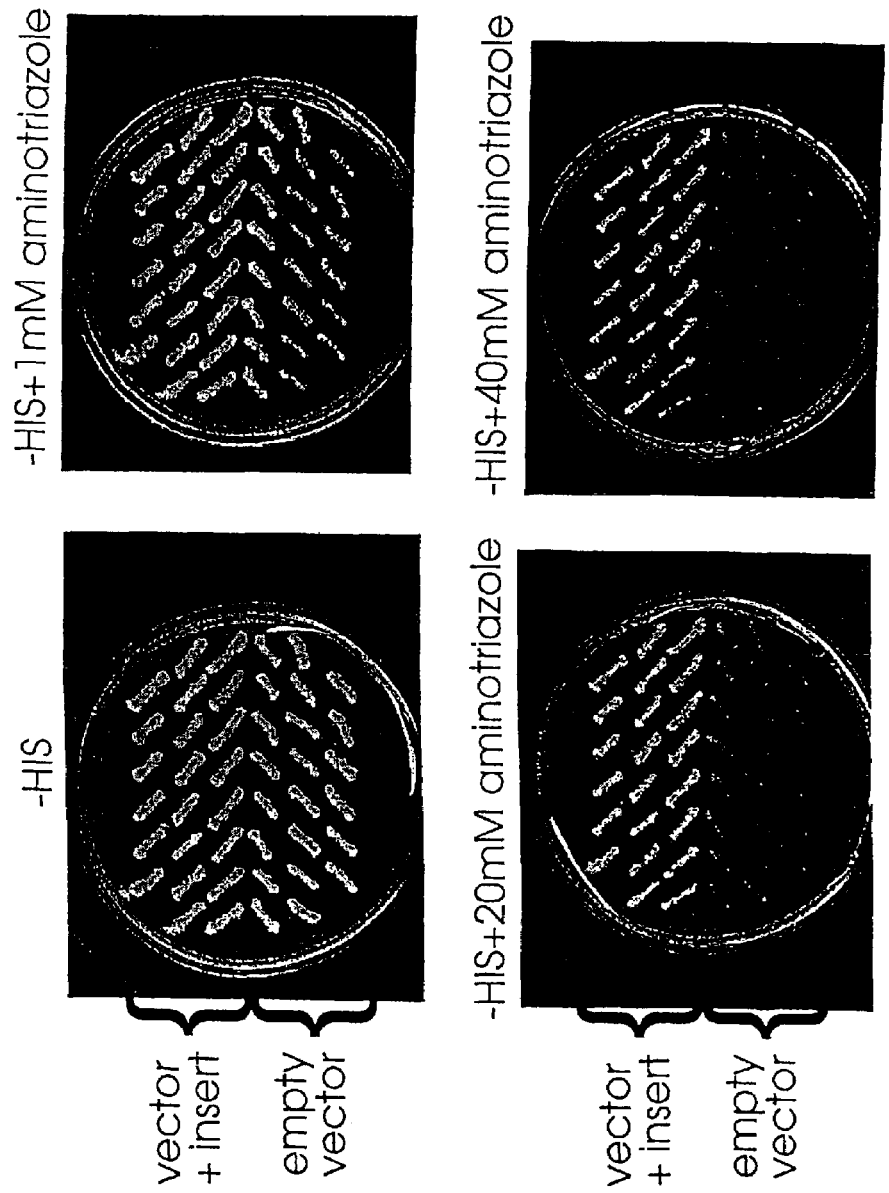

FIG. 7. Autocrine Matα strain secretes and responds to signalling by α-factor.

A synthetic oligonucleotide encoding the yeast α-factor pheromone was expressed in Matα cells. These cells normally express the a-factor pheromone but were prevented from doing so by deletion of the endogenous a-factor-encoding genes. Expression and release of α-factor by these cells renders them "autocrine" with regard to pheromone signalling. The peptide containing mature α-factor was processed within these cells for transport through the yeast secretory pathway to the extracellular environment. Pheromone signalling was initiated by the binding of α-factor to the Ste2 receptor expressed in Matα cells. Signalling by pheromone in the strain background used in these experiments results in growth of responsive cells on media that is deficient in histidine. Background growth of control cells that are not expressing α-factor is prevented by increasing concentrations of the HIS3 inhibitor, aminotriazole.

Figure 8:
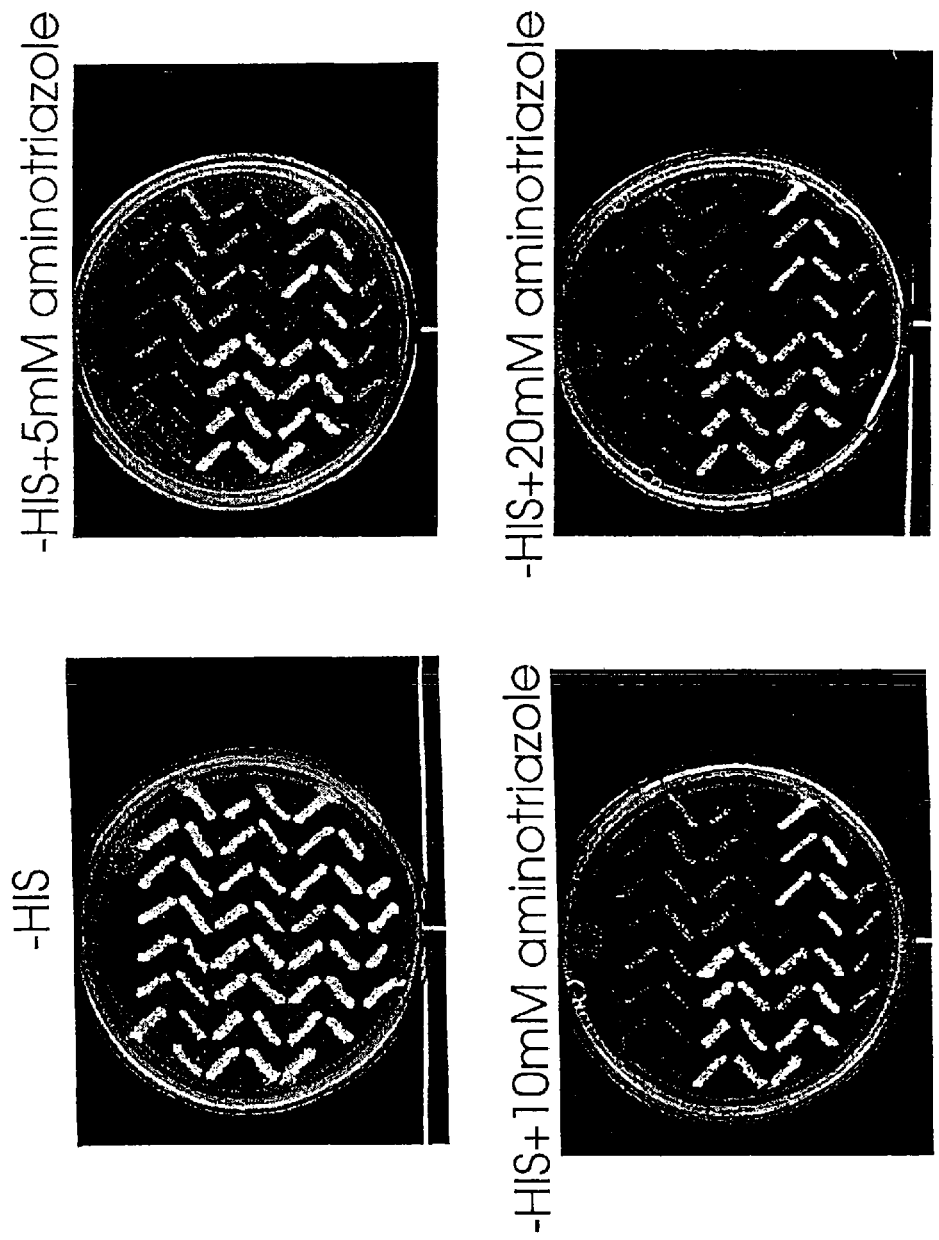

FIG. 8. Autocrine MATa strain secretes and responds to signalling by a-factor.

Yeast a-factor was expressed from a plasmid containing a synthetic pheromone-encoding oligonucleotide in Mata cells. The yeast used in these experiments were made "autocrine" by replacement of the normally expressed Ste2 protein with the receptor for a-factor, Ste3. The a-factor peptide was processed in these cells and transported to the extracellular environment by the endogenous Ste6 protein, an ATP-dependent transmembrane transporter. Pheromone signalling initiated by the a-factor released by these cells when bound to Ste3 is indicated by the growth of the cells on histidine-deficient media. Background growth of control cells, which are incapable of expressing a-factor (these α cells lack the plasmid which encodes the pheromone) is prevented by increasing concentrations of the HIS3 inhibitor, aminotriazole.

Figure 9:
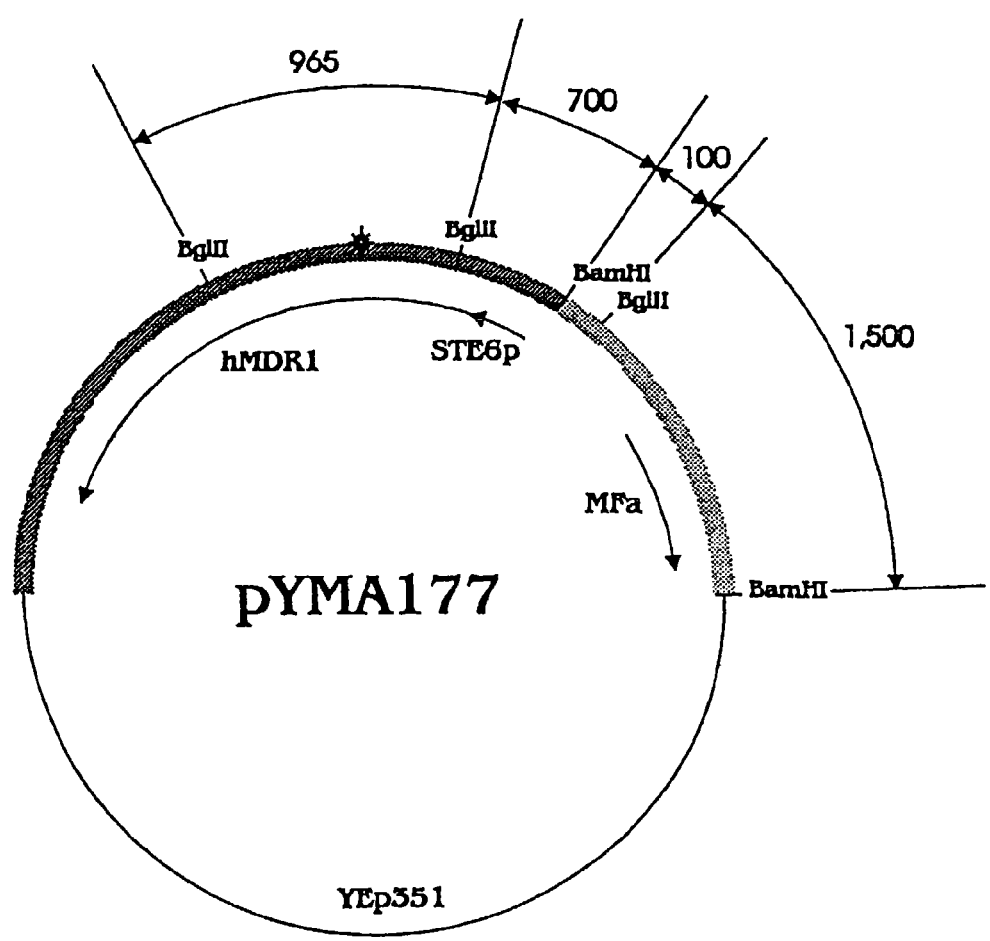

FIG. 9. Plasmid pYMA177 containing mutant human MDR1 (G185V mutation).

The plasmid pYMA177 was constructed by Karl Kuchler and permits the simultaneous overexpression of both a mutant human Mdr1 protein and the yeast a-factor pheromone precursor (Kuchler & Thorner, Proc. Natl. Acad. Sci. 89, 2302 (1992)

Cadus 1270, containing a galactose inducible, amino-terminal myc-tagged form of the C5a receptor, was used to transform a protease deficient strain of yeast.

Figure 10:
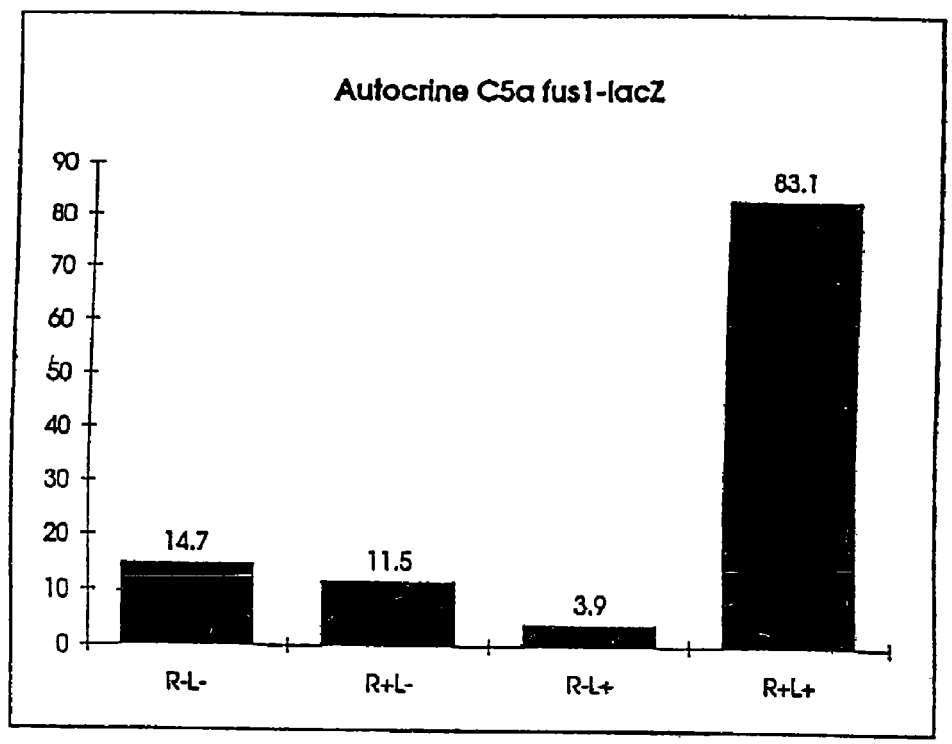

FIG. 10. Activity of a fus1 promoter in response to signalling by human C5a expressed in autocrine strains of yeast.

To verify and quantify pheromone pathway activation upon stimulation of the C5a receptor by C5a in yeast, the activity of the fus1 promoter was determined colorometrically using a fus1-lacZ fusion. CY878 (MATα tbt1-1 fus1-HIS3 can1 ste14::trp1::LYS2 ste3*1156 gpa1(41)-Gαi2) was transformed with CADUS 1584 (pRS424-fus1-lacZ) in addition to receptor and ligand plasmids listed below. Transformants were grown overnight in synthetic medium lacking leucine, uracil, and tryptophan, pH 6.8, 50 mM PIPES to an $OD_{600}$ of less than 0.8 and β-galactosidase activity (Guarente 1983) was assayed.

Cadus 1289+Cadus 1215=Receptor⁻Ligand⁻=(R−L−)

Cadus 1303+Cadus 1215=Receptor⁺Ligand⁻=(R+L−)

Cadus 1289+Cadus 1297=Receptor⁻Ligand⁺=(R−L+)

Cadus 1303+Cadus 1297=Receptor⁺Ligand⁺=(R+L+)

Receptor refers to the human C5a receptor.
Ligand refers to human C5a.

Figure 11:
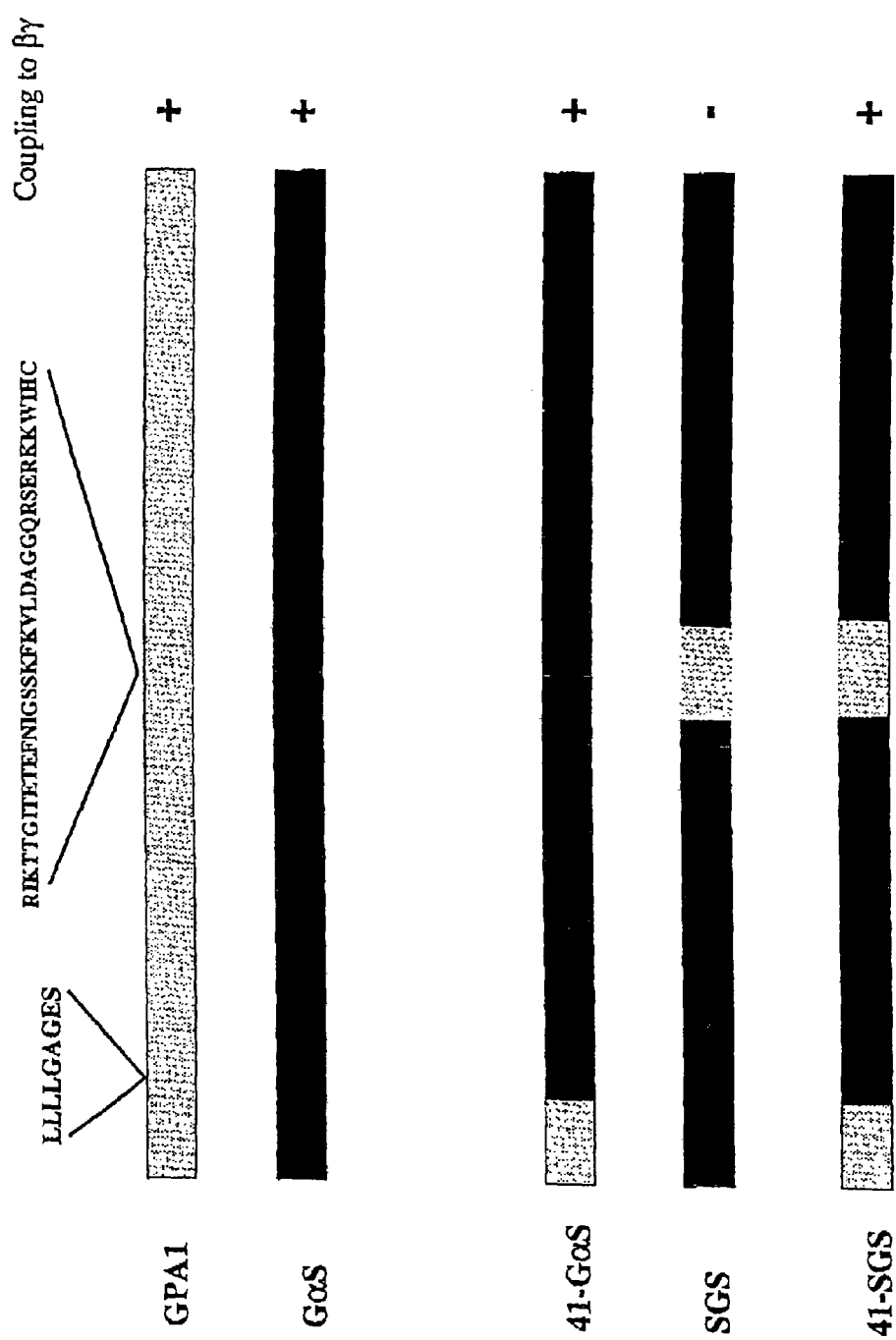

FIG. 11. This Figure schematically describes three hybrids of GPA1 and GαS. The -LLLLGAGES- sequence (SEQ ID NO: 120) demarcated in GPA1 directly follows the non-conserved N-terminal domain of the protein (SEQ ID NO: 135). The longer sequence demarcated in GPA1 encodes the "switch region" believed to be involved in the conformational change that occurs with nucleotide exchange upon receptor activation. 41-Gαs is comprised of the N-terminal 41 amino acids of GPA1 linked to Gαs sequence from which the native N-terminal sequence has been deleted. SGS denotes a molecule comprised of the switch region residues of GPA1 replacing those of Gαs. $GPA_{41}$-SGS includes both the N-terminal and switch region sequences of GPA1 inserted into Gαs. (See Table 6 for the exact sequence junctions used to construct these hybrid proteins).

DETAILED DESCRIPTION OF THE PREFERRED EMBODIMENTS

The present invention contemplates the assaying of peptides, especially when presented in peptide libraries, expressed in genetically engineered yeast cells, for the ability of the peptides to interact with pheromone system proteins and PSP surrogates produced by those yeast cells.

For the purpose of the present invention, an "exogenous" protein is one which sufficiently differs in amino acid sequence from the proteins naturally produced by the yeast cell in question so that its closest cognate is a protein produced by a cell other than a yeast cell. The cell producing this cognate protein may be a microbial cell (other than a yeast cell), a plant cell, or an animal cell. If an animal cell, it may be of invertebrate (e.g., insect or nematode) or of vertebrate (e.g., avian, piscine or mammalian, especially human) origin. A protein is considered to be of, e.g., human origin, regardless of whether it is encoded by the chromosome of a normal human, or by the genome of a virus which infects and replicates in human cells.

An "activator" of a pheromone system protein surrogate is a substance which, in a suitable yeast cell, causes the pheromone system protein surrogate to become more active, and thereby elevates the signal transduced by the native or modified pheromone signal pathway of said cell to a detectable degree. The surrogate may be initially nonfunctional, but rendered functional as a result of the action of the activator, or it may be functional, and the effect of the activator is to heighten the activity of the surrogate. The mode of action of the activator may be direct, e.g., through binding the surrogate, or indirect, e.g., through binding another molecule which otherwise interacts with the surrogate. When the PSP surrogate is a substitute for a pheromone receptor, and the activator takes the place of the pheromone, it is customary to refer to the activator as an agonist of the receptor.

Conversely, an "inhibitor" of a pheromone system protein surrogate is a substance which, in a suitable yeast cell, causes the PSP surrogate to become less active, and thereby reduces the transduced signal to a detectable degree. The reduction may be complete or partial. When the PSP surrogate is a substitute for a pheromone receptor, and the inhibitor competes with the pheromone for binding to the receptor, it is customary to refer to the inhibitor as an "antagonist".

The term "modulator" includes both "activators" and "inhibitors".

A surrogate PSP protein is "functionally homologous" to a yeast protein if, either alone or after being modified by a drug, it is able to perform the function of the yeast PSP, or an analogous function, within the engineered yeast cell. It is not necessary that it be as efficient as the yeast protein, however, it is desirable that it have at least 10% of at least one of the pheromone system-related activities of the yeast protein. Nor is it necessary that it have the same spectrum of action as the yeast protein, e.g., if it is a receptor, it may respond to entirely different ligands than does the endogenous receptor, or to some common ligands and some new ones. The receptors of Table 2 are considered functionally homologous with the yeast pheromone receptors, even though they do not respond to yeast pheromones, and may not couple to the unmodified endogenous G proteins, although they are G protein-coupled receptors. This is considered an "analogous function".

The PSP surrogate may be a protein which must be modified in some way by a drug to be functional. For example, the drug could cause an allosteric change in the PSP surrogate's conformation, or it could cleave off a portion of the surrogate, the balance of the protein then being a functional molecule.

The PSP surrogate may also be one which is functional only if other modifications are made in the yeast cell, e.g., expression of a chimeric G α subunit to interact with an exogenous G protein-coupled receptor.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

"Conservative modifications" are defined as
(a) conservative substitutions of amino acids as hereafter defined; and
(b) single or multiple insertions or deletions of amino acids at the termini, at interdomain boundaries, in loops or in other segments of relatively high mobility.

Preferably, except at the termini, no more than about five amino acids are inserted or deleted at a particular locus, and the modifications are outside regions known to contain binding sites important to activity.

Conservative substitutions are herein defined as exchanges within one of the following five groups:
I. Small aliphatic, nonpolar or slightly polar residues:
  Ala, Ser, Thr (Pro, Gly)
II. Polar, negatively charged residues: and their amides
  Asp, Asn, Glu, Gln
III. Polar, positively charged residues:
  His, Arg, Lys
IV. Large, aliphatic, nonpolar residues:
  Met, Leu, Ile, Val (Cys)
V. Large, aromatic residues:
  Phe, Tyr, Trp Residues Pro, Gly and Cys are parenthesized because they can have special conformational roles. Cys participates in formation of disulfide bonds. Gly imparts flexibility to the chain. Pro imparts rigidity to the chain and disrupts α helices. These residues may be essential in certain regions of the polypeptide, but substitutable elsewhere.

Two regulatory DNA sequences (e.g., promoters) are "substantially homologous" if they have substantially the same regulatory effect as a result of a substantial identity in nucleotide sequence. Typically, "substantially homologous" sequences are at least 50, more preferably at least 80%, identical, at least in regions known to be involved in the desired regulation. Most preferably, no more than five bases are different.

For the purposes of the appended claims, the term "chimeric protein" refers to a protein which is not identical in sequence to either of two patental proteins A and B, but which, when its sequence is aligned with the sequences of A and B, can be seen to borrow features (identically or conservatively) from both parental proteins.

The term "autocrine cell", as used herein, refers to a cell which produces a substance which can stimulate the pheromone system pathway of that cell. Wild-type α and a cells are not autocrine. However a yeast cell which produces both α-factor and α-factor receptor, or both a-factor and a-factor receptor, in functional form, is autocrine. By extension, yeast cells which produce a peptide which is being screened for the ability to activate the pheromone system pathway (e.g., by activating a G protein-coupled receptor) are called "autocrine cells", though it might be more precise to call them "putative autocrine cells". Of course, in a library of such cells, in which a multitude of different peptides are produced, it is likely that one or more of the cells will be "autocrine" in the stricter sense of the term.

Farnesyltransferases

The activity of yeast a-factor requires its farnesylation (mediated by protein farnesyltransferase, comprised of Ram1p and Ram2p), proteolytic cleavage of the C-terminal 3 amino acids of the primary translation product (mediated by an as yet unidentified enzyme), and carboxymethylation of the C-terminal cysteine (mediated by Ste14p). The yeast and mammalian farnesyltransferases are structurally and functionally similar (Gomez R et al., Biochem. J. 289:25-31, 1993; Kohl N E et al., J. Biol. Chem. 266:18884-8, 1991). Sequence homologies exist between the genes encoding the α and β subunits of the yeast farnesyltransferase (RAM2 and RAM1, respectively) and the genes encoding the α and β subunits of the mammalian farnesyltransferase (Kohl N E et al., J. Biol. Chem. 266:18884-8, 1991; Chen W J et al., Cell 66:327-34, 1991). It has been observed that the β subunit of mammalian farnesyltransferase and Ram1p are 37% identical in amino acid sequence (Chen W J et al., Cell 66:327-34, 1991).

The importance of a screen for inhibitors of farneysltransferase is suggested by the facts that mammalian p21ras, a preeminent regulator of the growth and differentiation of mammalian cells that is involved in a variety of cancers, is a substrate for the farnesyltransferase and that farnesylation of p21ras is required for its activity. In fact, a synthetic organic inhibitor of farnesyl protein transferase has been shown to selectively inhibit ras-dependent cell transformation (Kohl et al., Science 260, 1934 (1993). Of the two subunits of farnesyltransferase, the β subunit is a more attractive target for inhibitors, since it is apparently dedicated to farnesylation. The α subunit, in contrast, is shared by geranyl-geranyltransferase I, an enzyme involved in the modification of the Gγ subunits of heterotrimeric G proteins and small molecular weight G proteins of the Rho/Rac family. While the β subunit is dedicated to farnesylation, the mammalian farnesyltransferase has a variety of substrates in addition to p21ras. The effect of inhibitors of the β subunit on the farnesylation of these other substrates, e.g., lamin proteins, transducin-γ and rhodopsin kinase, will be considered in the design and use of potential farnesyltransferase inhibitors.

It has not yet been demonstrated that the homologous mammalian gene will functionally substitute for yeast Ram1p, however, this can be formally tested using ram1 mutants and a vector expressing the mammalian gene encoding the β subunit of the farnesyltransferase. If the mammalian β subunit can function in place of Ram1p, test cells will be both viable (as a result of farnesylation of Ras) and competent for mating (as a result of farnesylation of a-factor).

If the mammalian gene encoding the β subunit of farnesltransferase complements ram1, yeast would provide a test system for the discovery of potential inhibitors of mammalian farneysltransferase. Specifically, MATa yeast tester cells could be exploited that: 1. carry the gene for the β subunit of mammalian farnesyltransferase in lieu of RAM1 ; 2. carry the cam mutation that renders the strains resistant to loss of Ras function in the presence of cAMP; 3. respond to a-factor which they export by virtue of heterologous expression of Ste3p; 4. respond to autocrine a-factor such that they cannot grow on media containing galactose. The latter characteristic will require expression of GAL1 under the control of a pheromone-responsive promoter and cells engineered to contain mutated GAL7 or GAL10 genes. Expression of GAL1 is toxic in the presence of galactose in strains which contain mutations in either the GAL7 or GAL10 genes. Signaling through the pheromone response pathway would render cells so engineered galactose-sensitive. Exposure of such strains to compounds which inhibit the β subunit of farneysltransferase will confer upon these cells the ability to grow on media containing galactose and cAMP.

If the mammalian gene encoding the β subunit of farnesyltransferase (and all modified versions of the gene) fails to complement ram1, we may use the wild-type Ram1p as a surrogate target for potential effectors of mammalian farnesyltransferase. Specifically, we will use as tester cells MATa yeast strains that: 1. carry the cam mutation that renders the strains resistant to loss of RAS function in the presence of cAMP; 2. respond to a-factor which they export by virtue of heterologous expression of Ste3p; 3. respond to autocrine a-factor such that they cannot grow on media containing galactose. Exposure of such strains to compounds which inhibit the β subunit of farnesyltransferase will confer upon these cells the ability to grow on media containing galactose and cAMP.

In the strategies outlined above, it is desirable to discriminate inhibitors of farnesyltransferase from compounds that either directly block the negative response to a-factor, e.g. by interfering with the interaction of the Ste4-Ste18 complex with its effector, or by blocking the production of a-factor by a mechanism that does not involve farnesyltransferase. Controls would identify such false positives. Candidate agents will be tested on a MATa strain that is engineered to secrete α-factor and to respond to the secreted a-factor by failing to grow on galactose-containing media, as in the negative selection scheme outlined above. The strain will express wild type Ram1p. Any agent that enables these cells to grow on media containing galactose and cAMP will not be acting as an inhibitor of farnesyltransferase.

Candidate compounds which pass the foregoing test may act by targeting Ste14p, Ste6p, or other proteins involved in the maturation and export of a-factor, rather than farneysltransferase. (Note, however, that compounds that inhibit processes critical to cell survival will not give rise to false positives. For example, since the protease responsible for the endoproteolytic removal of the C-terminal tripeptide of the a-factor precursor likely participates in the processing of Gg and members of the Rho/Rac family of proteins, inhibitors of this enzyme may not permit growth of the tester cells) Of the proteins involved in the production of a-factor, only the farnesyltransferase is also a major determinant of RAS function. Due to this effect, ram1 mutants are defective for growth at 30° C. and completely unable to grow at 37 (He B et al., Proc Natl Acad Sci 88:11373-7, 1991). Tester cells (described above) can be grown in the presence of a candidate inhibitor on galactose-containing media±cAMP. If the test compound inhibits farnesyltransferase, cells will be capable of growth on galactose±cAMP but not on galactose in the absence of cAMP. This difference may be most obvious at 37°. If, on the other hand, the test compound inhibits other proteins involved in a-factor production, cells will grow on galactose-containing media regardless of the presence or absence of cAMP.

Compounds which pass the above tests are likely inhibitors of farnesyltransferase. This can be confirmed and their potencies determined with direct in vitro enzyme assays. Note that the strategies outlined will identify farnesyltransferase inhibitors which affect Ramlp. Agents which block Ram2p would likely fail to grow under all conditions. Indeed, ram2 null mutations are lethal (He B et al., Proc Natl Acad Sci 88:11373-7, 1991), perhaps due to the fact that Ram2p also functions as a component of geranylgeranyltransferase I.

Carboxymethyltransferases

In yeast, methylation of the C-terminal amino acid of a-factor, Ras proteins, and presumably Rho/Rac proteins is catalyzed by Ste14p. Although MATa ste14 mutants are unable to mate, reflecting the requirement of carboxymethylation for the activity of a-factor, ste14 disruptions are not lethal and do not affect the rate of cell proliferation. Carboxymethylation appears to be dispensable for the function of Ras proteins and Ste18p (the yeast homologue of the Gγ subunit). Although Ras function in yeast can apparently tolerate the absence of carboxymethyl modification, it is nonetheless possible that inhibitors of mammalian methyltransferases could alter the activity of mammalian p21ras.

It could be determined if yeast ste14 mutations can be complemented by the homologous mammalian gene, or a modified version of it. One would use an episomal vector to express the mammalian gene encoding the methyltransferase in yeast that are genotypically ste14. The strain would be a modified MATa strain that expresses the a-factor receptor in lieu of the normal a-factor receptor and that contains an integrated fus1-HIS3 construct, so that the a-factor secreted by the cell confers autocrine growth on histidine-deficient media. If the mammalian methyltransferase can function in place of Ste14p, the tester cells will be capable of mating. That is, the mammalian methyltransferase will permit synthesis of active a-factor in ste14 mutants.

If the mammalian gene encoding the methyltransferase will complement ste14, tester strains can be constructed to test for potential inhibitors of mammalian methyltransferase. In one embodiment, tester MATa yeast strains will: 1. carry a mammalian carboxymethyltransferase gene in lieu of STE14; 2. respond to a-factor which they export by virtue of heterologous expression of Ste3p; 3. respond to autocrine a-factor such that they cannot grow on media containing galactose as in the negative GAL1 selection scheme outlined above. Exposure of such strains to compounds which inhibit the methyltransferase will confer upon these cells the ability to grow on media containing galactose.

It is desirable to discriminate inhibitors of carboxymethyltransferase activity from compounds that either directly block the negative response to a-factor, e.g. by interfering with the interaction of the Ste4-Ste18 complex with its effector, or block the production of a-factor by a mechanism that does not involve methyltransferase. The following control experiments will identify such false positives. Candidate inhibitors will be tested on a MATa strain that is engineered to secrete a-factor and to respond to the secreted a-factor by failing to grow on galactose-containing media. Any agent that enables these cells to grow on media containing galactose will be not be acting as an inhibitor of carboxymethyltransferase. Candidate compounds which pass the foregoing test may be targeting the carboxymethyltransferase, farnesyltransferase, Ste6p, or other proteins involved in the maturation and export of a-factor. In order to discriminate the target of the compounds, a combination of in vitro biochemical and in vivo genetic assays can be applied: both the carboxymethyltransferase and the farnesyltransferase can be assayed in vitro to test the effect of the candidate agent. Furthermore, if the target is Ste14p its overexpression on high-copy plasmids should confer resistance to the effect of the compound in vivo.

Proteases

Mature yeast α-factor is a thirteen amino acid peptide that is derived from a polyprotein precursor in much the same manner as mature mammalian melanocyte-stimulating hormone (MSH) or calcitonin are derived from precursor polyproteins. Two genes in the yeast genome encode prepro-α-factor, MFα1 and MFα2. MFα1 encodes a precursor polypeptide containing four copies of mature α-factor embedded in a polypeptide of the following structure: hydrophobic pre-sequence/hydrophilic pro-sequence/α-factor/α-factor/α-factor/α-factor. MFα2 encodes a polyprotein precursor of a similar structure containing only two copies of mature α-factor.

Pre-pro-α-factor is synthesized in the cytoplasm and is then transported from the cytoplasm to the endoplasmic reticulum and then to the Golgi along the classical secretory pathway of S. cerevisiae. The signal sequence of prepro-α-factor is cleaved during transit into the ER by signal peptidase and asparagine-linked oligosaccharides are added (in the ER) and modified (in the Golgi) on the pro-segment of the precursor as it transits the secretory pathway. Once in the Golgi, three distinct proteolytic processing events occur. First, the Kex2 protease cleaves at dibasic residues (-KR-) near the amino terminus of each α-factor repeat. Kex2 is homologous to the subtilisin-like endoproteases PC2 and PC1/PC3 involved in prohormone processing in mammalian cells (Smeekens and Steiner 1990; Nakayama et al. 1991). Additional mammalian Kex2-like processing endoproteases include PACE, isolated from a human hepatoma, PC4, expressed in testicular germ cells and PC6, a candidate protease for the processing of gastrointestinal peptides (Barr et al. 1991; Nakayama et al. 1992; Nakagawa et al. 1993). It appears that Kex2-like proteins comprise a large family of tissue-specific endoproteases in mammalian cells.

Once Kex2 has released the immature α-factor peptides, two additional proteases act to complete processing. Kex1 is a specific carboxypeptidase that removes the carboxy-terminal-KR remaining after cleavage by Kex2. Like its mammalian counterparts carboxypeptidases B and E, Kex1 is highly specific for peptide substrates with carboxy-terminal basic residues. The final proteolytic processing event that occurs is the removal of the spacer dipeptides at the amino terminus of each pro-α-factor peptide. This is accomplished by the product of the STE13 gene, dipeptidyl aminopeptidase A. This enzyme is a type IV dipeptidyl aminopeptidase: it is capable of cleaving on the carboxyl side of either -x-A- or -x-P- sites in vitro.

Other type IV dipeptidyl aminopeptidases are believed to be active in the processing of a variety of pre-peptides in animal cells (Kreil 1990). In addition, functional similarity has been proved between yeast Kex1 and Kex2 and their mammalian counterparts in that both yeast enzymes will proteolytically cleave endogenous precursors when expressed in mammalian cells deficient in the native enzyme (Thomas et al. 1988, 1990). It appears likely, then, that mammalian homologs of the yeast proteases Kex1, Kex2 and Ste13p, when expressed in yeast, will function to process a synthetic α-factor pheromone precursor bearing appropriate cleavage sites. Human proteases that may so function in yeast include PC2 and PC1/PC3 (or other Kex2 homologs), carboxypeptidases B and E (Kex1 homologs) and type IV dipeptidyl aminopeptidases (Ste13p homologs).

Yeast would provide a facile assay system for the discovery of inhibitors of proteases able to process synthetic α-factor. The yeast could be engineered to express both the potential inhibitor and the exogenous protease, and, preferably, not the latter's yeast cognate.

Furthermore, this means of exploiting yeast pheromone processing to identify protease inhibitors can be expanded to encompass any protease that can be expressed to function in yeast, provided an appropriate cleavage recognition site is included in a synthetic α-factor precursor. In the latter approach, novel proteolytic activities will be added to yeast; these enzymes will substitute for proteases in the α-factor maturation pathway but will not be "catalytic homologues" of Kex1, Kex2 or Ste13p. Production of mature α-factor will become dependent on the activity of the novel protease through removal of the recognition site(s) for a selected yeast enzyme from a synthetic MFα gene and insertion of the recognition sequence for the novel protease(s).

Enzymes for which inhibitors could be identified via this strategy include, by way of example, HIV-1 protease or other virally encoded proteases involved in the maturation of infectious particles; neutrophil elastase believed to be involved in pulmonary disease and inflammatory bowel disease; Factor Xa involved in thrombin processing and clotting disorders; and CD26, a dipeptidyl peptidase IV and putatively the second receptor for HIV-1 on CD4[+] cells. In addition, metalloproteinases (e.g. collagenase) and serine proteases involved in tissue invasion by tumor cells and in metastasis would be suitable therapeutic targets. In support of this, it has been demonstrated that administration of tissue-derived inhibitors of metalloproteinases results in decreased metastasis in animal models (Schultz et al. 1988). Collagenases have also been implicated in the destruction of connective tissue which accompanies inflammatory processes like rheumatoid arthritis.

The use of the present invention to screen for modulators of prohormone convertase PC1 is described in Example 8.

Exogenous ABC Transporters

The majority of proteins destined for transport to the extracellular environment proceed through a secretory pathway that includes translation initiation in the cytoplasm, transport to the lumen of the endoplasmic reticulum, passage through the Golgi to secretory vesicles and subsequent exit from cells. Other proteins leave the cell by an alternative mechanism, which involves mediation by an "ABC transporter". The ABC transporters form a family of evolutionarily conserved proteins, share a similar overall structure, and function in the transport of large and small molecules across cellular membranes (Higgins 1992). The characteristic component of members of this protein family is a highly conserved sequence that binds ATP (Higgins et al., 1986; Hyde et al.

1990); these intrinsic membrane proteins are ATPases, deriving energy from the hydrolysis of that nucleotide to effect the transport of molecules. This family includes over 50 prokaryotic and eukaryotic proteins: transporters of amino acids, sugars, oligosaccharides, ions, heavy metals, peptides, or other proteins belong to this superfamily. Representative transmembrane transporters are included in Table 1. Typically, ABC transporters use the energy of ATP hydrolysis to pump substrate across a cell membrane against a concentration gradient. Some import substrate, others export it. See Higgins, *Ann. Rev. Cell, Biol.*, 8:67-113 (1992).

The prototypical structure of an ABC transporter includes four membrane-associated domains: two hydrophobic, putative membrane-spanning sequences, each predicted to traverse the membrane six times, and two nucleotide binding domains that couple ATP hydrolysis to transport. In prokaryotes, the domains of an ABC transporter are often present on separate polypeptides. various permutations of domain fusions have been described: the *E. coli* iron hydroxamate transporter contains the two membrane-spanning domains in a single polypeptide and the ribose transporter of the same organism bears two nucleotide-binding domains on one molecule. The major histocompatibility complex (MHC) peptide transporter is composed of two polypeptides, Tap1 and Tap2. The N-terminus of each protein contains a hydrophobic membrane-spanning domain while the C-terminus contains an ATP-binding sequence. Together Tap1 and Tap2 form a functional complex. The heavy metal tolerance protein, HMT1, expressed in the fission yeast *Schizosaccharomyces pombe*, consists of a polypeptide containing a single hydrophobic domain and a C-terminal ATP-binding sequence (Ortiz et al. 1992). It may be that the HMT1 transporter functions as a homodimer. The *Saccharomyces cerevisiae* Ste6 a-factor transporter is expressed as a single polypeptide containing two membrane-spanning domains and two nucleotide-binding domains. When Ste6 is expressed as two half-molecules, the protein complex which apparently forms retains function at a level greater than 50 that of the wild type, single polypeptide (Berkower and Michaels 1991). In other eukaryotic ABC transporters, including Mdr1, CFTR and MRP, the four domains are also contained within a single polypeptide. Thus, the ABC transporter may be a single multidomain polypeptide, or it may comprise two or more polypeptides, each providing one or more domains.

In general, transporters contain six transmembrane segments per each hydrophobic domain, for a total of twelve segments. The minimum number of transmembrane segments required for formation of a translocation complex appears to be 10. Thus the histidine transporter of *S. typhimurium* lacks an N-terminal transmembrane segment from each of its hydrophophic domains and therefore contains five transmembrane segments per domain (Higgins et al., Nature 298, 723-727 (1982). The MalF protein of the *E. coli* maltose transporter contains an N-terminal extension of hydrophobic sequence which bears two additional transmembrane segments, bringing the total for this hydrophobic domain to 8 (Overduin et al. 1988) . The N-terminal extension can be deleted, however, without loss of function of this transporter (Ehrmann et al. 1990). Although the number of segments required for formation of a functional translocator is suggested by these studies, there exists no data on the precise structure of the transmembrane segments themselves. These sequences are assumed to have an α-helical form, but this has not been proven and the structure of the entire translocation complex within the plasma membrane remains to be elucidated.

In order to span the lipid bilayer, a minimum of 20 amino acids is required and sequences believed to form transmembrane segments have been identified using hydrophobicity scales. Hydrophobicity scales assign values to individual amino acid residues indicating the degree of hydrophobicity of each molecule (Kyte and Doolittle 1982; Engleman et al. 1986). These values are based on experimental data (solubility measurements of amino acids in various solvents, analysis of side chains within soluble proteins) and theoretical considerations, and allow prediction of secondary structure in novel sequence with reasonable accuracy. Analysis using hydrophobicity measurements indicates those stretches of a protein sequence which have the hydrophobic properties consistent with a transmembrane helix.

With a few exceptions, there is little or no significant amino acid sequence similarity between the transmembrane domains of two different transporters. This lack of sequence similarity is not inconsistent with the apparent function of these hydrophobic domains. While these residues must be capable of forming the hydrophobic α-helical structures believed to transverse the plasma membrane, many amino acid residues are hydrophobic and can contribute to the formation of an α-helix.

Considerable, if as yet inexplicable, sequence similarity has been detected in comparisons of the transmembrane domains of the yeast STE6, human MDR and *E. coli* HlyB hemolysin transporters [Gros et al., Cell 47, 371 (1986); McGrath and Varchavsky, Nature 340, 400 (1989); Kuchler et al., EMBO J. 8, 3973 (1989)]. Other sequence similarities can be explained by gene duplication, as in the case of the transmembrane domains of rodent P-glycoproteins (Endicott et al. 1991). The transmembrane domain of the histidine transporter of *S. typhimurium* bears homology to that of the octopine uptake system of *Agrobacterium tumefaciens*, the latter two transporters translocate chemically similar substrates (Valdiva et al. 1991).

Study of mutant transport proteins has pointed to a role for the transmembrane sequences in the recognition of substrate. Thus maltose transporters in *E. coli* which gain the ability to translocate p-nitrophenyl-α-maltoside bear mutations in the transmembrane domain (Reyes et al. 1986). A mutation in transmembrane segment 11 of MDR has been shown to change the substrate specificity of that transporter (Gros et al. 1991) and mutation of charged residues in the transmembrane domain of CFTR changes its ion selectivity (Anderson et al. 1991).

Some aspects of the involvement of extramembrane loop sequences in transport function are being elucidated. In a number of bacterial transporters a short conserved motif is present on the cytoplasmic loop which connects transmembrane segments 4 and 5 [Dassa and Hofnung (1985)]. It has been hypothesized that this sequence interacts with the ATP-binding domains of these transport proteins; mutation of this conserved sequence will abolish transport function (Dassa 1990). Cytoplasmic loops may also be involved in substrate recognition. Thus the sequences following transmembrane segments 7 and 12 of the yeast a-factor transporter resemble sequences in the a-factor receptor, Ste3p, and may interact with the pheromone substrate (Kuchler et al. 1989). In fact, mutations in the cytoplasmic loops are known to alter the substrate specificity of a given transporter. The G185V mutation of human MDR, located in the loop between transmembrane segments 2 and 3, alters the interaction of that transporter with vinblastine and colchicine (Choi et al. 1988).

The ATP-binding domains are about 200 amino acids long, and domains from different transporters typically have a sequence identity of 30-50%. The conserved sequences include the "Walker motifs" which are associated with many nucleotide binding proteins. Walker, et al., EMBO J. 1:945-951 (1982).

Sequence conservation extends over the length of the ATP-binding domain, not being limited to the Walker motifs. Furthermore, the ATP-binding domains of a single transporter exhibit greater sequence identity to one another than to the domains from two different transporters. Not all proteins containing a conserved ATP-binding domain are involved in transport, however. The cytoplasmic enzyme UvrA functions in DNA repair and the EF-3 protein of yeast is an elongation factor. Yet both proteins contain ATP-binding cassettes identifiable by sequence comparison.

ATP-binding domains are highly hydrophilic and, in the case of transporters, appear to reside at the cytoplasmic face of the membrane, anchored there via an association with the membrane-spanning domain of these proteins. The points of interaction between the transmembrane and ATP-binding domains have not been experimentally determined. Models of the structure of the nucleotide binding domain indicate that loop sequences may extend from the core of the structure to interface with the hydrophilic sequences which transverse the membrane (Hyde et al. 1990; Mimura et al. 1991). The two structural models, one based on adenylate cyclase and the other on ras p21 structure, predict a core nucleotide binding fold composed of five β-sheets with the Walker A motif (a glycine-rich loop) positioned to interact with ATP during hydrolysis. In addition, loop structures (two loops in one model, one large loop in the other) are predicted to extend from the core to couple the ATP-binding domain to other domains of the transporter. The coupling sequences transmit, most likely through conformational change, the energy of ATP hydrolysis to those portions of the molecule which are involved in transport.

Ste6 function is required for mating but the protein is not necessary for yeast survival (Wilson and Herskowiz 1984; Kuchler et al. 1989; McGrath and Varshavsky 1989). Ste6 is structurally homologous to the mammalian MDRs. Furthermore, it has been demonstrated that two mammalian MDR proteins, murine Mdr3 and human Mdr1, will substitute functionally for the yeast transporter in cells deleted for STE6 (Raymond et al. 1992; Kuchler and Thorner 1992). Yeast strains deleted for STE6 serve as a starting point for the design of screens to discover compounds that modulate the function of exogenous ABC transporters.

Two different yeast screens can be used to identify modulators of ABC transporter function. In the first instance, a mammalian protein that transports a-factor will serve as a target for potential inhibitors of transporter function. Thus, a yeast strain will be engineered to express a functional transporter, e.g. mammalian MDR1, which substitutes for the yeast Ste6 protein in the transport of a-factor. Furthermore, this strain will be engineered to respond in autocrine fashion to a-factor: e.g., so that the cells will be unable to grow on media containing galactose. This negative selection will depend on the expression of the GAL1 gene under the control of a pheromone-responsive promoter in a strain background which includes mutated versions of the GAL7 or GAL10 genes. Expression of GAL1 in the presence of galactose in such a strain background is toxic to cells. In the absence of a-factor transport, signaling down the pheromone response pathway would cease as would the consequent expression of the toxic gene. Cell growth in the presence of a test compound, or upon expression of a specific random peptide, would signal inhibition of transport function and the identification of a potential therapeutic.

In addition to inhibitors of MDR, compounds may be identified which interfere with the interaction of a-factor with the a-factor receptor. Such compounds can be discriminated by their inhibition of a-factor-induced growth arrest in a wild type Matα strain. Compounds may also impact at other points along the pheromone response pathway to inhibit signaling and these compounds will prevent signal transduction in a wild type Matα strain.

In a second screen, a mutant heterologous transporter (e.g., mutant CFTR) that is initially incapable of transporting a-factor or an a-factor-like peptide can be expressed in autocrine yeast deleted for endogenous Ste6. The cells will be capable of an autocrine response to the a-factor which those cells produce. Thus a pheromone-responsive promoter will control expression of a gene that confers an ability to grow in selective media. Such cells will permit identification of compounds which correct defects in the transporter and permit it to function in the export of pheromone analogues to the extracellular space. In this way, therapeutic peptides or other classes of chemical compounds could be identified which stabilize a mutant protein and allow normal processing, transport, localization to the plasma membrane and function. This strategy, if successful, may eliminate the need to "replace" some mutant genes with normal sequence, as envisioned in gene therapies, by recovering the function of mutant proteins through the correction of processing and/or localization defects.

In addition to "activators" of the mutant transporter, compounds may also be identified which are capable of initiating signalling from the a-factor receptor in the absence of transport by the endogenously expressed pheromone. These compounds will be distinguished by their ability to cause growth arrest in a wild type Matα strain. Compounds may also impact at other points along the pheromone pathway and can be discerned via an ability to initiate signalling in a wild type Matα strain in the absence of a-factor.

In a preferred embodiment, the exogenous protein produced by the yeast cells is one of the exogenous ABC transporters listed in Table 1.

Exoqenous G Protein Coupled Receptors

In some instances, for a drug to cure a disease or alleviate its symptoms, the drug must be delivered to the appropriate cells, and trigger the proper "switches." The cellular switches are known as "receptors." Hormones, growth factors, neurotransmitters and many other biomolecules normally act through interaction with specific cellular receptors. Drugs may activate or block particular receptors to achieve a desired pharmaceutical effect. Cell surface receptors mediate the transduction of an "external" signal (the binding of a ligand to the receptor) into an "internal" signal (the modulation of a cytoplasmic metabolic pathway).

In many cases, transduction is accomplished by the following signaling cascade:

An agonist (the ligand) binds to a specific protein (the receptor) on the cell surface.
As a result of the ligand binding, the receptor undergoes an allosteric change which activates a transducing protein in the cell membrane.
The transducing protein activates, within the cell, production of so-called "second messenger molecules."
The second messenger molecules activate certain regulatory proteins within the cell that have the potential to "switch on" or "off" specific genes or alter some metabolic process.

This series of events is coupled in a specific fashion for each possible cellular response. The response to a specific ligand may depend upon which receptor a cell expresses. For instance, the response to adrenalin in cells expressing α-adrenergic receptors may be the opposite of the response in cells expressing β-adrenergic receptors.

The above "cascade" is idealized, and variations on this theme occur. For example, a receptor may act as its own transducing protein, or a transducing protein may act directly on an intracellular target without mediation by a "second messenger".

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein.

The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to receptor, the receptor changes conformation and this alters its interaction with the G protein. This spurs the α subunit to release GDP, and the more abundant nucleotide guanosine tri-phosphate (GTP), replaces it, activating the G protein. The G protein then dissociates to separate the α subunit from the still complexed beta and gamma subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Gα converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the a subunit, several different β and γ structures have been reported. There are, additionally, several different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors. Examples include receptors cloned by Neote et al. Cell 72, 415 (1993); Kouba et al. FEBS Lett. 321, 173 (1993); Birkenbach et al. J. Virol. 67, 2209 (1993).

The "exogenous G protein-coupled receptors" of the present invention may be any G protein-coupled receptor which is exogenous to the wild-type yeast cell which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Suitable receptors include, but are not limited to, dopaminergic, muscarinic cholinergic, α-adrenergic, β-adrenergic, opioid (including delta and mu), cannabinoid, serotoninergic, and GABAergic receptors. Other suitable receptors are listed in Table 2. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed in Table 2. Thus, the gene would be operably linked to a promoter functional in yeast and to a signal sequence functional in yeast. Suitable promoters include Ste2, Ste3 and gal10. Suitable signal sequences include those of Ste2, Ste3 and of other genes which encode proteins secreted by yeast cells. Preferably, the codons of the gene would be optimized for expression in yeast. See Hoekema et al., Mol. Cell. Biol., 7:2914-24 (1987); Sharp, et al., 14:5125-43 (1986).

The homology of STRs is discussed in Dohlman et al., Ann. Rev. Biochem., 60:653-88 (1991). When STRs are compared, a distinct spatial pattern of homology is discernable. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

It is conceivable that a foreign receptor which is expressed in yeast will functionally integrate into the yeast membrane, and there interact with the endogenous yeast G protein. More likely, either the receptor will need to be modified (e.g., by replacing its V-VI loop with that of the yeast STE2 or STE3 receptor), or a compatible G protein should be provided.

If the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible.

Preferably, the yeast genome is modified so that it is unable to produce the endogenous a- and α-factor receptors in functional form. Otherwise, a positive assay score might reflect the ability of a peptide to activate the endogenous G protein-coupled receptor, and not the receptor of interest.

G Protein

When the PSP surrogate is an exogenous G protein-coupled receptor, the yeast cell must be able to produce a G protein which is activated by the exogenous receptor, and which can in turn activate the yeast effector(s). It is possible that the endogenous yeast Gα subunit (e.g., GPA) will be sufficiently homologous to the "cognate" Gα subunit which is natively associated with the exogenous receptor for coupling to occur. More likely, it will be necessary to genetically engineer the yeast cell to produce a foreign Gα subunit which can properly interact with the exogenous receptor. For example, the Gα subunit of the yeast G protein may be replaced by the Gα subunit natively associated with the exogenous receptor.

Dietzel and Kurjan, Cell, 50:1001 (1987) demonstrated that rat Gαs functionally coupled to the yeast Gβγ complex. However, rat Gαi2 complemented only when substantially overexpressed, while Gα0 did not complement at all. Kang, et al., Mol. Cell. Biol., 10:2582 (1990). Consequently, with some foreign Gα subunits, it is not feasible to simply replace the yeast Gα.

If the exogenous G protein coupled receptor is not adequately coupled to yeast Gβγ by the Gα subunit natively associated with the receptor, the Gα subunit may be modified to improve coupling. These modifications often will take the form of mutations which increase the resemblance of the Gα subunit to the yeast Gα while decreasing its resemblance to the receptor-associated Gα. For example, a residue may be changed so as to become identical to the corresponding yeast Gα residue, or to at least belong to the same exchange group of that residue. After modification, the modified Gα subunit might or might not be "substantially homologous" to the foreign and/or the yeast Gα subunit.

The modifications are preferably concentrated in regions of the Gα which are likely to be involved in Gβγ binding. In some embodiments, the modifications will take the form of replacing one or more segments of the receptor-associated Gα with the corresponding yeast Gα segment(s), thereby forming a chimeric Gα subunit. (For the purpose of the appended claims, the term "segment" refers to three or more consecutive amino acids.) In other embodiments, point mutations may be sufficient.

This chimeric Gα subunit will interact with the exogenous receptor and the yeast Gβγ complex, thereby permitting signal transduction. While use of the endogenous yeast Gβγ is preferred, if a foreign or chimeric Gβγ is capable of transducing the signal to the yeast effector, it may be used instead.

Gα Structure

We will now review information regarding Gα structure which is relevant to the design of modified Gα subunits.

In Table 5, part A, the amino terminal 66 residues of GPA1 are aligned with the cognate domains of human Gαs, Gαi2, Gαi3 and Gα16. In part B, we present alignment of the amino-terminal 66 residues of GPA1$_{41}$-Gα chimeras. In the GPA$_{41}$-Gα hybrids, the amino terminal 41 residues (derived from GPA1) are identical, end with the sequence -LEKQRD-KNE-(SEQ ID NO: 121) and are underlined for emphasis. All residues following the glutamate (E) residue at position 41 are contributed by the human Gα subunits, including the consensus nucleotide binding motif -GxGxxG- (SEQ ID NO: 122). Periods in the sequences indicate gaps that have been introduced to maximize alignments in this region. Codon bias is mammalian. For alignments of the entire coding regions of GPA1 with Gαs, Gαi, and GαO, Gαq and Gαz, see Dietzel and Kurjan (1987) and Lambright, et al. (1994). Additional sequence information is provided by Mattera, et al. (1986), Bray, et al. (1986) and Bray, et al. (1987).

The sequences are identified as follows: GPA1 (SEQ ID NO:82); Gαs (SEQ ID NO:83); Gαi2 (SEQ ID NO:84); Gαi3 (SEQ ID NO:85); Gα16 (SEQ ID NO:86); GPA41-Gαs (SEQ ID NO:87); GPA41-Gαi2 (SEQ ID NO:88); GPA41-Gαi3 (SEQ ID NO: 89); and GPA41-Gα16 (SEQ ID NO:90).

The gene encoding a G protein homolog of S. cerevisiae was cloned independently by Dietzel and Kurjan (1987) (SCG1) and by Nakafuku, et al. (1987) (GPA1). Sequence analysis revealed a high degree of homology between the protein encoded by this gene and mammalian Gα. GPA1 encodes a protein of 472 amino acids, as compared with approximately 340-350 a.a. for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to Gαs (33% identity, or 51% with conservative substitutions) (Nakafuku, et al. 1987).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the αβ fold of ras proteins and the protein systhesis elongation factor EF-Tu. This highly conserved guanine nucleotide-binding domain consists of a six-stranded β sheet surrounded by a set of five α-helices. It is within these β sheets and α helices that the highest degree of conservation is observed among all Gα proteins, including GPA1. The least sequence and structural homology is found in the intervening loops between the β sheets and α helices that define the core GTPase domain. There are a total of four "intervening loops" or "inserts" present in all Gα subunits. In the crystal structures reported to date for the GDP- and GTPγS-liganded forms of bovine rod transducin (Noel, et al. 1993; Lambright, et al. 1994), the loop residues are found to be outside the core GTPase structure. Functional roles for these loop structures have been established in only a few instances. A direct role in coupling to phosphodiesterase-γ has been demonstrated for residues within inserts 3 and 4 of Gαt (Rarick, et al. 1992; Artemyev, et al. 1992), while a "GAP-like". activity has been ascribed to the largely α-helical insert 1 domain of GαS (Markby, et al. 1993).

While the amino- and carboxy-termini of Gα subunits do not share striking homology either at the primary, secondary, or tertiary levels, there are several generalizations that can be made about them. First, the amino termini of Gα subunits have been implicated in the association of Gα with Gβγ complexes and in membrane association via N-terminal myristoylation. In addition, the carboxy-termini have been implicated in the association of Gαβγ heterotrimeric complexes with G protein-coupled receptors (Sullivan, et al. 1987; West, et al. 1985; Conklin, et al. 1993). Data in support of these generalizations about the function of the N-terminus derive from several sources, including both biochemical and genetic studies.

As indicated above, there is little if any sequence homology shared among the amino termini of Gα subunits. The amino terminal domains of Gα subunits that precede the first β-sheet (containing the sequence motif -LLLLGAGESG (SEQ ID NO: 123); see Noel, et al. (1993) for the numbering of the structural elements of . Gα subunits) vary in length from 41 amino acids (GPA1) to 31 amino acids (Gαt). Most Gα subunits share the consensus sequence for the addition of myristic acid at their amino termini (MGxxxS-(SEQ ID NO: 124)), although not all Gα subunits that contain this motif have Myristic acid covalently associated with the glycine at position 2 (speigel, et al. 1991). The role of this post-translational modification has been inferred from studies in which the activity of mutant Gα subunits from which the consensus sequence for myristoylation has been added or deleted has been assayed (Mumby, et al. 1990; Linder, et al. 1991; Gallego, et al. 1992). These studies suggest two roles for N-terminal myristoylation. First, the presence of amino-terminal myristic acid has in some cases been shown to be required for association of Gα subunits with the membrane, and second, this modification has been demonstrated to play a role in modulating the association of Gα subunits with Gβγ complexes. The role of myristoylation of the GPA1 gene product is, at present, unknown.

In other biochemical studies aimed at examining the role of the amino-terminus of Gα in driving the association between Gα and Gβγ subunits, proteolytically or genetically truncated versions of Gα subunits were assayed for their ability to associate with Gβγ complexes, bind guanine nucleotides and/ or to activate effector molecules. In all cases, Gα subunits with truncated amino termini were deficient in all three functions (Graf, et al. 1992; Journot, et al. 1990; and Neer, et al. 1988). Slepak, et al. (1993) reported a mutational analysis of the N-terminal 56 a.a. of mammalian Gαo expressed in *Escherichia coli*. Molecules with an apparent reduced ability to interact with exogenously added mammalian Gβγ were identified in the mutant library. As the authors pointed out, however, the assay used to screen the mutants—the extent of ADP-ribosylation of the mutant Gα by pertussis toxin—was not a completely satisfactory probe of interactions between Gα and Gβγ. Mutations identified as inhibiting the interaction of the subunits, using this assay, may still permit the complexing of Gα and Gβγ while sterically hindering the ribosylation of Gα by toxin.

Genetic studies examined the role of amino-terminal determinants of Gα in heterotrimer subunit association have been carried out in both yeast systems using GPA1-mammalian Gα hybrids (Kang, et al. 1990) and in mammalian systems using Gαi/Gαs hybrids (Russell and Johnson 1993). In the former studies, gene fusions, composed of yeast-GPA1 and mammalian Gα sequences were constructed by Kang, et al. (1990) and assayed for their ability to complement a gpa1 null phenotype (i.e., constitutive activation of the pheromone response pathway) in *S. cerevisiae*. Kang, et al. demonstrated that wild type mammalian Gαs, Gαi but not Gαo proteins are competent to associate with yeast Gβγ and suppress the gpa1 null phenotype, but only when overexpressed. Fusion proteins containing the amino-terminal 330 residues of GPA1 sequence linked to 160, 143, or 142 residues of the mammalian Gαs, Gαi and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpa1 null mutation in a growth arrest assay, and were additionally able to inhibit α-factor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpa1 null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ subunits in a species-restricted manner.

Hybrid Gαi/Gαs subunits have been assayed in mammalian expression systems (Russell and Johnson 1993). In these studies, a large number of chimeric Gα subunits were assayed for an ability to activate adenylyl cyclase, and therefore, indirectly, for an ability to interact with Gβγ (i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the β1 sheet identified in the crystal structure of Gαt (see Noel, et al. 1993 and Lambright, et al. 1994) are involved in determining the state of activity of the heterotrimer by (1) driving association/dissociation between Gα and Gβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs. resulted in constitutive activation of the chimeric proteins (i.e., a loss of receptor-dependent stimulation of Gαβγ dissociation and effector activation).

Construction of Chimeric Gα Subunits.

In designing Gα subunits capable of transmitting, in yeast, signals originating at mammalian G protein-coupled receptors, two general desiderata were recognized. First, the subunits should retain as much of the sequence of the native mammalian proteins as possible. Second, the level of expression for the heterologous components should approach, as closely as possible, the level of their endogenous counterparts. The results described by King, et al. (1990) for expression of the human β2-adrenergic receptor and Gαs in yeast, taken together with negative results obtained by Kang, et al. (1990) with full-length mammalian Gα subunits other than Gαs, led us to the following preferences for the development of yeast strains in which mammalian G protein-coupled receptors could be linked to the pheromone response pathway.

1. Mammalian Gα subunits will be expressed using the native sequence of each subunit or, alternatively, as minimal gene fusions with sequences from the amino terminus of GPA1 replacing the homologous residues from the mammalian Gα subunits.
2. Mammalian Gα subunits will be expressed from the GPA1 promoter either on low copy plasmids or after integration into the yeast genome as a single copy gene.
3. Endogenous Gβγ subunits will be provided by the yeast STE4 and STE18 loci.

Site-Directed Mutagenesis versus Random Mutagenesis

There are two general approaches to solving structure-function problems of the sort presented by attempts to define the determinants involved in mediating the association of the subunits that comprise the G protein heterotrimer. The first approach, discussed above with respect to hybrid constructs, is a rational one in which specific mutations or alterations are introduced into a molecule based upon the available experimental evidence. In a second approach, random mutagenesis techniques, coupled with selection or screening systems, are used to introduce large numbers of mutations into a molecule, and that collection of randomly mutated molecules is then subjected to a selection for the desired phenotype or a screen in which the desired phenotype can be observed against a background of undesirable phenotypes. With random mutagenesis one can mutagenize an entire molecule or one can proceed by cassette mutagenesis. In the former instance, the entire coding region of a molecule is mutagenized by one of several methods (chemical, PCR, doped oligonucleotide synthesis) and that collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise. In the second approach, discrete regions of a protein, corresponding either to defined structural (i.e. a-helices, b-sheets, turns, surface loops) or functional determinants (e.g., catalytic clefts, binding determinants, transmembrane segments) are subjected to saturating or semi-random mutagenesis and these mutagenized cassettes are re-introduced into the context of the otherwise wild type allele. Cassette mutagenesis is most useful when there is experimental evidence available to suggest a particular function for a region of a molecule and there is a powerful selection and/or screening approach available to discriminate between interesting and uninteresting mutants. Cassette mutagenesis is also useful when the parent molecule is comparatively large and the desire is to map the functional domains of a molecule by mutagenizing the molecule in a step-wise fashion, i.e. mutating one linear cassette of residues at a time and then assaying for function.

We are applying random mutagenesis in order to further delineate the determinants involved in Gα-Gβγ association. Random mutagenesis may be accomplished by many means, including:

1. PCR mutagenesis, in which the error prone Taq polymerase is exploited to generate mutant alleles of Gα subunits, which are assayed directly in yeast for an ability to couple to yeast Gβγ.
2. Chemical mutagenesis, in which expression cassettes encoding Gα subunits are exposed to mutagens and the protein products of the mutant sequences are assayed directly in yeast for an ability to couple to yeast Gβγ.
3. Doped synthesis of oligonucleotides encoding portions of the Gα gene.
4. In vivo mutagenesis, in which random mutations are introduced into the coding region of Gα subunits by passage through a mutator strain of *E. coli*, XL1-Red (mutD5 mutS mutT) (Stratagene, Menasa, Wis.).

The random mutagenesis may be focused on regions suspected to be involved in Gα-Gβγ association as discussed in the next section. Random mutagenesis approaches are feasible for two reasons. First, in yeast one has the ability to construct stringent screens and facile selections (growth vs. death, transcription vs. lack of transcription) that are not readily available in mammalian systems. Second, when using yeast it is possible to screen efficiently through thousands of transformants rapidly.

Cassette mutagenesis is immediately suggested by the observation (see infra) that the $GPA_{41}$ hybrids couple to the pheromone response pathway. This relatively small region of Gα subunits represents a reasonable target for this type of mutagenesis. Another region that may be amenable to cassette mutagenesis is that defining the surface of the switch region of Gα subunits that is solvent-exposed in the crystal structures of Gαi1 and transducin. From the data described below, this surface may contain residues that are in direct contact with yeast Gβγ subunits, and may therefore be a reasonable target for mutagenesis.

Rational Design of Chimeric Gα Subunits

Several classes of rationally designed GPA1-mammalian Gα hybrid subunits have been tested for the ability to couple to yeast βγ. The first, and largest, class of hybrids are those that encode different lengths of the GPA1 amino terminal domain in place of the homologous regions of the mammalian Gα subunits. This class of hybrid molecules includes $GPA_{BamHI}$, $GPA_{41}$, $GPA_{ID}$, and $GPA_{LW}$ hybrids, described below. The rationale for constructing these hybrid Gα proteins is based on results, described above, that bear on the importance of the amino terminal residues of Gα in mediating interaction with Gβγ.

Preferably, the yeast Gα subunit is replaced by a chimeric Gα subunit in which a portion, e.g., at least about 20, more preferably at least about 40, amino acids, which is substantially homologous with the corresponding residues of the amino terminus of the yeast Gα, is fused to a sequence substantially homologous with the main body of a mammalian (or other exogenous) Gα. While 40 amino acids is the suggested starting point, shorter or longer portions may be tested to determine the minimum length required for coupling to yeast Gβγ and the maximum length compatible with retention of coupling to the exogenous receptor. It is presently believed that only the final 10 or 20 amino acids at the carboxy terminus of the Gα subunit are required for interaction with the receptor.

$GPA_{BamHI}$ Hybrids. Kang et al. (1990) described hybrid Gα subunits encoding the amino terminal 310 residues of GPA1 fused to the carboxyl terminal 160, 143 and 142 residues, respectively, of GαS, Gαi2, and Gαo. In all cases examined by Kang et al., the hybrid proteins were able to complement the growth arrest phenotype of gpa1 strains. We have confirmed these findings and, in addition, have constructed and tested hybrids between GPA1 and Gαi3, Gαq and Gα16 (see Example 11). All hybrids of this type that have been tested functionally complement the growth arrest phenotype of gpa1 strains.

$GPA_{41}$ Hybrids. The rationale for constructing a minimal hybrid encoding only 41 amino acids of GPA1 relies upon the biochemical evidence for the role of the amino-terminus of Gα subunits discussed above, together with the following observation. Gβ and Gγ subunits are known to interact via α-helical domains at their respective amino-termini (Pronin, et al. 1992; Garritsen, et al. 1993). The suggestion that the amino termini of Gα subunits may form an helical coil and that this helical coil may be involved in association of Gα with Gβγ (Masters, Stroud, and Bourne 1986; Lupas, Lupas and Stock 1992) leads to the hypothesis that the three subunits of the G-protein heterotrimer interact with one another reversibly through the winding and unwinding of their amino-terminal helical regions. A mechanism of this type has been suggested, as well, from an analysis of leucine zipper mutants of the GCN4 transcription factor (Harbury, et al. 1993). The rationale for constructing hybrids like those described by Kang, et al. (1990), that contain a majority of yeast sequence and only minimal mammalian sequence, derives from their ability to function in assays of coupling between Gα and Gβγ subunits. However, these chimeras had never been assayed for an ability to couple to both mammalian G protein-coupled receptors and yeast Gβγ subunits, and hence to reconstitute a hybrid signalling pathway in yeast.

$GPA_{41}$ hybrids that have been constructed and tested include Gαs, Gα12, Gαi3, Gαq, $Gαo_a$, $Gαo_b$, and Gα16 (see Example 11). Hybrids of Gαs, Gαi2, Gαi3, and Gα16 functionally complement the growth arrest phenotype of gpa1 strains, while GPA$_{41}$ hybrids of Gαo$_a$ and Gαo$_b$ do not. In addition to being tested in a growth arrest assay, these constructs have been assayed in the more sensitive transcriptional assay for activation of a fus1p-HIS3 gene. In both of these assays, the GPA$_{41}$-Gαs hybrid couples less well than the GPA$_{41}$-i2, -i3, and -16 hybrids, while the GPA$_{41}$, -o$_a$ and -o$_b$ hybrids do not function in either assay.

Several predictive algorithms indicate that the amino terminal domain up to the highly conserved sequence motif -LLLLGAGESG-(SEQ ID NO: 129) (the first L in this motif is residue 43 in GPA1) forms a helical structure with amphipathic character. Assuming that a heptahelical repeat unit, the following hybrids between GPA1 and GaS can be used to define the number of helical repeats in this motif necessary for hybrid function:

GPA1-7/Gαs8-394
GPA1-14/Gαs15-394
GPA1-21/Gαs22-394
GPA1-28/Gαs29-394
GPA1-35/Gαs36-394
GPA1-42/Gαs43-394

In this hybrids, the prediction is that the structural repeat unit in the amino terminal domain up to the tetra-leucine motif is 7, and that swapping sequences in units of 7 will in effect amount to a swap of unit turns of turns of the helical structure that comprises this domain.

A second group of "double crossover" hybrids of this class are those that are aligned on the first putative heptad repeat beginning with residue G11 in GPA1. In these hybrids, helical repeats are swapped from GPA1 into a GaS backbone one heptad repeat unit at a time.

GαS1-10/GPA11-17/Gαs18-394
GαS1-17/GPA18-24/GαS25-394
GαS1-17/GPA25-31/GαS32-394
GαS1-17/GPA32-38/GαS39-394

The gap that is introduced between residues 9 and 10 in the GaS sequence is to preserve the alignment of the -LLLL-GAGE-(SEQ ID NO: 130) sequence motif.

This class of hybrids can be complemented by cassette mutagenesis of each heptad repeat followed by screening of these collections of "heptad" libraries in standard coupling assays.

A third class of hybrids based on the prediction that the amino terminus forms a helical domain with a heptahelical repeat unit are those that effect the overall hydrophobic or hydrophilic character of the opposing sides of the predicted helical structure (See Lupas, Stock and Stock). In this model, the α and d positions of the heptad repeat abcdefg are found to be conserved hydrophobic residues that define one face of the helix, while the e and g positions define the charged face of the helix.

In this class of hybrids, the sequence of the GaS parent is maintained except for specific substitutions at one or more of the following critical residues to render the different helical faces of GaS more "GPA1-like"

K8Q
+I-10
E10G
Q12E
R13S
N14D
E15P
E15F
K17L
E21R
K28Q
K32L
V36R

This collection of single mutations could be screened for coupling efficiency to yeast Gβγ and then constructed in combinations (double and greater if necessary).

A fourth class of hybrid molecules that span this region of GPA1-Gα hybrids are those that have junctions between GPA1 and Gα subunits introduced by three primer PCR. In this approach, the two outside primers are encoded by sequences at the initiator methionine of GPA1 on the 5' side and at the tetraleucine motif of GαS (for example) on the 3' side. A series of junctional primers spanning different junctional points can be mixed with the outside primers to make a series of molecules each with different amounts of GPA1 and GaS sequences, respectively.

GPA$_{ID}$ and GPA$_{LW}$ Hybrids. The regions of high homology among Gα Subunits that have been identified by sequence alignment are interspersed throughout the molecule. The G1 region containing the highly conserved -GSGESGDST-(SEQ ID NO: 125) motif is followed immediately by a region of very low sequence conservation, the "i1" or insert 1 region. Both sequence and length vary considerably among the i1 regions of the Gα subunits. By aligning the sequences of Gα subunits, the conserved regions bounding the i1 region were identified and two additional classes of GPA1-Gα hybrids were constructed. The GPA$_{ID}$ hybrids encode the amino terminal 102 residues of GPA1 (up to the sequence -QARKLGIQ-(SEQ ID NO: 126) fused in frame to mammalian Gα subunits, while the GPA$_{LW}$ hybrids encode the amino terminal 244 residues of GPA1 (up to the sequence -LIHE-DIAKA-(SEQ ID NO: 127) in GPA1). The reason for constructing the GPA$_{ID}$ and GPA$_{LW}$ hybrids was to test the hypothesis that the i1 region of GPA1 is required for mediating the interaction of GPA1 with yeast Gβγ subunits, for the stable expression of the hybrid molecules, or for function of the hybrid molecules. The GPA$_{ID}$ hybrids contain the amino terminal domain of GPA1 fused to the i1 domain of mammalian subunits, and therefore do not contain the GPA1 i1 region, while the GPA$_{LW}$ hybrids contain the amino terminal 244 residues of GPA1 including the entire i1 region (as defined by sequence alignments). Hybrids of both GPA$_{ID}$ and GPA$_{LW}$ classes were constructed for GαS, Gαi2, Gαi3, Gαo$_a$, and Gα16; none of these hybrids complemented the gpa1 growth arrest phenotype.

Subsequent to the construction and testing of the GPA$_{ID}$ and GPA$_{LW}$ classes of hybrids, the crystal structures of Gα$_{transductin}$ in both the GDP and GTPγ S-liganded form, and the crystal structure of several Gαi1 variants in the GTPγ S-liganded and GDP-AlF$_4$ forms were reported (Noel et al. 1993; Lambright et al. 1994 and Coleman et al. 1994). The crystal structures reveal that the i1 region defined by sequence alignment has a conserved structure that is comprised of six alpha helices in a rigid array, and that the junctions chosen for the construction of the GPA$_{ID}$ and GPA$_{LW}$ hybrids were not compatible with conservation of the structural features of the i1 region observed in the crystals. The junction chosen for the GPA$_{ID}$ hybrids falls in the center of the long αA helix; chimerization of this helix in all likelihood destabilizes it and the protein structure in general. The same is true of the junction chosen for the GPA$_{LW}$ hybrids in which the crossover point between GPA1 and the mammalian Gα subunit falls, at the end of the short αC helix and therefore may distort it and destabilize the protein.

The failure of the GPA$_{ID}$ and GPA$_{LW}$ hybrids is predicted to be due to disruption of critical structural elements in the i1 region as discussed above. Based upon new alignments and the data presented in Noel et al (1993), Lambright et al (1994), and Coleman et al (1994), this problem can be averted with the following hybrids. In these hybrids, the junctions between the ras-like core domain and the i1 helical domain are introduced outside of known structural elements like alpha-helices.

Hybrid A GαS1-67/GPA66-299/GαS203-394

This hybrid contains the entire i1 insert of GPA1 interposed into the GαS sequence.

Hybrid B GPA1-41/GαS4443-67/GPA66-299/GαS203-394

This hybrid contains the amino terminal 41 residues of GPAl in place of the 42 amino terminal residues of GαS found in Hybrid A.

Gas Hybrids. There is evidence that the "switch region" encoded by residues 171-237 of Gα transducin (using the numbering of Noel et al (1993) ) also plays a role in Gβγ coupling. First, the G226A mutation in GαS (Miller et al. 1988) prevents the GTP-induced conformational change that occurs with exchange of GDP for GTP upon receptor activation by ligand. This residue maps to the highly conserved sequence -DVGGQ-(SEQ ID NO: 118), present in all Gα subunits and is involved in GTP hydrolysis. In both the Gαt and Gαi1 crystal structures, this sequence motif resides in the loop that connects the β3 sheet and the α2 helix in the guanine nucleotide binding core. In addition to blocking the conformational change that occurs upon GTP binding, this mutation also prevents dissociation of GTP-liganded Gas from Gβγ. Second, crosslinking data reveals that a highly conserved cysteine residue in the α2 helix (C215 in Gαo, C210 in Gαt) can be crosslinked to the carboxy terminal region of Gβ subunits. Finally, genetic evidence (Whiteway et al. 1993) identifies an important single residue in GPA1 (E307) in the β2 sheet of the core structure that may be in direct contact with βγ. A mutation in the GPA1 protein at this position suppresses the constitutive signaling phenotype of a variety of STE4 (Gβ) dominant negative mutations that are also known to be defective in Gα-Gβγ association (as assessed in two-hybrid assay in yeast as well as by more conventional genetic tests).

We have tested the hypothesis that there are switch region determinants involved in the association of Gα with Gβγ by constructing a series of hybrid Gα proteins encoding portions of GPA1 and GαS in different combinations (FIG. 11). The hybrid proteins were tested in both biological assay described above and the results are summarized in Table 6.

Two conclusions may be drawn. First, in the context of the amino terminus of GαS, the GPA1 switch region suppresses coupling to yeast Gβγ (SGS), while in the context of the GPA1 amino terminus the GPA1 switch region stabilizes coupling with Gβγ (GPA$_{41}$-SGS). This suggests that these two regions of GPA1 collaborate to allow interactions between Gα subunits and Gβγ subunits. This conclusion is somewhat mitigated by the observation that the GPA$_{41}$-Gαs hybrid that does not contain the GPA1 switch region is able to complement the growth arrest phenotype of gpa1 strains. We have not to date noted a quantitative difference between the behaviour of the GPA$_{41}$-Gαs allele and the GPA$_{41}$-SGS allele, but if this interaction is somewhat degenerate, then it may be difficult to quantitate this accurately. The second conclusion that can be drawn from these results is that there are other determinants involved in stabilizing the interaction of Gα with Gβγ beyond these two regions as none of the GPA1/Gαs hybrid proteins couple as efficiently to yeast Gβγ as does native GPA1.

The role of the surface-exposed residues of this region may be crucial for effective coupling to yeast Gβγ, and can be incorporated into hybrid molecules as follows below.

GαS-GPA-Switch GαS 1-202/GPA298-350/GαS 253-394

This hybrid encodes the entire switch region of GPA 1 in the context of GaS.

GαS-GPA-α2 GαS 1-226/GPA322-332/GαS 238-394

This hybrid encodes the a² belix of GPA1 in the context of GaS.

GPA41-GαS-GPA-α2   GPA1-41/GαS43-226/GPA322-332/GαS238-394

This hybrid encodes the 41 residue amino terminal domain of GPA1 and the α2 helix of GPA1 in the context of GαS.

Finally, the last class of hybrids that will be discussed here are those that alter the surface exposed residues of the β2 and β3 sheets of αS so that they resemble those of the GPA1 αs helix. These altered α2 helical domains have the following structure. (The positions of the altered residues correspond to GαS.)

L203K
K211E
D215G
K216S
D229S

These single mutations can be engineered into a GαS backbone singly and in pairwise combinations. In addition, they can be introduced in the context of both the full length GαS and the GPA$_{41}$-GαS hybrid described previously. All are predicted to improve the coupling of Gα subunits to yeast Gβγ subunits by virtue of improved electrostatic and hydrophobic contacts between this region and the regions of Gβ defined by Whiteway and co-workers (Whiteway et al (1994) that define site(s) that interact with GPA1).

Summary. Identification of hybrid Gα subunits that couple to the yeast pheromone pathway has led to the following general observations. First, all GPA$_{BamHI}$ hybrids associate with yeast Gβγ, therefore at a minimum these hybrids contain the determinants in GPA1 necessary for coupling to the pheromone response pathway. Second, the amino terminal 41 residues of GPA1 contain sufficient determinants to facilitate coupling of Gα hybrids to yeast Gβγ in some, but not all, instances, and that some Gα subunits contain regions outside of the first 41 residues that are sufficiently similar to those in GPA1 to facilitate interaction with GPA1 even in the absence of the amino terminal 41 residues of GPA1. Third, there are other determinants in the first 310 residues of GPA1 that are involved in coupling Gα subunits to yeast Gβγ subunits.

The various classes of hybrids noted above are not mutually exclusive. For example, a Gα containing GPA1-41 could also feature the L203K mutation.

While, for the sake of simplicity, we have described hybrids of yeast GPA1 and a mammalian Gαs, it will be appreciated that hybrids may be made of other yeast Gα subunits and/or other mammalian Gα subunits, notably mammalian Gαi subunits. Moreover, while the described hybrids are constructed from two parental proteins, hybrids of three or more parental proteins are also possible.

As shown in the Examples, chimeric Gα subunits have been especially useful in coupling receptors to Gαi species.

Expression of Gα

Kang et al. (1990) reported that several classes of native mammalian Gα subunits were able to interact functionally with yeast βγ subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not desirable for uses like those described in this application. Reconstruction of G protein-coupled receptor signal transduction in yeast requires the signalling component of the heterotrimeric complex (Gβγ) to be present stoichiometrically with Gα subunits. An excess of Gα subunits (as was required for coupling of mammalian Gαi2 and Gαo to yeast Gβγ in Kang et al.) would dampen the signal in systems where Gβγ subunits transduce the signal. An excess of Gβγ subunits raises the background level of signalling in the system to unacceptably high levels.

Preferably, levels of Gα and Gβγ subunits are balanced. For example, heterologous Gα subunits may be expressed from a low copy (CEN ARS) vector containing the endogenous yeast GPA1 promoter and the GPA1 3' untranslated region. The minimum criterion, applied to a heterologous Gα subunit with respect to its ability to couple functionally to the yeast pheromone pathway, is that it complement a gpa1 genotype when expressed from the GPA1 promoter on low copy plasmids or from an integrated, single copy gene. In the work described in this application, all heterologous Gα subunits have been assayed in two biological systems. In the first assay heterologous Gα subunits are tested for an ability to functionally complement the growth arrest phenotype of gpa1 strains. In the second assay the transcription of a fus1-HIS3 reporter gene is used to measure the extent to which the pheromone response pathway is activated, and hence the extent to which the heterologous Gα subunit sequesters the endogenous yeast Gβγ complex.

Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpa1 strains was not observed in either assay system with any of these full-length Gα constructs with the exception of rat and human GαS.

Chimeric Yeast βγ Subunits

An alternative to the modification of a mammalian Gα subunit for improved signal transduction is the modification of the pertinent sites in the yeast Gβ or Gγ subunits. The principles discussed already with respect to Gα subunits apply, mutatis mutandis, to yeast Gβ or Gγ.

For example, it would not be unreasonable to target the yeast Ste4p Gβ subunit with cassette mutagenesis. Specifically, the region of Ste4p that encodes several of the dominant negative, signalling-defective mutations would be an excellent target for cassette mutagenesis when looking for coupling of yeast Gβγ to specific mammalian Gα subunits.

Protein Kinases

Mitogen-activated protein kinase (MAP kinase) and its activator, MAP kinase kinase or MEK, are believed to be key molecules in the transduction of intracellular signals in mammalian cells. The activity of MAPK, a serine/threonine protein kinase, has been shown to depend on its phosphorylation by the dually specific MEK at tyrosine and threonine residues. MEK activity, in turn, depends on its phosphorylation on serine and threonine by a third kinase, MAP kinase kinase kinase, or MEKK, whose function in some systems is fulfilled by the protooncogene product Raf1p.

An essential part of the *S. cerevisiae* pheromone signalling pathway is comprised of a protein kinase cascade composed of the products of the STE11, STE7, and FUS3/KSS1 genes (the latter pair are distinct and functionally redundant). Functional studies have established the dependence of FUS3p activity on tyrosine and threonine phosphorylation by STE7p, whose activity is regulated by its phosphorylation by STE11p. A second protein kinase cascade, responsive to protein kinase C, has been identified in *S. cerevisiae*. When this pathway is disrupted, yeast cells lose their ability to grow in media of low osmotic strength. Although its components have not been characterized to the same extent as that of the mating pathway cascade, sequence analysis identifies BCK1p as a MEKK, MKK1p/MKK2p as MEKs, and MPK1p as a MAPK.

Kinase signalling pathways appear to be conserved among eukaryotes. Thus significant sequence homology is found between Xenopus MAP kinase and the products of the following yeast kinase genes: FUS3, KSS1, MPK1 (*S. cerevisiae*) and Spk1 (*Schizosaccharomyces pombe*). In addition, mammalian MEK has been found to be homologous to the products of STE7 (*S. cerevisiae*) and Byr1 (*S. pombe*) [Crews et al. Science 258, 478 (1992)]. Functional homologies between some kinases has been demonstrated through substitution of heterologous kinase genes in yeast kinase deletion mutants. Thus Xenopus MAP kinase will complement an mpk1Δ mutant in *S. cerevisiae* (however, this kinase will not substitute for Fus3p or Kss1p function in the same organism) [Lee et al. Mol. Cell. Biol. 13, 3067 (1993)]. Both mammalian and Xenopus MAP kinase will substitute for Spk1 function in *S. pombe* [Neiman et al. Molec. Biol. Cell. 4, 107 (1993); Gotoh et al. Molec. Cell. Biol. 13, 6427 (1993)]. Rabbit MAP kinase kinase will complement a byri defect in *S. pombe* but only when co-expressed with Raf1 kinase; the latter thus appears to be a direct activator of MEK (Hughes et al. Nature 364, 349 (1993).

The use of the instant invention to screen for modulators of human MEK is described in Example 9.

Cyclins

Members of another mammalian protein kinase family, one active in progression through the cell cycle, have been identified by complementation of cell cycle kinase mutants in yeast. The human homologue of p34cdc2 (*S. pombe*) and p34cdc28 (*S. cerevisiae*), proteins which control the progression to DNA synthesis and mitosis in yeast, was identified by complementation of a cdc2 mutation in *S. pombe* [Lee and Nurse, Nature 327, 31-35 (1987)]. CDK2, a second human p34 homologue, was identified by functional complementation of p34cdc28 mutations in *S. cerevisiae* [Elledge and Spottswood, EMBO J. 10, 2653 (1991)]. Activation of p34 depends on its association with regulatory subunits, termed cyclins. Tight control of cyclin expression as well as the inherent instability of these proteins once expressed contribute to a regulated activation of p34 kinase and progression through the cell cycle.

A number of putative G1 human cyclins have been identified through their ability to substitute for the yeast G1 cyclins, CLN1, CLN2 and CLN3, in the pheromone signalling pathway. Thus human cyclins C, D and E were identified by their ability to rescue cln yeast from growth arrest [Lew et al., Cell 66, 1197 (1991)]. It has also been demonstrated that other classes of human cyclins can substitute functionally for the CLN proteins in yeast. The human cyclins A, B1 and B2 (cyclins normally associated with governance of mitosis) will also function as G1 cyclins in *S. cerevisiae* [Lew et al., Cell 66, 1197 (1991)].

Certain cyclins are periodically accumulating regulators of the p34 kinase (p34cdc2 in humans and p34cdc28 in *S. cerevisiae*). The p34 kinase is functionally conserved from yeast to humans and the activity of this threonine/serine-specific protein kinase is required if cells are to progress through several checkpoints in the cell cycle, including one that is termed START. START occurs late in the G1 phase and is the switch point for cells between the quiescent state and proliferation. The kinase is activated at discrete points in the cell cycle through its association with specific cyclins, regulatory subunits which are also functionally conserved among eukaryotes. Three cyclins appear to operate in progression through START in *S. cerevisiae*, CLN1, CLN2 and CLN3 (Hadwiger et al. 1989; Cross 1988; Nash 1988). The sequences of the CLN proteins bear some homology to those of mammalian A- and B-type cyclins; these proteins are believed to regulate S (DNA synthesis) and M (mitotic) phases of the mammalian cell cycle.

Sequence comparisons among the cyclin proteins identified in different species indicates that a region of high sequence conservation is contained within an approximately 87 residue domain that generally comprises central cyclin sequence but which is located near the amino terminus of the yeast G1 cyclins. This conserved domain is termed the "cyclin box". A second region of homology shared by most of the cyclins is a C-terminal sequence rich in proline, glutamate, serine, threonine and aspartate residues flanked by basic amino acids that is termed a PEST motif (Rogers et al. 1986). PEST motifs are found in unstable proteins and are believed to signal for constitutive ubiquitin-mediated degradation. The degradation of cyclins A and B is signalled via a different sequence, a "mitotic destruction motif" (Glotzer et al. 1991), that is not shared by other mammalian cyclins.

Sequence comparisons made between the yeast CLN proteins and the human A, B, C, D and E cyclins indicate the existence of appreciable homologies (Lew et al. 1991). Across the most conserved regions, including the cyclin box, human cyclin C bears 18sequence identity both to human cyclins D and E and to the yeast CLN proteins. Human cyclins D and E appear to be more related to human A- and B-type cyclins (33% identical) than to the yeast CLNs (24% identical).

All human cyclins identified to date will substitute functionally for yeast cyclins. In fact, the mammalian cyclins C, D1 and E were identified through their ability to complement defective CLN function in yeast (Lew et al. 1991). Mammalian A- and B-type cyclins also substitute functionally for the CLN proteins in yeast, therefore this ability cannot definitively mark a mammalian cyclin as one that would operate in G1. However, the cyclins C, D1 and E have been shown to be expressed in G1 in mammalian cells and the expression pattern of cyclin E during the cell cycle most closely parallels the expression patterns observed for the yeast G1 cyclins (Lew et al. 1991; Koff et al. 1991).

In mammalian cells, cyclin C mRNA accumulates early in G1 while cyclin E accumulates late in that phase. D cyclin mRNA levels are insufficient to allow tracking of expression patterns in human cells and the role of this cyclin is therefore not clear (Lew et al. 1991). In mouse cells, the D1 gene, CYL1, is expressed in the G1 phase and the D1 gene appears to be regulated by colony-stimulating factor 1 (Matsushime et al. 1991). Expression of D1 cyclin is highly growth factor-dependent and therefore may not be an integral part of the internal cell cycle control mechanism, but may occur only in response to external signalling (Scherr 1993). The PRAD1 gene, found overexpressed in some parathyroid adenomas is identical to the D1 gene (Motokura et al. 1991). D1 has also been found to be overexpressed in a glioblastoma cell line (Xiong et al. 1991) and is subject to deregulation by gene amplification (Lammie et al. 1991; Keyomarsi and Pardee 1993). Deregulation of D1 occurs by unknown mechanisms in some lymphomas, squamous cell tumors and breast carcinomas (Bianchi et al. 1993). This protein is involved in activating the growth of cells and therefore, deregulated expression of this gene appears to be an oncogenic event. Some evidence exists that the E-type cyclin may function in the G1 to S transition in human cells: this cyclin binds to and activates p34cdc2 protein in extracts of human lymphoid cells in G1, the protein is associated with histone H1 kinase activity in HeLa cells (Koff et al. 1991) and cyclin E mRNA is specifically expressed in late G1 in HeLa cells (Lew et al. 1991).

It has been hypothesized that p34 cdc2 acts at discrete transition points in the cell cycle by phosphorylating varying substrates. The phosphorylating activity is manifest upon association of the kinase with cyclins which are differentially expressed throughout the cycle of the cell. These different cyclins may alter the substrate specificity of the kinase or may alter its catalytic efficiency (Pines and Hunter 1990). Obvious Potential substrates for the cdc2 kinase are transcription factors that control cell-cycle-stage-specific gene transcription.

Disruption of any one of the three CLN genes in yeast does not appreciably affect cell growth, however, upon disruption of all of the CLN genes, cells arrest in G1. In addition, in response to mating pheromone, the CLN proteins are inhibited and yeast cell growth is arrested. Two genes whose products inhibit cyclin activity have been identified in *S. cerevisiae*. The products of the FAR1 and FUS3 genes inhibit CLN2 and CLN3 function, respectively. With pheromone signalling, the levels of Far1p and Fus3p increase, the G1 cyclins do not accumulate, the CDC28p kinase remains inactive, and cell growth is arrested in G1. These observations suggest that inhibitors of the cyclin proteins, inhibitors of a productive association between the cyclins and the kinase, or inactivators of the kinase can foster cellular growth arrest.

By contrast, cyclins which are uninhabitable appear to function as uncontrolled positive growth regulators. High level expression of the CLN proteins is a lethal condition in yeast cells. Data indicate that the loss of controlled expression of cyclin D1 through chromosomal breakage, chromosomal translocation or gene amplification can promote oncogenicity in mammalian cells (Xiong et al. 1991; Lammie et al. 1991; Bianchi et al. 1993). In addition, it appears that events that disrupt the control of cyclin expression and control of cyclin function can result in bypass of the G1 checkpoint and dysregulated cellular growth. The cyclin proteins which operate in G1 to promote cellular proliferation would be ideal targets for therapeutics aimed at control of cell growth. Candidate surrogate proteins for substitution in the yeast pathway for identification of such therapeutics include human cyclins C, D and E. All three proteins are normally expressed during the G1 phase of the mammalian cell cycle and are thus candidate mediators of the commitment of cells to proliferate.

Examples of compounds which are known to act in G1 to prevent entry into S phase are transforming growth factor β (TGF-β) and rapamycin. Rapamycin, an immunosuppressant, inhibits the activity of cyclin E-bound kinase. This macrolide acts in G1 to prevent the proliferation of IL-2-stimulated T lymphocytes (Scherr 1993). TGF-β has been shown to prevent progression from G1 to S phase in mink lung epithelial cells (Howe et al. 1991). TGF-β appears to interfere with activation of the kinase, perhaps by reducing the stability of the complex which the kinase forms with cyclin E (Koff 1993).

A strain of yeast cells bearing inactive CLN1, CLN2 and CLN3 genes and an integrated chimeric gene encoding a Gal1 promoter-driven human CLN sequence (see DL1 cells, Lew et al. Cell 66, 1197 (1991) will serve as a tester strain. The Gal1 promoter permits high level expression when cells are grown in the presence of galactose but this promoter is repressed when cells are grown on glucose. Yeast cells so engineered are nonviable on glucose due to an absence of expression of functional cyclin. These yeast, however, proliferate on galactose-containing medium due to expression of the human cyclin sequence. Exposure of this strain to an inhibitor of cyclin function would render the cells incapable of growth, even on galactose medium, i.e., the cells would growth arrest in the presence or absence of galactose. This phenotype could serve as an indication of the presence of an exogenously applied cyclin inhibitor but would not be useful as a screen for the identification of candidate inhibitors from members of a random peptide library. Growth arrest of a subset of cells in an otherwise growing population is useless as an indicator system. Therefore, in order to identify random peptide inhibitors of mammalian cyclins, a two stage screen is envisioned.

A two-hybrid system described by Fields and Song (Nature 340, 245 (1989) permits the detection of protein-protein interactions in yeast. GAL4 protein is a potent activator of transcription in yeast grown on galactose. The ability of GAL4 to activate transcription depends on the presence of an N-terminal sequence capable of binding to a specific DNA sequence ($UAS_G$ and a C-terminal domain containing a transcriptional activator. A sequence encoding a protein, "A", may be fused to that encoding the DNA binding domain of the GAL4 protein. A second hybrid protein may be created by fusing sequence encoding the GAL4 transactivation domain to sequence encoding a protein "B". If protein "A" and protein "B" interact, that interaction serves to bring together the two domains of GAL4 necessary to activate transcription of a UASG-containing gene. In addition to co-expressing plasmids encoding both hybrid proteins, yeast strains appropriate for the detection of protein-protein interactions using this two-hybrid system would contain a GAL1-lacZ fusion to permit detection of transcription from a $UAS_G$ sequence. These strains should also be deleted for endogenous GAL4 and for GAL80, a negative regulator of GAL4.

In a variation of the two-hybrid system just described, the GAL4 DNA binding domain would be fused to a human cyclin sequence. In addition, oligonucleotides encoding random peptides would be ligated to sequence encoding the GAL4 transactivation domain. Co-transformation of appropriate yeast strains with plasmids encoding these two hybrid proteins and screening for yeast expressing β-galactosidase would permit identification of yeast expressing a random peptide sequence capable of interacting with a human cyclin. Identification of peptides with that capability would be the goal of this first stage of screening. ii. Once random peptides capable of interacting with a human cyclin of interest had been identified, second stage screening could commence. The second screen would permit the identification of peptides that not only bound to human cyclin but, through that interaction, inhibited cyclin activation of the cell cycle-dependent kinase and, thus, cellular proliferation. Thus, candidate peptides would be expressed, individually, in yeast lacking CLN1, CLN2 and CLN3 but expressing a human CLN sequence, as described above. Those peptides, expression of which does not permit growth of the tester strain on galactose, would. be presumed cyclin inhibitors.

An advantage to this two-stage approach to the identification of potential cyclin inhibitors is the high probability that random peptide sequences, selected in stage one interact with human cyclin proteins. A subsequently determined ability of that sequence to cause growth arrest of the tester yeast on galactose would be a strong indication that the growth arrest was due to a direct effect of the peptide on the cyclin and not on another protein, e.g., the cell cycle dependent kinase. Though a strong indication, such a result would not be an absolute indication and verification of the inhibitory effect on cyclin function could be obtained in vitro through biochemical assay.

Screening and Selection

A marker gene is a gene whose expression causes a phenotypic change which is screenable or selectable. If the change is selectable, the phenotypic change creates a difference in the growth or survival rate between cells which express the marker gene and those which do not. If the change is screenable, the phenotype change creates a difference in some detectable characteristic of the cells, by which the cells which express the marker may be distinguished from those which do not. Selection is preferable to screening.

The marker gene may be coupled to the yeast pheromone pathway so that expression of the marker gene is dependent on activation of the G protein. This coupling may be achieved by operably linking the marker gene to a pheromone-responsive promoter. The term "pheromone-responsive promoter" indicates a promoter which is regulated by some product of the yeast pheromone signal transduction pathway, not necessarily pheromone per se. In one embodiment, the promoter is activated by the pheromone pathway, in which case, for selection, the expression of the marker gene should result in a benefit to the cell. A preferred marker gene is the imidazoleglycerol phosphate dehydratase gene (HIS3). If a pheromone responsive promoter is operably linked to a beneficial gene, the cells will be useful in screening or selecting for agonists. If it is linked to a deleterious gene, the cells will be useful in screening or selecting for antagonists.

Alternatively, the promoter may be one which is repressed by the pheromone pathway, thereby preventing expression of a product which is deleterious to the cell. With a pheromone-repressed promoter, one screens for agonists by linking the promoter to a deleterious gene, and for antagonists, by linking it to a beneficial gene.

Repression may be achieved by operably linking a pheromone-induced promoter to a gene encoding mRNA which is antisense to at least a portion of the mRNA encoded by the marker gene (whether in the coding or flanking regions), so as to inhibit translation of that mRNA. Repression may also be obtained by linking a pheromone-induced promoter to a gene encoding a DNA-binding repressor protein, and incorporating a suitable operator site into the promoter or other suitable region of the marker gene.

Suitable positively selectable (beneficial) genes include the following: URA3, LYS2, HIS3, LEU2, TRP1; ADE1, 2, 3, 4, 5, 7, 8; ARG1, 3, 4, 5, 6, 8; HIS1, 4, 5; ILV1, 2, 5; THR1, 4; TRP2, 3, 4, 5; LEU1, 4; MET2, 3, 4, 8, 9, 14, 16, 19; URA1, 2, 4, 5, 10; HOM3, 6; ASP3; CHO1; ARO 2, 7; CYS3; OLE1; INO1, 2, 4; PRO1, 3 Countless other genes are potential selective markers. The above are involved in well-characterized biosynthetic pathways.

The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In a more complex version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanine), and other recessive drug-resistant markers.

The natural response to induction of the yeast pheromone response pathway is for cells to undergo growth arrest. This is the preferred way to select for antagonists to a ligand/receptor pair that induces the pathway. An autocrine peptide antagonist would inhibit the activation of the pathway; hence, the cell would be able to grow. Thus, the FAR1 gene may be considered an endogenous counterselectable marker. The FAR1 gene is preferably inactivated when screening for agonist activity.

The marker gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exb1 gene; nonessential, secreted); luciferase; and chloramphenicol transferase. Some of the above can be engineered so that they are secreted (although not β-galactosidase). The preferred screenable marker gene is beta-galactosidase; yeast cells expressing the enzyme convert the colorless substrate Xgal into a blue pigment. Again, the promoter may be pheromone-induced or pheromone-inhibited.

Yeast Cells

The yeast may be of any species that possess a G protein-mediated signal transduction pathway and which are cultivatable. Suitable species include *Kluvverei lactis, Schizosaccharomyces pombe*, and *Ustilago maydis; Saccharomyces cerevisiae* is preferred. Either Gα or Gβγ may be the activator of the "effecter." (It is suspected that in some species, both Gα-activated and Gβγ-activated effectors exist.) The term "yeast", as used herein, includes not only yeast in a strictly taxonomic sense (i.e., unicellular organisms), but also yeast-like multicellular fungi with pheromone responses mediated by the mating pathway.

The yeast cells of the present invention may be used to test peptides for the ability to interact with an exogenous G protein-coupled receptor or other PSP surrogate. The yeast cells must express both the exogenous G protein-coupled receptor (or other PSP surrogate), and a complementary G protein (or other PSPs necessary for the PSP surrogate to function in the pheromone system, if need be after activation by a drug), and these molecules must be presented in such a manner that a "readout" can be obtained by means of the pheromone response pathway (which may be modified to improve the readout).

For a readout to be possible, a gene encoding a selectable or screenable trait must be coupled to the G protein-mediated signal transduction pathway so that the level of expression of the gene is sensitive to the presence or absence of a signal, i.e., binding to the coupled exogenous receptor. This gene may be an unmodified gene already in the pathway, such as the genes responsible for growth arrest. It may be a yeast gene, not normally a part of the pathway, that has been operably linked to a "pheromone-responsive" promoter. Or it may be a heterologous gene that has been so linked. Suitable genes and promoters were discussed above.

It will be understood that to achieve selection or screening, the yeast must have an appropriate phenotype. For example, introducing a pheromone-responsive chimeric HIS3 gene into a yeast that has a wild-type HIS3 gene would frustrate genetic selection. Thus, to achieve nutritional selection, an auxotrophic strain is wanted.

The yeast cells of the present invention optionally possess one or more of the following characteristics:
(a) the endogenous FAR1 gene has been inactivated;
(b) the endogenous SST2 gene, and/or other genes involved in desensitization, has been inactivated;
(c) the endogenous pheromone (a- or α-factor) receptor gene has been inactivated; and
(d) the endogenous pheromone genes have been inactivated.

"Inactivation" means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

Mutants with inactivated supersensitivity-related genes can be identified by conventional genetic screening procedures. The far1 gene was identified as an α-factor resistant mutant that remained blue (with fus1-lacZ) on α-factor/Xgal. far2, as it turns out, is the same as fus3. Supersensitive mutants could be identified as constitutive weak blue colonies expressing fus1-lacZ on Xgal, or as strains that can mate more proficiently with a poor pheromone-secretor.

The DNA sequences of (a) the α- and a-factor genes, (b) the α- and a-factor receptors, (c) the FAR1 gene, (d) the SST2 gene, and (e) the FUS1 promoter have been reported in the following references:

MFa1 and MFa2: A J Brake, C Brenner, R Najarian, P Laybourn, and J Merryweather. Structure of Genes Encoding Precursors of the Yeast Peptide Mating Pheromone a-Factor. In Protein Transport and Secretion. Gething M-J, ed. Cold Spring Harbor Lab, New York, 1985.

MFα1 and MFα2: Singh, A. E Y Chen, J M Lugovoy, C N Chang, R A Hitzeman et al. 1983. Saccharomyces cerevisiae contains two discrete genes coding for the α-pheromone. Nucleic Acids Res. 11:4049; J Kurjan and I Herskowitz. 1982. Structure of a yeast pheromone gene (MF) : A putative α-factor precursor contains four tandem copies of mature α-factor. Cell 30:933.

STE2 and STE3: A C Burkholder and L H Hartwell. 1985. The yeast α-factor receptor: Structural properties deduced from the sequence of the STE2 gene. Nucleic Acids Res. 13:8463; N Nakayama, A Miyajima, and K Arai. 1985. Nucleotide sequences of STE2 and STE3, cell type-specific sterile genes from *Saccharomyces cerevisiae*. EMBO J. 4:2643; D C Hagen, G McCaffrey, and G F Sprague, Jr. 1986. Evidence the yeast STE3 gene encodes a receptor for the peptide pheromone a-factor: Gene sequence and implications for the structure of the presumed receptor. Proc Natl Acad Sci 83:1418.

FAR1: F Chang and I Herskowitz. 1990. Identification of a gene necessary for cell cycle arrest by a negative growth factor of yeast: FAR1 is an inhibitor of a G1 cyclin, CLN2. Cell 63:999.

SST2: C Dietzel and J Kurjan. 1987. Pheromonal regulation and sequence of the *Saccharomyces cerevisiae* SST2 gene: A model for desensitization to pheromone. Mol Cell Biol 7: 4169.

FUS1: J Trueheart, J D Boeke, and G R Fink. 1987. Two genes required for cell fusion during yeast conjugation: Evidence for a pheromone-induced surface protein. Mol Cell Biol 7:2316.

The various essential and optional features may be imparted to yeast cells by, e.g., one or more of the following means: isolation of spontaneous mutants with one or more of the desired features; mutation of yeast by chemical or radiation treatment, followed by selection; and genetic engineering of yeast cells to introduce, modify or delete genes.

Other explicit characteristics desirable in strains of yeast designed to be used as screening devices for inhibitors/activators of PSP surrogates are discussed in subsections dealing specifically with each molecular target.

Peptide

The term "peptide" is used herein to refer to a chain of two or more amino acids, with adjacent amino acids joined by peptide (—NHCO—) bonds. Thus, the peptides of the present invention include oligopeptides, polypeptides, and proteins. Preferably, the peptides of the present invention are 2 to 200, more preferably 5 to 50, amino acids in length. The minimum peptide length is chiefly dictated by the need to obtain sufficient potency as an activator or inhibitor. The maximum peptide length is only a function of synthetic convenience once an active peptide is identified.

For initial studies in which the cognate PSP was a yeast Pheromone receptor, a 13-amino acid peptide was especially preferred as that is the length of the mature yeast α-factor.

Peptide Libraries

A "peptide library" is a collection of peptides of many different sequences (typically more than 1000 different sequences), which are prepared essentially simultaneously, in such a way that, if tested simultaneously for some activity, it is possible to characterize the "positive" peptides.

The peptide library of the present invention takes the form of a yeast cell culture, in which essentially each cell expresses one, and usually only one, peptide of the library. While the diversity of the library is maximized if each cell produces a peptide of a different sequence, it is usually prudent to construct the library so there is some redundancy.

In the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide-encoding DNA molecule is introduced into a particular cell, it is not predictable which peptide that cell will produce. However, based on a knowledge of the manner in which the mixture was prepared, one may make certain statistical predictions about the mixture of peptides in the peptide library.

It is convenient to speak of the peptides of the library as being composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA.

Once the necessary "degenerate" DNA is complete, it must be joined with the DNA sequences necessary to assure the expression of the peptide, as discussed in more detail below, and the complete DNA construct must be introduced into the yeast cell.

Expression System

The expression of a peptide-encoding gene in a yeast cell requires a promoter which is functional in yeast. Suitable promoters include the promoters for metallothionein, 3-phosphoglycerate kinase (Hitzeman et al., J. Biol. Chem. 255, 073 (1980) or other glycolytic enzymes (Hess et al., *J. Adv. Enzyme Reg.* 7, 149 (1968); and Holland et al. *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In screens devised for a subset of PSP surrogates (e.g. kinases, cyclins) random peptide sequences need not be expressed in the context of yeast pheromone and need not be engineered for secretion or transport to the extracellular space. Libraries of random peptides may be expressed in a multiplicity of ways, including as portions of chimeric proteins, as in a two-hybrid protein system designed to signal protein-protein interactions. Random peptides need not necessarily substitute for yeast pheromones but can impinge on the pheromone pathway downstream of the interaction between pheromone and pheromone receptor (as in random peptide inhibitors of the kinases or of the cyclins).

In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

Vectors

The vector must be capable of replication in a yeast cell. It may be a DNA which is integrated into the host genome, and thereafter is replicated as a part of the chromosomal DNA, or it may be DNA which replicates autonomously, as in the case of a plasmid. In the latter case, the vector must include an origin of replication which is functional in the host. In the case of an integrating vector, the vector may include sequences which facilitate integration, e.g., sequences, homologous to host sequences, or encoding integrases.

Besides being capable of replication in yeast cells, it is convenient if the vector can also be replicated in bacterial cells, as many genetic manipulations are more conveniently carried out therein. Shuttle vectors capable of replication in both yeast and bacterial cells include YEps, YIps, and the pRS series.

Periplasmic Secretion

The cytoplasm of the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The peptide library may be secreted into the periplasm by one of two distinct mechanisms, depending on the nature of the expression system to which they are linked. In one system, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction would likely yield activation of the linked pheromone response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. We anticipate that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

EXAMPLE 1

Development of Autocrine Yeast Strains

In this example, we describe a pilot experiment in which haploid cells were engineered to be responsive to their own pheromones (see FIG. 1). (Note that in the examples, functional genes are capitalized and inactivated genes are in lower case.) For this purpose we constructed recombinant DNA molecules designed to:

i. place the coding region of STE2 under the transcriptional control of elements which normally direct the transcription of STE3. This is done in a plasmid that allows the replacement of genomic STE3 of *S. cerevisiae* with sequences wherein the coding sequence of STE2 is driven by STE3 transcriptional control elements.

ii. place the coding region of STE3 under the transcriptional control of elements which normally direct the transcription of STE2. This is done in a plasmid which will allow the replacement of genomic STE2 of *S. cerevisiae* with sequences wherein the coding sequence of STE3 is driven by STE2 transcriptional control elements.

The sequence of the STE2 gene is known see Burkholder A. C. and Hartwell L. H. (1985), "The yeast α-factor receptor: Structural properties deduced from the sequence of the STE2 gene," Nuc. Acids Res. 13, 8463; Nakayama N., Miyajima A., Arai K. (1985) "Nucleotide sequences of STE2 and STE3, cell type-specific sterile genes from *Saccharomyces cerevisiae*," EMBO J. 4, 2643.

A 4.3 kb BamHI fragment that contains the entire STE2 gene was excised from plasmid YEp24-STE2 (obtained from J. Thorner, Univ. of California) and cloned into pALTER (Protocols and Applications Guide, 1991, Promega Corporation, Madison, Wis.). An SpeI site was introduced 7 nucleotides (nts) upstream of the ATG of STE2 with the following mutagenic oligonucleotide, using the STE2 minus strand as template (mutated bases are underlined and the start codon is in bold type):

5' GTTAAGAACCATAT<u>AC</u>TAG<u>T</u>ATCAAAAATGTCTG 3' (SEQ ID NO:14).

A second SpeI site was simultaneously introduced just downstream of the STE2 stop codon with the following mutagenic oligonucleotide (mutated bases are underlined and the stop codon is in bold type):

5' TGATCAAAATTTAC<u>T</u>AGTTTGAAAAAGTAATTTCG 3' (SEQ ID NO:15).

The BamHI fragment of the resulting plasmid (Cadus 1096), containing STE2 with SpeI sites immediately flanking the coding region, was then subcloned into the yeast integrating vector YIp1 to yield Cadus 1143.

The STE3 sequence is also known. Nakayama N., Miyajima A., Arai K. (1985), "Nucleotide sequences of STE2 and STE3, cell type-specific sterile genes from *Saccharomyces cerevisiae*," EMBO J. 4, 2643; Hagen D. C., McCaffrey G., Sprague G. F. (1986), "Evidence the yeast STE3 gene encodes a receptor for the peptide pheromone a-factor: gene sequence and implications . for the structure of the presumed receptor," Proc. Natl. Acad. Sci. 83, 1418. STE3 was made available by Dr. J. Broach as a 3.1 kb fragment cloned into pBLUESCRIPT-KS II (Stratagene, 11011 North Torrey Pines Road, La Jolla, Calif. 92037). STE3 was subcloned as a KpnI-XbaI fragment into both M13mp18 RF (to yield Cadus 1105) and pUC19 (to yield Cadus 1107). The two SpeI sites in Cadus 1107 were removed by digestion with SpeI, fill-in with DNA polymerase I Klenow fragment, and recircularization by blunt-end ligation. Single-stranded DNA containing the minus strand, of STE 3 was obtained using Cadus 1105 and SpeI sites were introduced 9 nts upstream of the start codon and 3 nts downstream of the stop codon of STE3 with the following mutagenic oligonucleotides, respectively:

```
                                             (SEQ ID NO: 16)
5' GGCAAAATACTAGTAAAATTTTCATGTC 3'.
```

```
                                             (SEQ ID NO: 17)
5' GGCCCTTAACACACTAGTGTCGCATTATATTTAC 3'.
```

The mutagenesis was accomplished using the T7-GEN protocol of United States Biochemical (T7-GEN In Vitro Mutagenesis Kit, Descriptions and Protocols, 1991, United States Biochemical, P.O. Box 22400, Cleveland, Ohio 44122). The replicative form of the resulting Cadus 1141 was digested with AflII and KpnI, and the approximately 2 kb fragment containing the entire coding region of STE3 flanked by the two newly introduced Spe I sites was isolated and ligated with the approximately 3.7 kb vector fragment of AflII- and KpnI-digested Cadus 1107, to yield Cadus 1138. Cadus 1138 was then digested with XbaI and KpnI, and the STE3-containing 2.8 kb fragment was ligated into the XbaI- and KpnI-digested yeast integrating plasmid pRS406 (Sikorski, R. S. and Hieter, P. (1989) "A System of Shuttle Vectors and Yeast Host Strains Designed for Efficient Manipulation of DNA in *Saccharomyces cerevisiae*", *Genetics* 122:19-27 to yield Cadus 1145.

The SpeI fragment of Cadus 1143 was replaced with the SpeI fragment of Cadus 1145 to yield Cadus 1147, in which the coding sequences of STE3 are under the control of STE2 expression elements. Similarly, the SpeI fragment of Cadus 1145 was replaced with the SpeI fragment of Cadus 1143 to yield Cadus 1148, in which the coding sequences of STE2 are under the control of STE3 expression elements. Using the method of pop-in/pop-out replacement (Rothstein, R. (1991) "[19] Targeting, Disruption, Replacement, and Allele Rescue: Integrative DNA Transformation in Yeast", *Methods in Enzymology*, 194:281-301), Cadus 1147 was used to replace genomic STE2 with the ste2-STE3hybrid in a MATa cell and Cadus 1148 was used to replace genomic STE3 with the ste3-STE2 hybrid in a MATαcell. Cadus 1147 and 1148 contain the selectable marker URA3.

Haploid yeast of mating type a which had been engineered to express HIS3 under the control of the pheromone-inducible FUS1promoter were transformed with CADUS 1147, and transformants expressing URA3 were selected. These transformants, which express both Ste2p and Ste3p, were plated on 5-fluoroorotic acid to allow the selection of clones which had lost the endogenous STE2, leaving in its place the heterologous, integrated STE3. Such cells exhibited the ability to grow on media deficient in histidine, indicating autocrine stimulation of the pheromone response pathway.

Similarly, haploids of mating type a that can express HIS3under the control of the pheromone-inducible FUS1 promoter were transformed with CADUS 1148 and selected for replacement of their endogenous STE3 with the integrated STE2. Such cells showed, by their ability to grow on histidine-deficient media, autocrine stimulation of the pheromone response pathway.

EXAMPLE 2

Strain Development

In this example, yeast strains are constructed which will facilitate selection of clones which exhibit autocrine activation of the pheromone response pathway. To construct appropriate yeast strains, we will use: the YIp-STE3 and pRS-STE2 knockout plasmids described above, plasmids available for the knockout of FAR1, SST2, and HIS3, and mutant strains that are commonly available in the research community. The following haploid strains will be constructed, using one-step or two-step knockout protocols described in Meth. Enzymol 194:281-301, 1991:

1. MATα ste3::STE2::ste3 far1 sst2 FUS1::HIS3
2. MATa ste2::STE3::ste2 far1 sst2 FUS1::HIS3
3. MATα ste3::STE2::ste3 far1 sst2 mfα1 mfα2 FUS1::HIS3
4. MATa ste2::STE3::ste2 far1 sst2 mfa1 mfa2 FUS1::HIS3
5. MATa bar1 far1-1 fus1-HIS3 ste14::TRP1 ura3 trp1 leu2 his3
6. MATa mfa1 mfa2 far1-1 his3::fus1-HIS3 ste2-STE3 ura3 met1 ade1 leu2

Strains 1 and 2 will be tested for their ability to grow on histidine-deficient media as a result of autocrine stimulation of their pheromone response pathways by the pheromones which they secrete. If these tests prove successful, strain 1 will be modified to inactivate endogenous MFα1 and MFα2. The resulting strain 3, MATα far1 sst2 ste3::STE2::ste3 FUS1::HIS3 mfa1 mfa2, should no longer display the selectable phenotype (i.e., the strain should be auxotrophic for histidine). Similarly, strain 2 will be modified to inactivate endogenous MFa1 and MFa2. The resulting strain 4, MATa far1 sst2 ste2::STE3::ste2 FUS1::HIS3 mfa1 mfa2, should be auxotrophic for histidine. The uses of strains 5 and 6 are outlined in Examples 3 and 4 below.

EXAMPLE 3

Peptide Library

In this example, a synthetic oligonucleotide encoding a peptide is expressed so that the peptide is secreted or transported into the periplasm.

i. The region of MFα1; which encodes mature α-factor has been replaced via single-stranded mutagenesis with restriction sites that can accept oligonucleotides with AflII and BglII ends. Insertion of oligonucleotides with AflII and BglII ends will yield plasmids which encode proteins containing the MFα1 signal and leader sequences upstream of the sequence encoded by the oligonucleotides. The MFα1 signal and leader sequences should direct the processing of these precursor proteins through the pathway normally used for the transport of mature α-factor.

The MFα1 gene, obtained as a 1.8 kb EcoRI fragment from pDA6300 (J. Thorner, Univ. of California) was cloned into pALTER (see FIG. 2) in preparation for oligonucleotide-directed mutagenesis to remove the coding region of mature α-factor while constructing sites for acceptance of oligonucleotides with AflII and BclI ends. The mutagenesis was accomplished using the minus strand as template and the following mutagenic oligonucleotide:

```
                                          (SEQ ID NO: 18)
5'CTAAAGAAGA AGGGGTATCT TTGCTTAAGC TCGAGATCTC

GACTGATAAC AACAGTGTAG 3'.
```

A HindIII site was simultaneously introduced 7 nts upstream of the MFα1 start codon with the oligonucleotide:
5' CATACACAAT ATAAAGCTTT AAAAGAATGA G 3' (SEQ ID NO:19).

The resulting plasmid, Cadus 1214, contains a HindIII site 7 nts upstream of the MFα1 initiation codon, an AflII site at the positions which encode the KEX2 processing site in the MFα1 leader peptide, and XhoI and BglII sites in place of all sequences from the leader-encoding sequences up to and including the normal stop codon. The 1.5 kb HindIII fragment of Cadus 1214 therefore provides a cloning site for oligonucleotides to be expressed in yeast and secreted through the pathway normally travelled by endogenous α-factor.

A sequence comprising the ADH1 promoter and 5' flanking sequence was obtained as a 1.5 kb BamHI-HindIII fragment from pAAH5 (Ammerer, G. (1983) "[11]. Expression of Genes in Yeast Using the ADCI Promoter", Academic Press, Inc., Meth. Enzymol. 101, 192-201 and ligated into the high copy yeast plasmid pRS426 (Christianson, T. W et al. (1992) "Multifunctional yeast high-copy-number shuttle vectors", Gene 110:119-122) (see FIG. 3). The unique XhoI site in the resulting plasmid was eliminated to yield Cadus 1186. The 1.5 Kb HindIII fragment of Cadus 1214 was inserted into HindIII-digested Cadus 1186; expression of sequences cloned into this cassette initiates from the ADH1 promoter. The resulting plasmid, designated Cadus 1215, can be prepared to accept oligonucleotides with AflII and BclI ends by digestion with those restriction endonucleases. The oligonucleotides will be expressed in the context of MFα1 signal and leader peptides (FIG. 4).

Modified versions of Cadus 1215 were also constructed. To improve the efficiency of ligation of oligonucleotides into the expression vector, Cadus 1215 was restricted with KpnI and religated to yield Cadus 1337. This resulted in removal of one of two HindIII sizes. Cadus 1337 was linearized with HindIII, filled-in, and recircularized to generate Cadus 1338. To further tailor the vector for library construction, the following double-stranded oligonucleotide was cloned into AflII- and BglII-digested Cadus 1338:

```
                                          (SEQ ID NO: 37)
5' TTAAGCGTGAGGCAGAAGCTTATCGATA      oligo 062

(SEQ ID NO: 38)
3'      CGCACTCCGTCTTCGAATAGCTATCTAG
oligo 063
```

The HindIII site is italicized and a ClaI site is emboldened; this ClaI site is unique in the resulting vector, Cadus 1373. In Cadus 1373, the HindIII site that exists at the junction between the MFα pro sequence and the mature peptide to be expressed by this vector was made unique. Therefore the HindIII site and the downstream BglII site can be used to insert oligonucleotides encoding peptides of interest. These modifications of Cadus 1215 provide an alternative to the use of the AflII site in the cloning of oligonucleotides into the expressions vector.

Cadus 1373 was altered further to permit elimination from restricted vector preparations of contaminating singly-cut plasmid. Such contamination could result in unacceptably high background transformation. To eliminate this possibility, approximately 1.1 kb of dispensable ADH1 sequence at the 5' side of the promoter region was deleted. This was accomplished by restruction of Cadus 1373 with SphI and BamHI, fill-in, and ligation; this maneuver regenerates the BamHI site. The resulting vector, Cadus 1624, was then restricted with HindIII and ClaI and an approximately 1.4 kb HindIII and ClaI fragment encoding lacZ was inserted to generate Cadus 1625. Use of HindIII- and BglII-restricted Cadus 1625 for acceptance of oligonucleotides results in a low background upon transformation of the ligation product into bacteria.

Two single-stranded oligonucleotide sequences (see below) are synthesized, annealed, and repetitively filled in, denatured, and reannealed to form double-stranded oligonucleotides that, when digested with AflII and BclI, can be ligated into the polylinker of the expression vector, Cadus 1215. The two single-stranded oligonucleotides have the following sequences: 5' G CTA CTT AAG CGT GAG GCA GAA GCT 3' (SEQ ID NO:20) and 5' C GGA TGA TCA (NNN)$_a$ AGC TTC TGC CTC ACG CTT AAG TAG C 3' (SEQ ID NO:21) where N is any chosen nucleotide and n is any chosen integer. Yeast transformed with the resulting plasmids will secrete—through the α-factor secretory pathway—peptides whose amino acid sequence is determined by the particular choice of N and n (FIG. 4).

Alternatively, the following single stranded oligonucleotides are used:

```
MFαNNK (76 mer):                          (SEQ ID NO: 39)
5'CTGGATGCGAAGATCAGCTNNKNNKNNKNNKN
NKNNKNNKNNKNNKNNKNNKNNKTGATCAGTCTGTGACGC 3'
and MFαMbo (17 mer):                          SEQ ID NO: 40)
5'GCGTCACAGACTGATCA 3'
```

When annealed the double stranded region is:
TGATCAGTCTGTGACGC (last 17 bases of SEQ ID NO:39)
ACTAGTCAGACACTGCG (SEQ ID NO:40 in 3' to 5' direction)

where the FokI site is underlined, the BbsI site is emboldened, and the MboI site is italicized. After fill-in using Taq DNA polymerase (Promega Corporation, Madison, Wis.), the double stranded product is restricted with BbsI and MboI and ligated to HindIII- and BglII-restricted Cadus 1373.

ii. The region of MFa1 which encodes mature a-factor will be replaced via single stranded mutagenesis with restriction sites that can accept oligonucleotides with XhoI and AflII ends. Insertion of oligonucleotides with XhoI and AflII ends will yield plasmids which encode proteins containing the MFa1 leader sequences upstream of the sequence encoded by the oligonucleotides. The MFa1 leader sequences should direct the processing of these precursor proteins through the pathway normally used for the transport of mature a-factor.

MFA1, obtained as a BamHI fragment from pKK1 (provided by J. Thorner and K. Kuchler), was ligated into the BamHI site of pALTER (Promega) (FIG. 5). Using the minus strand of MFA1 as template, a HindIII site was inserted by oligonucleotide-directed mutagenesis just 5' to the MFA1 start codon using the following oligonucleotide:
5'      CCAAAATAAGTACAAAGCTTTCCTAGAAATG CAACCATC (SEQ ID NO:22).

A second oligonucleotide was used simultaneously to introduce a short polylinker for later cloning of synthetic oligonucleotides in place of MFA1 sequences. These MFA1 sequences encode the C-terminal 5 amino acids of the 21 amino acid leader peptide through to the stop codon:

5' GCCGCTCCAAAAGAAAAGACCTCGAGCTCGCT-TAAGTTCTGCGTACA AAAACGTTGTTC 3' (SEQ ID NO:23). The 1.6 kb HindIII fragment of the resulting plasmid, Cadus 1172, contains sequences encoding the MFA1 start codon and the N-terminal 16 amino acids of the leader peptide, followed by a short polylinker containing XhoI, SacI, and AflII sites for insertion of oligonucleotides. The 1.6 kb HindIII fragment of Cadus 1172 was ligated into HindIII-digested Cadus 1186 (see above) to place expression of sequences cloned into this cassette under the control of the ADH1 promoter. The SacI site in the polylinker was made unique by eliminating a second SacI site present in the vector. The resulting plasmid, designated Cadus 1239, can be prepared to accept oligonucleotides with XhoI and AflII ends by digestion with those restriction endonucleases for expression in the context of MFa1 leader peptides (FIG. 6).

Two single-stranded oligonucleotide sequences (see below) are synthesized, annealed, and repetitively filled in, denatured, and reannealed to form double-stranded oligonucleotides that, when digested with AflII and BglII, can be cloned into the polylinker of the expression vector, Cadus 1239. The two single-stranded oligonucleotides used for the cloning have the following sequences:

```
                                              (SEQ ID NO: 24)
5' GG TAC TCG AGT GAA AAG AAG GAC AAC 3'

(SEQ ID NO: 25)
5' CG TAC TTA AGC AAT AAC ACA (NNN)n GTT
GTC CTT CTT TTC ACT CGA GTA CC 3'
``` where N is any chosen nucleotide and n is any chosen integer. Yeast transformed with the resulting plasmids will transport
- through the pathway normally used for the export of a-factor
- farnesylated, carboxymethylated peptides whose amino acid sequence is determined by the particular choice of N and n (FIG. 6).

EXAMPLE 4

Peptide Secretion/Transport

This example demonstrates the ability to engineer yeast such that they secrete or transport oligonucleotide-encoded peptides (in this case their pheromones) through the pathways normally used for the secretion or transport of endogenous pheromones.

Autocrine MATa Strain CY588:

A MATa strain designed for the expression of peptides in the context of MFα1 (i.e., using the MFα1 expression vector, Cadus 1215) has been constructed. The genotype of this strain, which we designate CY588, is MATa bar1 far1-1 fus1-HIS3 ste14::TRP1 ura3 trp1 leu2 his3. The bar1 mutation eliminates the strain's ability to produce a protease that degrades α-factor and that may degrade some peptides encoded by the cloned oligonucleotides; the far1 mutation abrogates the arrest of growth which normally follows stimulation of the pheromone response pathway; an integrated FUS1-HIS3 hybrid gene provides a selectable signal of activation of the pheromone response pathway; and, finally, the ste14 mutation lowers background of the FUS1-HIS3 readout. The enzymes responsible for processing of the MFα1 precursor. in MATα cells are also expressed in MATa cells (Sprague and Thorner, in *The Molecular and Cellular Biology of the Yeast Saccharomyces: Gene Expression*, 1992, Cold Spring Harbor Press), therefore, CY588 cells should be able to secrete peptides encoded by oligonucleotides expressed from plasmid Cadus 1215.

A high transforming version (tbt1-1) of CY588 was obtained by crossing CY1013 (CY588 containing an episomal copy of the STE14 gene) (MATa bar1::hisGfar1-1 fus1-HIS3 ste14::TRP1 ura3 trp1 leu2 his3 [STE14 URA3 CEN4]) to CY793 (MATα tbt1-1 ura3 leu2 trp1 his3 fus1-HIS2 can1 ste114::TRP1 [FUS1. LEU2 2μ]) and selecting from the resultant spores a strain possessing the same salient genotype described for CY588 (see above), and in addition the tb1-1 allele, which confers the capacity for very high efficiency transformation by electroporation. The selected strain is CY1455 (MATabar1::hisGfar1-1 fus1-HIS3 ste14::TRP1 tbt-1 ura3 trp1 leu2 his3).

Secretion of Peptides in the Context of Yeast α-Factor:

Experiments were performed to test: 1. the ability of Cadus 1215 to function as a vector for the expression of peptides encoded by synthetic oligonucleotides; 2. the suitability of the oligonucleotides, as designed, to direct the secretion of peptides through the α-factor secretory pathway; 3. the capacity of CY588 to secrete those peptides; and 4. the ability of CY588 to respond to those peptides that stimulate the pheromone response pathway by growing on selective media. These experiments were performed using an oligonucleotide which encodes the 13 amino acid α-factor; i.e., the degenerate, sequence $(NNN)_n$ in the oligonucleotide cloned into Cadus 1215 (see above) was specified (n=13) to encode this pheromone. CY588 was transformed with the resulting plasmid (Cadus 1219), and transformants selected on uracil-deficient medium were transferred to histidine-deficient medium supplemented with a range of concentrations of aminotriazole (an inhibitor of the HIS3 gene product that. serves to reduce background growth). The results, shown in FIG. 7, demonstrate that the synthetic oligonucleotide, expressed in the context of MFα1 by Cadus 1215, conferred upon CY588 an ability to grow on histidine-deficient media supplemented with aminotriazole. In summation, these data indicate that: 1. CY588 is competent for the secretion of a peptide encoded by the $(NNN)_n$ sequence of the synthetic oligonucleotide cloned into and expressed from Cadus 1215; and 2. CY588 can, in an autocrine fashion, respond to a secreted peptide which stimulates its pheromone response pathway, in this case by α-factor binding to STE2.

Additional experiments were performed to test the utility of autocrine yeast strains in identifying agonists of the Ste2 receptor from among members of two semi-random α-factor libraries, α-Mid-5 and MFα-8.

α-Mid-5 Library

A library of semi-random peptides, termed the α-Mid-5 library, was constructed. In this library, the N-terminal four amino acids and the C-terminal four amino acids of a 13 residue peptide are identical to those of native α-factor while the central five residues (residues 5-9) are encoded by the degenerate sequence $(NNQ)_5$. The following oligonucleotides were used in the construction of the α-Mid-5 library:

```
(1) MFαMbo a 17 mer:              (SEQ ID NO: 40)
5'GCGTCACAGACTGATCA
```

-continued (2) MID5ALF, a 71 mer:    (SEQ ID NO: 41)
5' GCCGTCAGTA<u>AAGCTT</u>GGCATTGGTTGNN
QNNQNNQNNQMMQCAGCCTATGTACTGATCAG
TCTGTGACGC Sequenase (United States Biochemical Corporation, Cleveland, Ohio) was used to complete the duplex formed after annealing MFαMbo to the MID5ALF oligonucleotide. In the MID5ALF sequence, N indicates a mixture of A, C, G, and T at ratios of 0.8:1:1.3:1; Q indicates a mixture of C and G at a ratio of 1:1.3. These ratios were employed to compensate for the different coupling efficiencies of the bases during oligonucleotide synthesis and were thus intended to normalize the appearance of all bases in the library. In the oligonucleotide sequences above, the HindIII site is underlined and the MboI site is emboldened. The double-stranded oligonucleotide was restricted with HindIII and MboI and ligated to Cadus 1625 (see above); Cadus 1625 had been prepared to accept the semi-random oligonucleotides by restriction with HindIII and BglII.

The apparent complexity of the αMid-5 library is 1×10$^7$. This complexity is based on the number of bacterial transformants obtained with the library DNA versus transformants obtained with control vector DNA that lacks insert. Sequence analysis of six clones from the library demonstrated that each contained a unique insert.

To identify peptide members of the α-Mid-5 library that could act as agonists on the STE2 receptor, CY1455, a high transforming version of CY588, was electroporated to enhance uptake of α-Mid-5 DNA. Transformants were selected on uracil-deficient (–Ura) synthetic complete medium and were transferred to histidine-deficient (–His) synthetic complete medium supplemented with 0.5mM or 1 mM aminotriazole.

Yeast able to grow on –His+aminotriazole medium include (1) yeast which are dependent on the expression of an αfactor variant agonist and (2) yeast which contain mutations that result in constitutive signalling along the pheromone pathway. Yeast expressing and secreting a variant STE2 receptor agonist have the ability to stimulate the growth on –His medium of surrounding CY 1455 cells that do not express such an agonist. Thus a recognizable formation (termed a "starburst") results, consisting of a central colony, growing by virtue of autocrine stimuation of the pheromone pathway, surrounded by satellite colonies, growing by virtue of paracrine stimulation of the pheromone pathway by the agonist peptide as that peptide diffuses radially from the central, secreting colony.

In order to identify the peptide sequence responsible for this "starburst" phenomenon, yeast were transferred from the center of the "starburst" and streaks were made on –Ura medium to obtain single colonies. Individual clones from –Ura were tested for the His$^+$ phenotype on –His+aminotriazole plates containing a sparse lawn of CY1455 cells. Autocrine yeast expressing a peptide agonist exhibited the "starburst" phenotype as the secreted agonist stimulated the growth of surrounding cells that lacked the peptide but were capable of responding to it. Constitutive pheromone pathway mutants were capable of growth on –His+aminotriazole but were incapable of enabling the growth of surrounding lawn cells.

Alternatively, streaks of candidate autocrine yeast clones were made on plates containing 5-fluoroorotic acid (FOA) to obtain Ura segregants were retested on –His+aminotriazole for the loss of the His$^+$ phenotype. Clones that lost the ability to grow on –His+aminotriazole after selection on FOA (and loss of the peptide-encoding plasmid) derived from candidate expressors of a peptide agonist. The plasmid was rescued from candidate clones and the peptide sequences determined. In addition, a plasmid encoding a putative Ste2 agonist was reintroduced into CY1455 to confirm that the presence of the plasmid encoding the peptide agonist conferred the His$^+$ phenotype to CY1455.

By following the above protocol novel Ste2 agonists have been identified from the α-Mid-5 library. Sequences of nine agonists follow, preceded by the sequence of the native α-factor pheromone and by the oligonucleotide used to encode the native pheromone in these experiments. (Note the variant codons used in the α-factor-encoding oligonucleotide for glutamine and proline in the C-terminal amino acids of α-factor). Below each nucleotide sequence is the encoded amino acid sequence with variations from the native-pheromone underlined.

```
α-factor TGG CAT TGG TTG CAG CTA AAA CCT GGC  CAA CCA ATG TAC
encodes  Trp His Trp Leu Gln Leu Lys Pro Gly Gln Pro Met Tyr
         (DNA, SEQ ID NO: 42, AAS, SEQ ID NO: 43)

α-factor TGG CAT TGG TTG CAG CTA AAA CCT GGC CAG CCT ATG TAC
oligo:
encodes  Trp His Trp Leu Gln Leu Lys Pro Gly Gln Pro Met Tyr
         (DNA, SEQ ID NO: 91, AAS, SEQ ID NO: 92)

M1       TGG CAT TGG TTG TCC TTG TCG CCC GGG CAG CCT ATG TAC
encodes  Trp His Trp Leu Ser Leu Ser Pro Gly Gln Pro Met Tyr
         (DNA, SEQ ID NO: 93, AAS, SEQ ID NO: 94)

M2       TGG CAT TGG TTG TCC CTG GAC GCT GGC CAG CCT ATG TAC
encodes  Trp His Trp Leu Ser Leu Asp Ala Gly Gln Pro Met Tyr
         (DNA, SEQ ID NO: 95, AAS, SEQ ID NO: 96)

M3       TGG CAT TGG TTG ACC TTG ATG GCC GGG CAG CCT ATG TAC
encodes  Trp His Trp Leu Thr Leu Met Ala Gly Gln Pro Met Tyr
         (DNA, SEQ ID NO: 97, AAS, SEQ ID NO: 98)

M4       TGG CAT TGG TTG CAG CTG TCG GCG GGC CAG CCT ATG TAC
encodes  Trp His Trp Leu Gln Leu Ser Ala Gly Gln Pro Met Tyr
         (DNA, SEQ ID NO: 99, AAS, SEQ ID NO: 100)
```

-continued

```
M5      TGG CAT TGG TTG AGG TTG CAG TCC GGC CAG CCT ATG TAC
encodes Trp His Trp Leu Arg Leu Gln Ser Gly Gln Pro Met Tyr
        (DNA, SEQ ID NO: 101, AAS, SEQ ID NO: 102)

M6      TGG CAT TGG TTG CGC TTG TCC GCC GGG CAG CCT ATG TAC
encodes Trp His Trp Leu Arg Leu Ser Ala Gly Gln Pro Met Tyr
        (DNA, SEQ ID NO: 103, AAS, SEQ ID NO: 104)

M7      TGG CAT TGG TTG TCG CTC GTC CCG GGG CAG CCT ATG TAC
encodes Trp His Trp Leu Ser Leu Val Pro Gly Gln Pro Met Tyr
        (DNA, SEQ ID NO: 105, AAS, SEQ ID NO: 106)

M8      TGG CAT TGG TTG TCC CTG TAC CCC GGG CAG CCT ATG TAC
encodes Trp His Trp Leu Ser Leu Tyr Pro Gly Gln Pro Met Tyr
        (DNA, SEQ ID NO: 107, AAS, SEQ ID NO: 108)

M9      TGG CAT TGG TTG CGG CTG CAG CCC GGG CAG CCT ATG TAC
encodes Trp His Trp Leu Arg Leu Gln Pro Gly Gln Pro Met Tyr
        (DNA, SEQ ID NO: 109, AAS, SEQ ID NO: 110)
```

The nine peptide agonists of the Ste2 receptor above were derived from one electroporation of CY1455 using 1 µg of the α-Mid-5 library DNA. Approximately 3×10⁵ transformants were obtained, representing approximately 0.03% of the sequences present in that library.

MFα-8 Library

A semi-random α-factor library was obtained through synthesis of mutagenized α-factor oligonucleotides such that 1 in 10,000 peptide products were expected to be genuine α-factor. The mutagenesis was accomplished with doped synthesis of the oligonucleotides: each nucleotide was made approximately 68% accurate by synthesizing the following two oligos:

5' CTGGATGCGA AGACTCAGCT (20 mer) (oligo060)
(SEQ ID NO:44) where the FokI site is underlined and the BbsI site is emboldened.

```
5' CGGATGATCA gta cat tgg ttg gcc   (SEQ ID NO: 45)
agg ttt tag ctg caa cca atg cca
AGC TGA GTC TTC GCA TCC AG
(69 mer) (oligo074)
``` where the BclI site is italicized, the FokI site is underlined, the BbsI site is emboldened. The lower case letters indicate a mixture of 67% of that nucleotide and 11% of each of the other three nucleotides (e.g. t indicates 67% T and 11% A, 11% C, and 11% G). Note that digestion of the double-stranded oligonucleotide by FokI or BbsI will yield an identical 5' end that is compatible with HindIII ends.

Oligos 060 and 074 will form the following double-stranded molecule when annealed:

```
                                    (SEQ ID NO: 44)
5' CTGGATGCGAAGACTCAGC T (SEQ ID NO: 45)
3' GACCTACGCTTCTGAGTCGA acc gta acc aac gtc gat ttt
gga ccg gtt ggt tac atg ACTAGTAGGC 5'
```

The duplex was repetitively filled-in using Taq DNA polymerase (Promega Corporation, Madison, Wis.). The double-stranded product was restricted with BbsI and BclI and ligated into HindIII- and BglII-digested Cadus 1373. The BglII/BclI joint creates a TGA stop codon for the termination of translation of the randomers. Using this approach, the MFα-5.8 library (a library of apparent low complexity based on PCR analysis of oligonucleotide insert frequency) was constructed. To identify peptide members of the MFα-5.8 library that could act as agonists on the STE2 receptor, CY1455, a high transforming version of CY588, was electroporated to enhance uptake of MFα-5.8 DNA. Transformants were selected on uracil-deficient (–Ura) synthetic complete medium and were transferred to histidine-deficient (–His) synthetic complete medium supplemented with 1.0 mM or 2.5 mM aminotriazole. Yeast from colonies which were surrounded by satellite growth were transferred as streaks to –Ura medium to obtain single colonies. Yeast from single colonies were then tested for the His⁺ phenotype on –His+aminotriazole plates. Sequence analysis of seven of the plasmids rescued from His⁺ yeast revealed three unique α-factor variants that acted as agonists on the STE2 receptor. 1.4 independent clones had the following sequence:

```
                                              (SEQ ID NO: 46)
TGG CAT TGG CTA CAG CTA ACG CCT GGG CAA CCA ATG TAC
encoding
                                              (SEQ ID NO: 47)
Trp His Trp Leu Gln Leu Thr Pro Gly Gln Pro Met Tyr
```

2.2 independent clones had the following sequence:,

```
TGG CAT TGG CTG GAG CTT ATG CCT    (SEQ ID NO: 48)
GGC CAA CCA TTA TAC
encoding Trp His Trp Leu Glu Leu Met Pro    (SEQ ID NO: 49)
Gly Gln Pro Leu Tyr
```

3.

```
3.                                  (SEQ ID NO: 50)
TGG CAT TGG ATG GAG CTA AGA CCT
GGC CAA CCA ATG TAC
encoding
                                    (SEQ ID NO: 51)
Trp His Trp Met Glu Leu Arg Pro
Gly Gln Pro Met Tyr
```

Autocrine Mata Strain CY599:

A MATa strain designed for the expression of peptides in the context of MFA1 (i.e., using the MFA1 expression vector, Cadus 1239) has been constructed. The genotype of this strain, designated CY599, is MATa mfa1 mfa2 far1-1 his3::fus1-HIS3 ste2-STE3 ura3 met1 ade1 leu2. In this strain, Cadus 1147 (see above) was used to replace STE2 with a hybrid gene in which the STE3 coding region is under the control of expression elements which normally drive the expression of STE2. As a result, the a-factor receptor replaces the α-factor receptor. The genes which encode a-factor are deleted from this strain, the far1 mutation abrogates the arrest of growth which normally follows stimulation of the pheromone response pathway; and the FUS1-HIS3 hybrid gene (integrated at the HIS3 locus) provides a selectable signal of activation of the pheromone response pathway. CY599 cells were expected to be capable of the transport of a-factor or a-factor-like peptides encoded by oligonucleotides expressed from Cadus 1239 by virtue of expression of the endogenous yeast transporter, Ste6.

Transport of Peptides by the Yeast a-Factor Pathway:

Experiments were performed to test: 1. the ability of Cadus 1239 to function as a vector for the expression of peptides encoded by synthetic oligonucleotides; 2. the suitability of the oligonucleotides, as designed, to direct the export of farnesylated, carboxymethylated peptides through the pathway normally used by a-factor; 3. the capacity of CY599 to export these peptides; and 4. the ability of CY599 to respond to those peptides that stimulate the pheromone response pathway by growing on selective media. These tests were performed using an oligonucleotide which encodes the 12 amino acid a-factor; specifically, the degenerate sequence $(NNN)_n$ in the oligonucleotide cloned into Cadus 1239 (see above) (with n=12) encodes the peptide component of a-factor pheromone. CY599 was transformed with the resulting plasmid (Cadus 1220), and transformants selected on uracil-deficient medium were transferred to histidine-deficient medium supplemented with a range of concentrations of aminotriazole. The results, shown in FIG. 8, demonstrate that the synthetic oligonucleotide, expressed in the context of MFA1 by Cadus 1220, conferred upon CY599 enhanced aminotriazole-resistant growth on histidine-deficient media. In summation, these data indicate: 1. Cadus 1220 and the designed oligonucleotide are competent to direct the expression and export of a farnesylated, carboxymethylated peptide encoded by the $(NNN)_n$ sequence of the synthetic oligonucleotide; and 2. CY599 can, in an autocrine fashion, respond to a farnesylated, carboxymethylated peptide that stimulates its pheromone response pathway, in this case signaling initiates as a-factor binds to STE3.

EXAMPLE 5

Proof of Concept

This example will demonstrate the utility of the autocrine system for the discovery of peptides which behave as functional pheromone analogues. By analogy, this system can be used to discover peptides that productively interact with any pheromone receptor surrogates.

CY588 (see strain 5, Example 2 above) will be transformed with CADUS 1215 containing oligonucleotides encoding random tridecapeptides for the isolation of functional α-factor analogues (FIG. 4). CY599 (see strain 6, Example 2 above) will be transformed with CADUS 1239 containing oligos of random sequence for the isolation of functional a-factor analogues (FIG. 6). Colonies of either strain which can grow on histidine-deficient media following transformation will be expanded for the preparation of plasmid DNA, and the oligonucleotide cloned into the expression plasmid will be sequenced to determine the amino acid sequence of the peptide which presumably activates the pheromone receptor. This plasmid will then be transfected into an isogenic strain to confirm its ability to encode a peptide which activates the pheromone receptor. Successful completion of these experiments will demonstrate the potential of the system for the discovery of peptides which can activate membrane receptors coupled to the pheromone response pathway.

Random oligonucleotides to be expressed by the expression plasmid CADUS 1215 will encode tridecapeptides constructed as 5' CGTGAAG<u>CTTAAG</u>CGTGAGGCAGAAGCT(NNK)$_{13}$<u>TGATCA</u>TCCG, (SEQ ID NO:6) where N is any nucleotide, K is either T or G at a ratio of 40:60 (see Proc Natl Acad Sci 87:6378, 1990; ibid 89:5393, 1992), and the AflII and BclI sites are underlined. This oligonucleotide is designed such that: the AflII and BclI sites permit inserting the oligos into the AflII and BglII site of CADUS 1215 (see FIG. 4); the HindIII site just 5' to the AfLII site in the 5' end of the oligo allows future flexibility with cloning of the oligos; the virtual repeat of GAGGCT (SEQ ID NO: 131) and the GAGA (SEQ ID NO: 132) repeats which are present in the wild-type sequence and which can form triple helices are changed without altering the encoded amino acids. The random oligonucleotides described above will actually be constructed from the following two oligos:

5' CGTGAAGCTTAAGCGTGAGGCAGAAGCT    (SEQ ID NO: 26)
and

5' CGGATGATCA(MNN)$_{13}$AGCTTCTG,    (SEQ ID NO: 27)

where M is either A or C at a ratio of 40:60. The oligos will be annealed with one another and repetitively filled in, denatured, and reannealed (Kay et al, Gene, 1993). The double-stranded product will be cut with AflII and BclI and ligated into the AflII-and BglII-digested CADUS 1215. The BglII/BclI joint will create a TGA stop codon for termination of translation of the randomers (FIG. 4). Because of the TA content of the Afl overhang, the oligos will be ligated to the AflII-and BglII-digested pADC-MFα at 4° C.

Random oligonucleotides to be expressed by the expression plasmid CADUS 1239 will encode monodecapeptides constructed as 5' GGTA<u>CTCGAG</u>TGAAAAGAAGGACAAC(NNK)$_{11}$TG TGTTATTG<u>CTTAAG</u>TACG (SEQ ID NO:12), where N is any nucleotide, K is either T or G at a ratio of 40:60 (see Proc Natl Acad set 87:6378, 1990; ibid 89:5393, 1992), and the XhoI and AflII sites are underlined. When cloned into the XhoI and AflII sites of CADUS 1239 the propeptides expressed under the control of the ADH1 promoter will contain the entire leader peptide of MFa1, followed by 11 random amino acids, followed by triplets encoding CVIA (the C-terminal tetrapeptide of wild-type a-factor). Processing of the propeptide should result in the secretion of dodecapeptides which contain 11 random amino acids followed by a C-terminal, farnesylated, carboxymethylated cysteine.

Using the procedure described above, the oligonucleotides for expression in CADUS 1239 will actually be constructed from the following two oligos:

5' GGTACTCGAGTGAAAAGAAGGACAAC and    (SEQ ID NO: 28)

5' CGTACTTAAGCAATAACAca(MNN)$_{11}$GTT    (SEQ ID NO: 29)
GTCC, where M is either A or C at a ratio of 40:60, and the XhoI and AflII sites are underlined.

Discovery of a-Factor Analogues from a Random Peptide Library

An optimized version of strain 6 (Example 2 above) was derived. This yeast strain, CY2012 (MATa ste2-STE3 far1Δ1442 mfa1::LEU2 mfa2-lacZ fus1-HIS3 tbt1-1 ura3 leu2 his3 trp1 suc2), was constructed as follows. From a cross of CY570 (MATa mfa1::LEU2 mfa2-lacZ ura3 trp1 his3Δ200 can1 leu2 fus1-HIS3 [MFA1 URA3 2μ] [FUS1Δ8-73 TRP1 CEN6]) by CY1624 (MATα tbt1-1 fus1-HIS3 trp1 ura3 leu2 his3 lys2-801 SUC+), a spore was selected (CY1877) of the following genotype: MATa mfa1::LEU2 mfa2-lacZ fus1-HIS3 tbt1-1 ura3 leu2 his3 trp1 suc2. This strain lacks both genes (MFA1 and MFA2) encoding a-factor precursors, contains the appropriate pheromone pathway reporter gene (fus1-HIS3), and transforms by electroporation at high efficiency (tbt1-1). This strain was altered by deletion of the FAR1 gene (with Cadus 1442; see Example 6), and replacement of STE2 coding sequences with that of STE3 (see Example 1) to yield CY2012.

This strain was transformed with plasmid DNA from a random a-factor library by electroporation and plated on 17 synthetic complete plates lacking uracil (–Ura), yielding approximately $10^5$ Ura$^+$ colonies per plate after 2 days at 30° C. These colonies were replica plated to histidine-deficient synthetic complete media (–His) containing 0.2 mM 3-aminotriazole and after three days at 30° C. 35 His$^+$ replicas were streaked to –Ura plates. The resultant colonies, 3 from each isolate, were retested for their His$^+$ phenotype, and streaked to 5-fluoroorotic acid plates to obtain Ura$^-$ segregants (lacking a library plasmid). Those Ura$^-$ segregants were tested for the loss of their His$^+$ phenotype. Ten of the original isolates passed these tests; in two cases only one of the three Ura$^+$ colonies purified from the isolate retained the His$^+$ phenotype, but nevertheless subsequently segregated Ura$^-$ $^{His-}$ colonies.

A single plasmid (corresponding to a bacterial colony) was obtained from each of the ten isolates, and reintroduced into CY2012. Eight of the ten plasmids passed the test of retaining the ability to confer the His$^+$ phenotype on CY2012 (the two that failed correspond to the two isolates that were mentioned above, suggesting that these isolates contain at least one "irrelevant" plasmid). Sequencing of the randomized insert in the eight plasmids of interest revealed that four contain the sequence:

```
TAT GCT CTG TTT GTT CAT TTT TTT   (SEQ ID NO: 52)
GAT ATT CCG

Tyr Ala Leu Phe Val His Phe Phe   (SEQ ID NO: 53)
Asp Ile Pro,
``` two contain the sequence:

```
TTT AAG GGT CAG GTG CGT TTT GTG   (SEQ ID NO: 54)
GTT CTT GCT

Phe Lys Gly Gln Val Arg Phe Val   (SEQ ID NO: 55)
Val Leu Ala,
``` and two contain the sequence:

```
CTT ATG TCT CCG TCT TTT TTT TTT   (SEQ ID NO: 56)
TTG CCT GCG

Leu Met Ser Pro Ser Phe Phe Phe   (SEQ ID NO: 57)
Leu Pro Ala
```

Clearly, these sequences encode novel peptides, as the native a-factor sequence differs considerably:

Tyr Ile Ile Lys Gly Val Phe Trp Asp Pro Ala (SEQ ID NO: 133).

The a-factor variants identified from random peptide libraries have utility as "improved" substrates of ABC transporters expressed in yeast. For example, identification of a preferred substrate of human MDR, one that retains agonist activity on the pheromone receptor, would permit the establishment of robust yeast screens to be used in the discovery of compounds that affect transporter function.

EXAMPLE 6

Drug Screens Designed to Permit Discovery of Molecules which Modulate the Function of ATP-dependent Transmembrane Transporters:

The availability of cloned DNA encoding the related proteins human Mdr1, human CFTR and human MRP, will allow the construction of yeast strains expressing these molecules. The resultant strains will be essential to the design of microbiological assays which can be used to probe the function of these proteins and to discover molecules capable of inhibiting or enhancing their function in cellular resistance to chemotherapeutics or in ion transport. The present assay makes use of the transport of the yeast mating pheromone a-factor from autocrine yeast expressing a human protein capable of substituting for yeast Ste6.

A. MFa1- and Mdr1-Containing Plasmids Obtained from Karl Kuchler (University of Vienna) for Use in These Experiments:

(1) pYMA177 (denoted Cadus 1067), see FIG. 9.

(2) pKK1 includes sequence encoding MFa1 in YEp351; a-factor is overexpressed from this plasmid due to increased plasmid copy number (3) pHaMDR1(wt) provides wild type Mdr1 cDNA in a retroviral vector (initially obtained from Michael Gottesman, NIH).

B. Plasmids Constructed at Cadus for Use in These Experiments:

A 1.5 kb BamHI-BglII fragment which includes MFa1 sequence was derived from pYMA177 and ligated to BamHI-digested pYMA177 to yield Cadus 1079. Cadus 1079 was digested with BglII and recircularized to delete a 950 bp fragment containing sequence encoding the G185V mutant of human Mdr1; the resultant plasmid is Cadus 1093. pHaMDR1 was digested with BglII to allow isolation of a 965 bp fragment containing wild type human Mdr1 (G185) sequence. The 965 bp BglII fragment was inserted into BglII-digested Cadus 1093 to yield Cadus 1097. The Cadus 1097 construct was verified by sequencing using dideoxy nucleotides. To yield Cadus 1164, pYMA177 was digested with BamHI and recircularized to eliminate the sequence encoding MFa1. Cadus 1165 was constructed by ligating a 700 bp BglII-BamHI fragment from pYMA177 to the large BamHI to BglII fragment of pYMA177. This results in the removal of both the 1.6 kb MFa BamHI fragment and the 965 bp BglII fragment encoding human Mdr1 (G185V); the resulting plasmid is Cadus 1165.

Cadus 1176 resulted from the ligation of a 965 bp BglII fragment from pHaMDR1, containing sequence encoding wild type human Mdr1, to BglII-digested Cadus 1165.

pRS426 (Cadus 1019) served as a URA3 control plasmid.

The final plasmid array used in these experiments is as follows:

|  | no Mdr1 | mutant Mdr1 (G185V) | wt Mdr1 (G185) |
|---|---|---|---|
| a-factor overexpression | 1065 | 1079 | 1097 |
| no a-factor overexpression | 1019 | 1164 | 1176 |

Evidence for the Expression of Human Mdr1 Constructs in Yeast.

CADUS plasmids 1065, 1079 and 1097 as well as a URA3 control plasmid (pRS426=1019) were transformed into a ura3⁻, ste6⁻ strain of yeast (WKK6=CY20=MATa ura3-1 leu2-3,112 his3-11,15 trp1-1 ade2-1 can1-100 ste6::HIS3, obtained from Karl Kuchler). Individual transformants were grown overnight in SD-URA media and lawns containing approximately $5\times10^6$ cells were poured onto YPD plates in 3 ml of YPD top agar. Sterile filter disks were placed on the plates after the top agar had solidified, and 5 ml of DMSO or 5 mM valinomycin in DMSO were spotted onto the filter disks. By this assay, expression of mutant Mdr1 from plasmid 1079 in WKK6 cells conferred weak resistance to valinomycin while expression of wild type Mdr1 from plasmid 1097 conferred complete resistance.

Attempts to Assay Mdr1 Activity by a-factor Transport in a Two Cell System.

Several attempts to demonstrate mating of WKK6 transformed with the various human Mdr1 constructs failed. This is in contrast to published experiments utilizing the mouse mdr3 gene, in which a partial complementation of mating deficiency was seen (Raymond et al., 1992).

A "halo" assay was performed by patching WKK6 cells containing the various Mdr1 constructs (1019, 1065, 1079 & 1097) onto a lawn of Matα cells which are supersensitive to a-factor (CY32=MATα leu2-3; 112 trp1-289 ura3-52 his3*1 sst2*2 GAL+). Although all halos were much smaller than those produced by STE6⁺ cells, a small difference in halo size was observed with the relative order 1097>1079~1065>1019. This indicates that a-factor can be transported by the wild-type human Mdr1 protein expressed in yeast deleted for STE6, however, the halo assay does not appear to be amenable to rapid drug screening.

The halo assay detects a-factor secreted from ste6⁻ Mdr1 strains by growth arrest of cells present in the indicator lawn. An alternative, and potentially more sensitive, method makes use of the transcriptional response to pheromone signaling. A strain with an a-factor responsive HIS3 gene (CY104=MATα ura3 leu2 trp1 his3 fus1-HIS3 can1 ste14::TRP1) was cross-streaked with STE6⁺ (CY19=W303-1a=MATa ura3-1 leu2-3,112 his3-11,15 trp1-1 ade2-1 can1-100) or ste6⁻ (WKK6=CY20=MATa ura3-1 leu2-3,112 his3-11,15 trp1-1 ade2-1 can1-100 ste6::HIS3) strains containing various plasmids. The cross-streaking was performed on a plate lacking histidine and tryptophan so that only the CY104 indicator strain would grow if stimulated by a-factor. The order of a-factor secretion seen by this method was CY58>CY61≈CY62≈CY63>CY60 where: CY58=CY19 (STE6⁺, 1019), CY60=CY20(ste6⁻, 1019), CY61=CY20 (ste6⁻, 1065), CY62=CY20(ste6⁻, 1079) and CY63=CY20 (ste6⁻, 1097). Thus, the difference in a-factor production between STE6+and ste6 and between a-factor overproduction or not is detectable in this system, whereas the activity of Mdr1 in secreting a-factor is not. It was not clear from these experiments: whether the signal generated from the ste6⁻, a-factor overproducing strains was due to an alternate pathway for a-factor secretion or the release of a-factor from lysed cells.

Assay of Mdr1 Activity by a-Factor Transport in an Autocrine System.

A single strain system for the detection of Mdr1-mediated a-factor transport was constructed in order to improve sensitivity and reproducibility and to circumvent the potential false signal of a-factor release from lysed cells (a cell concentration-dependent phenomenon). A strain was constructed (CY293=MATa ura3 leu2 trp1 his3 fus1-HIS3 can1 ade2-1 ste2-STE3 ste6::TRP1) which could respond to a-factor by growing on media lacking histidine and in which the only impediment to the secretion of a-factor is the lack of a functional STE6 gene. Indeed, the immediate precursor to this strain, which did contain a functional STE6 gene, was able to grow vigorously on –HIS media containing 3 mM aminotriazole, whereas CY293 did not grow at all. The addition of aminotriazole, a competitive inhibitor of the HIS3 enzyme, is necessary to reduce the background growth of these strains.

The Mdr1-containing plasmids were introduced into CY293, and the transformants were streaked onto -HIS plates containing either 0.1 or 0.33 mM aminotriazole. The growth pattern thus generated was 1097>1067>1065≈1176>1164≈1019. The STE6⁺ parent of CY293 exhibited a much more vigorous growth than any of these transformants. However, human Mdr1-mediated a-factor secretion is clearly detectable in this autocrine system. CY293 transformed with 1097 can be used to screen for drugs which enhance the activity of the Mdr1 protein (increased growth on –HIS +aminotriazole) as well as drugs which inhibit Mdr1 activity (decreased growth on –HIS+aminotriazole). In the latter case, controls must be designed to identify compounds which inhibit yeast growth in an Mdr1-independent fashion.

Additional strains, with improvements over CY293 (see example 6 [76-35]) for the expression of mammalian ABC transporters were constructed. These strains contain the tbt1-1 allele, conferring high-efficiency transformation by electroporation, and a lesion in the FAR1 gene. In addition, they are auxotrophic for tryptophan, and hence can serve as hosts for TRP1-based plasmids.

Two starting strains were selected, CY1555 (MATa tbt1-1 fus1-HIS3 trp1 ura3 leu2 his3 lys2-801 SUC+) and CY1557 (MATa tbt1-1 fus1-HIS3 trp1 ura3 leu2 his3 suc2). A plasmid containing an internal deletion of FAR1 was constructed by amplifying genomic sequences corresponding to the 5' end and the 3' end of FAR1, and ligating them together in pRS406 (an integrative vector containing the URA3 gene), thereby creating a deletion from the 50th to the 696th predicted codon of FAR1. The oligonucleotides used for amplification were:

for the 5' segment of FAR1:

```
5'-CGGGATCCGATGCAATT    (23FAR1)      (SEQ ID NO: 58)
TTCAACATGC-3' and

5'-GCTCTAGATGCTACTGA    (1RAF616)     (SEQ ID NO: 59)
TCCCGC-3' and for the 3'
segment of FAR1:
5'-CGCCGCATGACTCCATT    (2552FAR1)    (SEQ ID NO: 60)
G-3' and

5'-GGGGTACCAATAGGTTC    (1RAF2979)    (SEQ ID NO: 61)
TTTCTTAGG-3'.
```

The resultant amplification products were restricted with BamHI and XbaI (5' segment; 0.6 kb) or NheI and KpnI (3' segment; 0.4 kb), and ligated into pRS406 (Cadus 1011) that had been restricted with BamHI and KpnI. The resultant plasmid (Cadus 1442) was restricted with EcoRI to direct integration at the FAR1 locus, Ura+ transformants were purified and subjected to selection on 5-fluoro-orotic acid, and Ura− clones were screened for the impaired mating ability conferred by the far1 deletion. The STE6 gene was subsequently deleted using the ste6::hisG-URA3 plasmid (Cadus 1170; constructed by Karl Kuchler), and the STE2 coding sequences were replaced with STE3 coding sequences as described in Example 1. The resultant strains were named CY1880 (MATa ste2-STE3 ste6::hisG far1Δ1442 tbt1-1 fus1-HIS3 trp1 ura3 leu2 his3 suc2 ) and CY1882 (MATa ste2-STE3 ste6::hisG far1Δ1442 tbt1-1 fus1-HIS3 trp1 ura3 leu2 his3 lys2-801 SUC+).

Like strain CY293 these strains show a dramatic enhancement of growth (via the fus1-HIS3 reporter gene) under conditions of histidine starvation when transformed with the MDR1-encoding plasmids Cadus 1097 and Cadus 1176 (as compared to control plasmids lacking MDR1, Cadus 1065 and 1019). In addition, these strains display more robust general growth, transform by electroporation at high efficiency (the tbt1-1 effect), lack susceptibility to pheromone-induced growth arrest (due to inactivation of FAR1), and act as hosts for TRP1-based plasmids (ste6::hisG instead of ste6::TRP1).

These strains also act as suitable hosts for the STE6-CFTR chimeras constructed by Teem et al. (1993) (see Example 7). When compared with CY293 in their ability to distinguish between wild type and ΔF508 STE6-CFTR in their ability to transport a-factor, a similar enhancement is seen:

| Host strain | wild type/ΔF508 growth ratio |
|---|---|
| CY293 | 18 |
| CY1880 | 7 |
| CY1882 | 8 |

The strains were transformed with Cadus 1515 (STE6-CFTR (H5) URA3 CEN) or 1516 (STE6-CFTR(H5)ΔF508 URA3 CEN) and inoculated at various cell densities ($OD_{600}$=0.003 to 0.048) into histidine-free media containing various concentrations of 3-aminotriazole (0 to 1.2 mM). After overnight growth in microtiter wells the optical densities at 600 nm of the wells were measured, and ratios for wild type vs. ΔF508 calculated. The ratios reflect the highest ratios obtained in this experiment but not necessarily the highest ratio it would be possible to obtain.

Improvements on the Autocrine Yeast Expressing Mdr1.

The results described above indicate that the human Mdr1 protein transports a-factor less efficiently than does the yeast STE6 protein. Attempts will be made to isolate mutant a-factor molecules which are transported more efficiently by human Mdr1 and yet which retain agonist activity on the a-factor receptor (STE3 protein). To do this, a-factor coding sequences will be chemically synthesized using "dirty" nucleotides and inserted into an a-factor expression cassette. An example of "dirty" synthesis would be to incorporate nucleotide from a mixture of 70% G and 10% each of A, T and C at a position in the a-factor sequence where G would normally appear. Using oligonucleotides generated in this manner, a diverse library of peptides can be expressed in yeast and screened to identify those peptides which retain the ability to signal to the STE3 protein but which are also a favorable substrate for transport by human Mdr1.

A second improvement to the system will be the addition of a pheromone-inducible "negative selection" marker. For instance, the FUS1 promoter can be connected to GAL1 coding sequences. Expression of GAL1 is toxic in the presence of galactose in strains which contain mutations in either the GAL7 or GAL10 genes. In the context of an autocrine Mdr1 strain, this selection system should render cells galactose-sensitive. Addition of a compound which inhibits the ability of the Mdr1 protein to secrete a-factor would allow this strain to grow on galactose-containing media. This selection system would also eliminate false positives due to lethality. Controls must still be designed to identify compounds which interfere at other points in the pheromone response pathway.

The third improvement in the system involves inactivation of yeast genes which function equivalently to mammalian MDR genes. A network of genes involved in pleiotropic drug resistance (PDR) have been identified in yeast. This modification will be useful in any yeast screen designed to assay the interaction of compounds with intracellular targets. The improved autocrine yeast strain, expressing human Mdr1, will be used to screen compound libraries for molecules which inhibit the transport function of this protein. In addition, Mfα expression cassettes containing oligonucleotides encoding random peptides will be expressed in the autocrine Mdr1 strain to identify peptides capable of inhibiting the transport of a-factor, or an a-factor analogue by Mdr1.

EXAMPLE 7

Identification of an Analogue of Yeast a-factor that is Transported by Wild Type Human CFTR This example describes the use of autocrine yeast strains to identify molecules capable of enhancing transport by dysfunctional ATP-dependent transmembrane transporters, e.g. mutant human CFTR proteins. The wild type human CFTR protein will not substitute for Ste6 function in yeast by transporting native a-factor pheromone (John Teem, unpublished observations). In order to maximally exploit autocrine yeast strains for the discovery of molecules which enhance mutant CFTR function, an a-factor-like peptide which can serve as a substrate for transport by CFTR will be identified. An a-factor analogue must also bind functionally to the pheromone receptor, Ste3, in order to initiate pheromone signalling. The CFTR transport substrate will be identified by expressing a randomly mutated MFα expression cassette in autocrine yeast deleted for Ste6 expression, but expressing the wild type human CFTR protein.

Expression of Mutant Human CFTR Proteins in Autocrine Yeast.

Transport of an a-factor-like peptide pheromone by CFTR will serve as the basis for the design of screens to be used in the identification of compounds which augment the transport function of CFTR proteins containing cystic fibrosis (CF) mutations. Based on studies done by Teem et al. (1993) using Ste6/CFTR chimeras, mutant CFTR is not expected to efficiently transport an a-factor analogue. Teem et al. (1993) have made chimeric proteins by substituting varying portions of the sequences encoding the first nucleotide binding domain of human CFTR for analogous sequence in yeast STE6. The chimeric proteins will transport native yeast a-factor when expressed in yeast. However, introduction of a CF mutation (ΔF508) reduces the ability of these proteins to transport the yeast pheromone. Teem et al. have also identified revertants in yeast, i.e., proteins containing second site mutations which restore the ability of chimeras bearing the CF mutation to transport a-factor. Introduction of the revertant mutations into defective CFTR protein expressed in mammalian cells decreased in part the processing and channel defects of the ΔF508 protein.

With the identification of an analogue of yeast a-factor that will serve as a substrate for transport by CFTR, mutations can be introduced directly into the human CFTR protein expressed in yeast, eliminating the necessity of creating chimeric proteins containing Ste6 sequence. This will permit the targeting of potential CF therapeutics to the entire human CFTR molecule. Mutations of interest include G551D, N1303K and ΔI507 in addition to ΔF508; these mutations are naturally occurring, give rise to cystic fibrosis in affected individuals, and appear to affect either the transport and processing of CFTR or the regulation of function of that protein (Welsh and Smith 1993). These mutations also rank among the most common alterations of CFTR thus far identified in CF patients.

If a peptide which will serve as a substrate for transport by CFTR cannot be identified, chimeric Ste6/CFTR proteins and unaltered a-factor can be utilized in screens based on autocrine strains of yeast. These strains offer distinct advantages in screening applications: easy adaptability to large-scale automation, simplicity and increased sensitivity when compared to traditional yeast mating cell assays of pheromone signaling, and the potential to employ the instant technology to identify active peptide structures.

Identification of Compounds that Enhance Transport of a-factor-Like Peptide by Mutant CFTR.

Autocrine strains expressing mutant human CFTR protein will be capable of growth on rich media but, due to inadequate transport of and signaling by an a-factor analogue, will not grow efficiently on selective (histidine-deficient) media. Pheromone signaling in these strains initiates expression from a FUS1 promoter sequence controlling transcription of the His3 enzyme; expression of His3 is required for growth on media lacking histidine. These strains will be used to screen compound libraries to identify molecules which reverse the inability of the mutant CFTR to transport a-factor analogue and permit growth of the yeast on histidine-deficient medium. Alternatively, active compounds would be capable of signaling to the a-factor receptor, Ste3, directly, or may interact with the pheromone response pathway elsewhere. Suitable controls would differentiate among these possibilities.

Identification of Random Peptides that Enhance Transport by Mutant CFTR.

Plasmids containing oligonucleotides which encode random peptides will be expressed in autocrine yeast bearing a mutant human CFTR. These peptides, expressed using α-factor-based expression cassettes, will be transported to the extracellular environment via the yeast secretory pathway. Peptides of interest will be identified by virtue of their ability to permit the growth of a mutant CFTR-containing strain on histidine-deficient medium. Active peptides would permit transport of a-factor analogue by the mutant human CFTR. Alternatively, a peptide may interact at other points along the pheromone response pathway. Suitable controls would differentiate between these possible outcomes.

EXAMPLE 8

Prophetic Example of Substitution of Prohormone Convertase PC1 for Yeast KEX2

The mammalian prohormone convertases PC1/PC3 and PC2 are involved in the proteolytic processing of proopiomelanocortin (POMC), with PC1 preferentially releasing adrenocorticotropic hormone (ACTH) and β-lipotropin and PC2 preferentially releasing β-endorphin, N-terminally extended ACTH containing the joining peptide (JP), and either α-melanocyte-stimulating hormone (α-MSH) or des-acetyl α-MSH (Benjannet, S., et al. (1991) Proc. Natl. Acad. Sci. USA 88:3564-3568; Seideh N. G. et al. (1992) FEBS Lett. 310, 235-239). By way of example, a yeast strain is described in which mammalian PC1 processes a chimeric pre-pro-POMC/α-factor peptide, permitting the secretion of mature α-factor and stimulation of the screening strain in an autocrine fashion to histidine prototrophy. Autocrine strains will be constructed in which: 1. yeast KEX2 is disrupted; 2. yeast KEX2 activity is substituted with that of mammalian PC1; 3. a novel MFα construct containing the dibasic cleavage site recognized by PC1 (in place of the KEX2 recognition sequence) will be expressed; 4production of mature α-factor will require PC1 activity; and 5growth of the strain will be stimulated by the production of mature α-factor.

The genotype of the parental strain for this example is MATa bar1::hisG far1-1 fus1-HIS3 ste14::TRP1 ura3 trp1 leu2 his3. Initially, the KEX2 allele of this strain will be disrupted using an integrating plasmid (pkex2Δ) encoding the flanking regions of the KEX2 locus with the entire coding regions from the initiator codon to the terminator codon deleted. Cleavage of pkex2Δ with Bsu36I followed by transfection into the parental strain will result in integration of this plasmid into the KEX2 locus. Transformation can be scored as conversion to uracil prototrophy. Subsequent transfer of URA+ transformants to plates containing 5-fluoroorotic acid results in the growth of colonies with the kex1Δ allele. Integration can be confirmed by Southern blot analysis and by colony PCR using oligonucleotide primers flanking the KEX2 locus. This kex1Δ strain will be able to grow on histidine-deficient media in the presence of exogenenously added α-factor, but will not be able to grow in an autocrine fashion on histidine-deficient media once transfected with Cadus 1219 (URA3 2mu-ori REP3 AmpR f1-ori α-factor) since processing of the pre-pro-POMC/α-factor chimera expressed from Cadus 1219 requires KEX2 activity.

In the screening strain, PC1 activity will substitute for the deleted KEX2 activity in the maturation of α-factor peptide. PC1 cDNA (accession # M69196) obtained from mouse (Korner et al (1991) Proc. Natl. Acad. Sci USA 88:6834-6838) was found to encode a protein of 753 amino acids. Sequences encoding PC1 will be cloned into a high copy replicating plasmid (Cadus 1289). Yeast cells transformed with this plasmid will acquire the ability to grow on leucine-deficient media and will express high levels of PC1 protein due to the presence of the PGK promoter.

A hybrid gene encoding the prepro-region of human POMC (accession # K02406; Takahashi, H., et al (1983) Nucleic Acids Research 11:6847-6858) and the coding region of a single repeat of mature α-factor will be constructed in the following fashion. The prepro-region of human POMC will be amplified with an HindIII site at the 5' end and a BbsI site at the 3' end using VENT polymerase and the following primers: 5' GGG<u>AAGCTT</u> *ATG*CCGAGATCGTGCTGC-CAGCCGC 3' (SEQ ID NO:30) (HindIII site is underlined and initiation codon is italic bold) and antisense 5' GGG GAAGACTTCTGCCCTGCGCCGCTGCTGCC 3' (SEQ ID NO:31) (BbsI recognition is underlined), leaving the amino acid sequence -SSGAGQ-(SEQ ID NO: 119) at the 3' end with a BbsI site leaving an overhang at the -KR- dibasic cleavage sequence. The coding region of α-factor will be amplified from Cadus 1219 with a BbsI site at the 5' end and a BglII site at the 3' end using the primers 5' GGG GAAGACCCGCAGGAGGCAGAAGCTT GGTTGCAG 3' (SEQ ID NO:32) (BbsI site is underlined) and 5' GGG AGATCTTCAGTACATTGGTTGGCC 3' (SEQ ID NO:33) (BglII site is underlined, termination codon is bold) The PCR fragment encoding the pre-pro segment of POMC is restricted with HindIII and BbsI and gel purified, the PCR fragment encoding α-factor is cut with BbsI and BglII and gel purified, and Cadus 1215 is cut with BglII and partially with HindIII and the HindIII-BglII restricted vector containing the pAlter polylinker sequences is gel purified. Three-part ligation of the two PCR products with HindIII and BglII digested Cadus 1215 will yield a hybrid POMC/α-factor gene in which the first 104 amino acids residues are from POMC and the remaining 17 are from α-factor. The structure of this hybrid gene around the PC1 cleavage site is: - - RNSSSSGSSGAGQKREAEAWHWLQLKPGQPMY* (SEQ ID NO:34) where residues donated by POMC are underlined, the dibasic cleavage site is underlined bold, and the sequence of mature α-factor is in italics. The tetrapeptide -EAEA- (SEQ ID NO: 134) juxtaposed between the dibasic cleavage site and the amino-terminal tryptophan of mature α-factor should be removed by the dipeptidyl aminopeptidase activity of ste13p.

Introduction of the PC1-encoding plasmid and the POMC/α-factor plasmid into a kex2α strain with the genotype MATa bar1::hisG far1-1 fus1-HIS3 ste14::TRP1 ura3 trp1 leu2 his3 should result in autocrine growth that is dependent on PC1-mediated cleavage of the dibasic motif at the amino-terminal side of the single copy of α-factor encoded by the POMC/α-factor plasmid. That is, the autocrine behaviour of this strain should be due to expression of PC1. A suitable negative control is provided by expression of mammalian PC2 in place of PC1; the cleavage site of POMC that is inserted upstream of the α-factor gene is not recognized by PC2. Therefore, it should be possible to construct strains specific for PC1- versus PC2-dependent processing by judicious choice of cleavage sites from POMC to append to the 5' end of the α-factor gene. Compounds or random peptides that disrupt the autocrine growth of this strain but which do not have growth inhibitory effects when this strain is grown in histidine-containing media are potential inhibitors of PC1 activity.

EXAMPLE 9

Prophetic Example of Substitution of Human MEK (MAP Kinase Kinase) for Yeast STE7

In order to develop a screen for compounds which act as inhibitors of a mammalian kinase, one could construct a yeast strain that is deficient in STE7 activity, and which contains human MEK in a yeast expression vector. In addition, the strain would be equipped with reporter capacities, as described below.

To disrupt the yeast STE7 gene, the following approach could be taken: pBluescriptKS+, a multicopy E. coli Vector, is engineered to contain STE7 sequences deleted for 5noncoding and promoter sequence and for a sizeable portion of the coding region. The |ste7 sequence is then subcloned into pRS406|ClaI, a Bluescript-based plasmid containing the yeast URA3 gene and the resulting plasmid, pRS406|ClaI|ste7, is used to disrupt the wild type STE7 gene as follows. pRS406|ste7 is digested with ClaI, and used to transform yeast strain CY252 (genotype MATa ste14::TRP1 fus1-HIS3 far1-1 ura3 leu2 trp1 his3 ade2-1 met1) to uracil prototrophy. Subsequent transfer of Ura+ transformants to media containing 5-fluoroorotic acid results in colonies containing the ste7| allele, which is confirmed by Southern analysis and by the inability of the strain to grow in the absence of histidine when stimulated with α pheromone.

To construct a plasmid capable of expressing human MEK in yeast cells, the following oligonucleotides are constructed: 5'-CCGCGTCTCACATGCCCAAGAAGAAGCCG-3' (SEQ ID NO: 35) (forward) and 5'-CCGTCTAGATGCTG-GCAGCGTGGG-3' (SEQ ID NO: 36) (reverse). When used in a polymerase chain reaction (PCR) with human cDNA as template, these primers will direct the amplification of DNA encoding human MEK. To insert the human MEK gene into a yeast expression vector, the PCR product is digested with Esp3I and XbaI (bold sequences above) and ligated to the yeast-E. coli shuttle plasmid Cadus1289, previously digested with NcoI and XbaI. The resulting plasmid will replicate autonomously in yeast cells, confer leucine prototrophy to a yeast leu2 mutant, and direct the expression of MEK from the constitutive PGK1 promoter.

When the above-described PGK1-MEK plasmid is introduced into the CY252-ste7| cells, it should restore their ability to grow in the absence of histidine when incubated with α pheromone, due to the ability of MEK to functionally replace STE7 in the pheromone response pathway and thereby effect the stimulation of the fus1-HIS3 fusion situated in the chromosome. One could then screen for compounds which are able to reverse α pheromone-dependent growth in the absence of histidine, but which have no nonspecific toxic effect in the presence of histidine.

In an autocrine embodiment, the yeast cells made ste7| are of the genotype MATa bar1::hisG far1-1 fus1-HIS3 ste14:: trp1::LYS2 ura3 trp1 leu2 his3 lys2 (CY588trp). The procedure followed is exactly as above for CY252. After construction of CY588trpste7|, the cells created are transformed with the plasmid expressing MEK, as well as with a plasmid capable of expressing secreted α pheromone. This transformed strain (CY588trpste7| [MEK/MFα]) should be able to grow on media lacking histidine and containing high (20 22222222222222 mM) amounts of 3-aminotriazole. The growth of this strain on this media should be strictly dependent on the presence of both plasmids (each necessary, neither sufficient). Compounds that interfere with this growth could be tested as above, with the exception that exogenously added α pheromone is unnecessary.

In addition, CY588trpste7| [MEK/MFα] could be transformed with a plasmid library expressing cytoplasmically targeted random peptides. Those that interfere with the function of MEK would be identified by replica plating to media deficient in histidine (and potentially containing 3-aminotriazole); cells expressing such inhibitory peptides would be His. Such a screen could be streamlined with the addition of reporter constructs with the potential of negative selection, such as fus1-URA3 or fus1-GAL1. In this case inhibitory peptides would confer on the target strain the ability to grow on 5-FOA- (for cells with diminished fus1-URA3) or galactose- (for cells with diminished fus1-GAL1 in a gal10⁻ background) containing media.

Confirmatory tests would include biochemical assay of the activity of MEK (either in vitro or in vivo) in the presence of random peptides or other molecules identified as potential MEK inhibitors.

EXAMPLE 10

Functional Expression of a Mammalian G Protein-Coupled Receptor and Ligand in an Autocrine Yeast Strain In this example we describe a set of experiments that detail the accomplishment of the following: (1) expression of human C5a receptor in yeast; (2) expression of the native ligand of this receptor, human C5a, in yeast; and (3) activation of the endogenous yeast pheromone pathway upon stimulation of the C5a receptor by C5a when both of these molecules are expressed within the same strain of autocrine yeast. Following the experimental data we outline the utility of autocrine strains of yeast that functionally express the human C5a receptor.

Human C5a is a 74 amino acid polypeptide that derives from the fifth component of complement during activation of the complement cascade; it is the most potent of the complement-derived anaphylatoxins. C5a is a powerful activator of neutrophil and macrophage functions including production of cytotoxic superoxide radicals and induction of chemotaxis and adhesiveness. In addition C5a stimulates smooth muscle contraction, induces degranulation of mast cells, induces serotonin release from platelets and increases vascular permeability. The C5a anaphylatoxin can also amplify the inflammatory response by stimulating the production of cytokines. As C5a is a highly potent inflammatory agent, it is a primary target for the development of antagonists to be used for intervention in a variety of inflammatory processes.

The C5a receptor is present on neutrophils, mast cells, macrophages and smooth muscle cells and couples through G proteins to transmit signals initiated through the binding of C5a.

Expression of the C5a Receptor

The plasmid pCDM8-C5aRc, bearing cDNA sequence encoding the human C5a receptor, was obtained from N. Gerard and C. Gerard (Harvard Medical School, Boston, Mass.) (Gerard and Gerard 1991). Sequence encoding C5a was derived from this plasmid by PCR using VENT polymerase (New England Biolabs Inc., Beverly Mass.), and the following primers:

```
#1-
GGTGGGAGGGTGCTCTCTAGAAGGAAGTGTTCA    (SEQ ID NO: 62)
CC

#2-
GCCCAGGAGACCAGACCATGGACTCCTTCAATT    (SEQ ID NO: 63)
ATACCACC.
```

Primer #1 contains a single base-pair mismatch (underlined) to C5a receptor cDNA. It introduces an XbaI site (in bold) 201 bp downstream from the TAG termination codon of the C5a receptor coding sequence. Primer #2 contains two mismatched bases and serves to create an NcoI site (in bold) surrounding the ATG initiator codon (double underlined). The second amino acid is changed from an aspartic acid to an asparagine residue. This is the only change in primary amino acid sequence from the wild type human C5a receptor.

The PCR product was restricted with NcoI and XbaI (sites in bold) and cloned into CADUS 1002 (YEp51Nco), a Gal10 promoter expression vector. The sequence of the entire insert was determined by dideoxy sequencing using multiple primers. The sequence between the NcoI and XbaI sites was found to be identical to the human C5a receptor sequence that was deposited in GenBank (accessions J05327) with the exception of those changes encoded by the PCR primers. The C5a receptor-encoding insert was transferred to CADUS 1289 (pLPXt), a PGK promoter expression vector, using the NcoI and XbaI sites, to generate the C5a receptor yeast expression clone, CADUS 1303.

A version of the C5a receptor which contains a yeast invertase signal sequence and a myc epitope tag at its amino terminus was expressed in Cadus 1270-transferred yeast under control of a GAL10 promoter. Plasmids encoding an untagged version of the C5a receptor and a myc-tagged derivative of FUS1 served as controls. The expression of the tagged receptor in yeast was confirmed by Western blot using the anti-myc monoclonal antibody 9E10. In the lane containing the extract from the Cadus 1270-transformant, the protein that is reactive with the anti-myc monoclonal antibody 9E10 was approximately 40 kD in size, as expected. Note that this receptor construct is not identical to the one used in the autocrine activation experiments. That receptor is not tagged, does not contain a signal sequence and is driven by the PGK promoter.

Expression of the Ligand, C5a

A synthetic construct of the sequence encoding C5a was obtained from C. Gerard (Harvard Medical School, Boston, Mass.) This synthetic gene had been designed as a FLAG-tagged molecule for secretion from E. coli (Gerard and Gerard 1990). The C5a coding region, still containing E. coli codon bias, was amplified using VENT polymerase (New England Biolabs Inc., Beverly Mass.) through 30 cycles using the following primers:

```
C5a5' =
CCCCTTAAGCGTGAGGCAGAAGCTACTCT    (SEQ ID NO: 64)
GCAAAAGAAGATC and

C5a3' =
GAAGATCTTCAGCGGCCGAGTTGCATGTC    (SEQ ID NO: 65)
```

A PCR product of 257 bp was gel isolated, restricted with AflII and BglII, and cloned into CADUS 1215 (an expression vector designed to express peptide sequences in the context of Mfα) to yield CADUS 1297. The regions of homology to the synthetic C5a gene are underlined. The 5' primer also contains pre-pro α-factor sequence. Upon translation and processing of the pre-pro α-factor sequence, authentic human C5a should be secreted by yeast containing CADUS 1297. The insert sequence in CADUS 1297 was sequenced in both orientations by the dideoxy method and found to be identical to that predicted by the PCR primers and the published sequence of the synthetic C5a gene (Franke et al. 1988).

Two sets of experiments, aside from the autocrine activation of yeast detailed below, demonstrated that CADUS 1297 can be used to express C5a in yeast.

1.) C5a was immunologically detected in both culture supernatant and lysed cells using a commercially available enzyme-linked immunosorbent assay (ELISA) (Table 3). This assay indicated the concentration of C5a in the culture supernate to be approximately 50 to 100 nM. In comparison, in data derived from mammalian cells, the binding constant of C5a to its receptor is 1 nM (Boulay et al. 1991).

2.) C5a expressed in yeast was shown to compete for binding with commercially obtained (Amersham Corporation, Arlington Heights, Ill.), radiolabeled C5a on induced HLGO cells.

Activation of the Pheromone Response Pathway in Autocrine Yeast Expressing the Human C5a Receptor and Human C5a Activation of the yeast pheromone response pathway through the interaction of C5a with the C5a receptor was demonstrated using a growth read-out. The strain used for this analysis, CY455 (MATα tbt1-1 ura3 leu2 trp1 his3 fus1-HIS3 can1 ste14::TRP1 ste3*1156), contains the following significant modifications. A pheromone inducible HIS3 gene, fus1-HIS3, is integrated at the FUS1 locus. A hybrid gene containing sequence encoding the first 41 amino acids of GPA1 (the yeast Gα subunit) fused to sequence encoding human Gαi2a (minus codons for the N-terminal 33 amino acids) replaces GPA1 at its normal chromosomal location. The yeast STE14 gene is disrupted to lower the basal level of signaling through the pheromone response pathway. The yeast a-factor receptor gene, STE3, is deleted. The last two modifications are probably not essential, but appear to improve the signal-to-noise ratio.

CY455 (MATα tbt1-1 ura3 leu2 trp1 his3 fus1-HIS3 can1 ste14::TRP1 ste3*1156) was transformed with the following plasmids:

Cadus 1289+Cadus 1215=Receptor$^-$ Ligand$^-$=(R–L–)

Cadus 1303+Cadus 1215=Receptor$^+$ Ligand$^-$=(R+L–)

Cadus 1289+Cadus 1297=Receptor$^-$ Ligand$^+$=(R–L+)

Cadus 1303+Cadus 1297=Receptor$^+$ Ligand$^+$=(R+L+)

Receptor refers to the human C5a receptor.

Ligand refers to human C5a.

Three colonies were picked from each transformation and grown overnight in media lacking leucine and uracil, at pH 6.8 with 25 mM PIPES (LEU$^-$URA$^-$pH6.8 with 25 mM PIPES) This media was made by adding 0.45 ml of sterile 1 M KOH and 2.5 ml of sterile 1 M PIPES pH 6.8 to 100 ml of standard SD LEU$^-$ URA$^-$ media. After overnight growth the pH of this media is usually acidified to approximately pH 5.5. Overnight cultured were washed once with 25 mM PIPES pH 6.8 and resuspended in an equal volume of media lacking leucine, uracil and histidine (LEU$^-$ URA$^-$HIS$^-$ pH6.8 with 25 mM PIPES). The optical density at 600 nm of a 1/20 dilution of these cultures was determined and the cultures were diluted into 25 mM PIPES pH 6.8 to a final OD$_{600}$ of 0.2. A volume (5 μl) of this dilution equivalent to 10,000 cells was spotted on to selective (HIS$^-$ TRP$^-$ pH6.8+1 mM aminotriazole) or non-selective (HIS$^+$ TRP pH6.8) plates. Only those strains expressing both C5a and its receptor (R+L+) show growth on the selective plates which lack histidine,. All test strains are capable of growth on plates containing histidine. The R+L+ strain will grow on plates containing up to 5 mM aminotriazole, the highest concentration tested.

For verification of pheromone pathway activation and quantification of the stimulation, the activity of the fus1 promoter was determined colorimetrically using a fus1-lacZ fusion in a similar set of strains. CY878 (MATα tbt1-1 fus1-HIS3 can1 ste14::trp1::LYS2 ste3*1156 gpa1(41)-Gαi2) was used as the starting strain for these experiments. This strain is a trp1 derivative of CY455. The transformants for this experiment contained CADUS 1584 (pRS424-fus1-lacZ) in addition to the receptor and ligand plasmids. Four strains were grown overnight in SD LEU$^-$ URA$^-$ TRP$^-$ pH6.8 with 50 mM PIPES to an OD$_{600}$ of less than 0.8. Assay of β-galactosidase activity (Guarente 1983) in these strains yields the data shown in FIG. 10.

Projected Uses of the Autocrine C5a Strains:

A primary use of the autocrine C5a strains will be in the discovery of C5a antagonists. Inhibitors of the biological function of C5a would be expected to protect against tissue damage resulting from inflammation in a wide variety of inflammatory disease processes including but not limited to: respiratory distress syndrome (Duchateau et al. 1984; Hammerschmidt et al. 1980), septic lung injury (Olson et al. 1985), arthritis (Banerjee et al. 1989), ischemic and post-ischemic myocardial injury (Weisman 1990; Crawford et al. 1988) and burn injury (Gelfand et al. 1982).

The autocrine C5a system as described can be used to isolate C5a antagonists as follows:

1. High Throughput Screens to Identify Antagonists of C5a.

A straightforward approach involves screening compounds to identify those which inhibit growth of the R+L+ strain described above in selective media but which do not inhibit the growth of the same strain or of a R+L– strain in non-selective media. The counterscreen is necessary to eliminate from consideration those compounds which are generally toxic to yeast. Initial experiments of this type have led to the identification of compounds with potential therapeutic utility.

2. Identification of Antagonists Using Negative Selection.

Replacement of the fus1-HIS3 read-out with one of several negative selection schemes (fus1-URA3/FOA, fus1-GAL1/galactose or deoxygalactose, FAR1 sst2 or other mutations that render yeast supersensitive for growth arrest) would generate a test system in which the presence of an antagonist would result in the growth of the assay strain. Such an approach would be applicable to high-throughput screening of compounds as well as to the selection of antagonists from random peptide libraries expressed in autocrine yeast. Optimization of screens of this type would involve screening the R+L+ strain at a concentration of amino-triazole which ablates growth of the R+L– strain (we are currently using 0.6 to 0.8 mM) and counterscreening the R+L– strain at a concentration of aminotriazole which gives an identical growth rate (we are using 0.14 mM). In addition, the system could employ one of several colorometric, fluorescent or chemiluminescent readouts. Some of the genes which can be fused to the fus1 promoter for these alternate read-outs include lacZ (colorometric and fluorescent substrates), glucuronidase (colorometric and fluorescent substrates), phosphatases (e.g. PHO3, PHO5, alkaline phosphatase; colorometric and chemiuminescent substrates), green protein (endogenous fluorescence), horse radish peroxidase (colorometric), luciferase (chemiluminescence).

The autocrine C5a strains have further utility as follows:

3. In the Identification of Novel C5a Agonists from Random Peptide Libraries Expressed in Autocrine Yeast.

Novel peptide agonists would contribute to structure/function analyses used to guide the rational design of C5a antagonists.

4. In the Identification of Receptor Mutants.

Constitutively active, that is, ligand independent, receptors may be selected from highly mutagenized populations by growth on selective media. These constitutively active receptors may have utility in permitting the mapping of the sites of interaction between the receptor and the G-protein. Identification of those sites may be important to the rational design of drugs to block that interaction. In addition, receptors could be selected for an ability to be stimulated by some agonists but not others or to be resistant to antagonist. These variant receptors would aid in mapping sites of interaction between receptor and agonist or antagonist and would therefore contribute to rational drug design efforts.

5. In the Identification of Molecules that Interact with Gαi2.

Compounds or peptides which directly inhibit GDP exchange from Gαi2 would have the same effect as C5a antagonists in these assays. Additional information would distinguish inhibitors of GDP exchange from C5a antagonists. This information could be obtained through assays that determine the following:
1. inhibition by test compounds of Gαi2 activation from other receptors,
2. failure of test compounds to compete with radiolabeled C5a for binding to the C5a receptor,
3. failure of test compounds to inhibit the activation of other Gα subunits by C5a, and
4. inhibition by test compounds of signalling from constitutively active versions of C5a, or other, receptors.

EXAMPLE 11

Construction of Hybrid Gα Genes

Construction of Two Sets of Chimeric Yeast/Mammalian Gα Genes, GPA$_{41}$-Gα and GPA1$_{Bam}$-Gα.

The Gα subunit of heterotrimeric G proteins must interact with both the βγ complex and the receptor. Since the domains of Gα required for each of these interactions have not been completely defined and since our final goal requires Gα proteins that communicate with a mammalian receptor on one hand and the yeast βγ subunits on the other, we desired to derive human-yeast chimeric Gα proteins with an optimized ability to perform both functions. From the studies reported here we determined that inclusion of only a small portion of the amino terminus of yeast Gα is required to couple a mammalian Gα protein to the yeast βγ subunits. It was anticipated that a further benefit to using these limited chimeras was the preservation of the entire mammalian domain of the Gα protein believed to be involved in receptor contact and interaction. Thus the likelihood that these chimeras would retain their ability to interact functionally with a mammalian receptor expressed in the same yeast cell was expected to be quite high.

Plasmid Constructions.

pRS416-GPA1 (Cadus 1069).

An XbaI-SacI fragment encoding the entire GPA1 promoter region, coding region and approximately 250 nucleotides of 3' untranslated region was excised from YCplac111-GPA1 (from S. Reed, Scripps Institute) and cloned into YEp vector pRS416 (Sikorski and Hieter, Genetics 122: 19 (1989)) cut with XbaI and SacI.

Site-Directed Mutagenesis of GPA1 (Cadus 1075, 1121 and 1122). A 1.9 kb EcoRI fragment containing the entire GPA1 coding region and 200 nucleotides from the 5' untranslated region was cloned into EcoRI cut, phosphatase-treated pALTER-1 (Promega) and transformed by electroporation (Biorad Gene Pulser) into DH5αF' bacteria to yield Cadus 1075. Recombinant phagemids were rescued with M13KO7 helper phage and single stranded recombinant DNA was extracted and purified according to the manufacturer's specifications. A new NcoI site was introduced at the initiator methionine of GPA1 by oligonucleotide directed mutagenesis using the synthetic oligonucleotide:

5' GATATATTAAGGTAGGAAA<u>CCATGG</u>GGTGTACA GTGAG 3' (SEQ ID NO: 66).

Positive clones were selected in ampicillin and several independent clones were sequenced in both directions across the new NcoI site at +1. Two clones containing the correct sequences were retained as Cadus 1121 and 1122.

Construction of a GPA1-based Expression Vector (Cadus 1127).

The vector used for expression of full length and hybrid mammalian Gα proteins in yeast, Cadus 1127, was constructed in the following manner. A 350 nucleotide fragment spanning the 3' untranslated region of GPA1 was amplified with Taq polymerase (AmpliTaq; Perkin Elmer) using the oligonucleotide primers A (5' CGAGC-GCTCGAGG-GAACGTATAATTAAAGTAGTG 3' (SEQ ID NO: 67)) and B (5' GCGCGGTACCAAGCTTC-AATTC-GAGATAATACCC 3' (SEQ ID NO: 68). The 350 nucleotide product was purified-by gel electrophoresis using GeneClean II (Bio101) and was cloned directly into the pCRII vector by single nucleotide overlap TA cloning (InVitrogen). Recombinant clones were characterized by restriction enzyme mapping and by dideoxynucleotide sequencing. Recombinant clones contained a novel XhoI site 5' to the authentic GPA1 sequence and a novel KpnI site 3' to the authentic GPA1 sequence donated respectively by primer A and primer B.

The NotI and SacI sites in the polylinker of Cadus 1013 (pRS414) were removed by restriction with these enzymes followed by filling in with the Klenow fragment of DNA polymerase I and blunt end ligation to yield Cadus 1092. The 1.4 kb PstI-EcoRI 5' fragment of GPA1 from YCplac111-GPA1 containing the GPA1 promoter and 5' untranslated region of GPA1 was purified by gel electrophoresis using GeneClean (Bio101) and cloned into PstI-EcoRI restricted Cadus 1013 to yield Cadus 1087. The PCR amplified XhoI-KpnI fragment encoding the 3' untranslated region of GPA1 was excised from Cadus 1089 and cloned into XhoI-KpnI restricted Cadus 1087 to yield Cadus 1092. The Not1 and Sac1 sites in the polylinker of Cadus 1092 were removed by restriction with these enzymes, filling in with the Klenow fragment of DNA polymerase I, and blunt end ligation to yield Cadus 1110. The region of Cadus 1122 encoding the region of GPA1 from the EcoRI site at −200 to +120 was amplified with Vent DNA polymerase (New England Biolabs, Beverly, Mass.) with the primers (SEQ ID NO: 69)
5' CCCGAATCCACCAATTTCTTTACG 3' and (SEQ ID NO: 70)
5' GCGGCGTCGACGCGGCCGCGTAACAGT 3'.

The amplified product, bearing an EcoRI site at its 5' end and novel SacI, NotI and SalI sites at its 3' end was restricted with EcoRI and SalI, gel purified using GeneClean II (Bio101), and cloned into EcoRI and SalI restricted Cadus 1110 to yield Cadus 1127. The DNA sequence of the vector between the EcoRI site at −200 and the KpnI site at the 3' end of the 3' untranslated region was verified by restriction enzyme mapping and dideoxynucleotide DNA sequence analysis.

PCR Amplification of GPA$_{41}$-Gα Proteins and Cloning into Cadus 1127.

cDNA clones encoding the human G alpha subunits Gαs, Gαi2, Gαi3, and S. cerevisiae GPA1 were amplified with Vent thermostable polymerase (New England Bioloabs, Beverly, Mass.). The primer pairs used in the amplification are as follows:

```
Gαs   Primer 1:                         (SEQ ID NO: 71)
      5'CTGCTGGAGCTCCGCCTGCTGCTGCTGGGTGCTG (SacI 5')
      GAG3'

Primer 2:                         (SEQ ID NO: 72)
      5'CTGCTGGTCGACGCGGCCGCGGGGGTTCCTTCTT (SalI 3')
      AGAAGCAGC3'

Primer 3:                         (SEQ ID NO: 73)
      5'GGGCTCGAGCCTTCTTAGAGCAGCTCGTAC3'   (XhoI 3')

Gαi2  Primer 1:                         (SEQ ID NO: 74)
      5'CTGCTGGAGCTCAAGTTGCTGCTGTTGGGTGCTG (SacI 5')
      GGG3'

Primer 2:                         (SEQ ID NO: 75)
      5'CTGCTGGTCGACGCGGCCGCGCCCCTCAGAAGAG (SalI 3')
      GCCGCGGTCC3'

Primer 3:                         (SEQ ID NO: 76)
      5'GGGCTCGAGCCTCAGAAGAGGCCGCAGTC3'    (XhoI 3')

Gαi3  Primer 1:                         (SEQ ID NO: 77)
      5'CTGCTGGAGCTCAAGCTGCTGCTACTCGGTGCTG (SacI 5')
      GAG3'

Primer 2:                         (SEQ ID NO: 78)
      5'CTGCTGGTCGACGCGGCCGCCACTAACATCCATG (SalI 3')
      CTTCTCAATAAAGTC3'

Primer 3:                         (SEQ ID NO: 79)
      5'GGGCTCGAGCATGCTTCTCAATAAAGTCCAC3'  (XhoI 3')
```

After amplification, products were purified by gel electrophoresis using GeneClean II (Bio101) and were cleaved with the appropriate restriction enzymes for cloning into Cadus 1127.

The hybrid $GPA_{41}$-$G_\alpha$ subunits were cloned via a SacI site introduced at the desired position near the 5' end of the amplified genes and a SalI or XhoI site introduced in the 3' untranslated region. Ligation mixtures were electroporated into competent bacteria and plasmid DNA was prepared from 50 cultures of ampicillin resistant bacteria.

Construction of Integrating Vectors Encoding $GPA_{41}$-$G_\alpha$ Subunits.

The coding region of each GPA41-Gα hybrid was cloned into an integrating vector (pRS406=URA3 AmpR) using the BssHII sites flanking the polylinker cloning sites in this plasmid. Cadus 1011 (PRS406) was restricted with BssHII, treated with shrimp alkaline phosphatase as per the manufacturer's specifications, and the linearized vector was purified by gel electrophoresis. Inserts from each of the $GPA_{41}$-$G\alpha$ hybrids were excised with BssHII from the parental plasmid, and subcloned into gel purified Cadus 1011.

Construction of $GPA_{Bam}$-$G\alpha$ Constructs. A novel BamHI site was introduced in frame into the GPA1 coding region by PCR amplification using Cadus 1179 (encoding a wildtype GPA1 allele with a novel NcoI site at the initiator methionine) as the template, VENT polymerase, and the following primers: Primer A=5' GCATCCATCAATAATCCAG 3' (SEQ ID NO: 80) and Primer B=5' GAAACAATGGATCCACTTCTTAC 3' (SEQ ID NO: 81). The 1.1 kb PCR product was gel purified with GeneClean II (Bio101), restricted with NcoI and BamHI and cloned into NcoI-BamHI cut and phosphatased Cadus 1122 to yield Cadus 1605. The sequence of Cadus 1605 was verified by restriction analysis and dideoxy-sequencing of double-stranded templates. Recombinant $GPA_{Bam}$-$G\alpha$_hybrids of Gαs, Gαi2, and Gα16 were generated. Construction of Cadus 1855 encoding recombinant $GPA_{Bam}$-$G\alpha$_16 serves as a master example: construction of the other hybrids followed an analogous cloning strategy. The parental plasmid Cadus 1617, encoding native Gα16, was restricted with NcoI and BamHI, treated with shrimp alkaline phosphatase as per the manufacturer's specifications and the linearized vector was purified by gel electrophoresis. Cadus 1605 was restricted with NcoI and BamHI and the 1.1 kb fragment encoding the amino terminal 60% of GPA1 with a novel BamHI site at the 3' end was cloned into the NcoI- and BamHI-restricted Cadus 1617. The resulting plasmid encoding the $GPA_{Bam}$-$G\alpha$_16 hybrid was verified by restriction analysis and assayed in tester strains for an ability to couple to yeast Gβγ and thereby suppress the gpa1 null phenotype. Two additional $GPA_{Bam}$-$G\alpha$_hybrids, $GPA_{Bam}$-$G\alpha$s_and $GPA_{Bam}$-$G\alpha$i2, described in this application were prepared in an analogous manner using Cadus1606 as the parental plasmid for the construction of the $GPA_{Bam}$-$G\alpha$i2 hybrid and Cadus 1181 as the parental plasmid for the construction of the $GPA_{Bam}$-$G\alpha$_s hybrid.

Coupling by Chimeric $G\alpha$_Proteins. The Gα chimeras described above were tested for the ability to couple a mammalian G protein-coupled receptor to the pheromone response pathway in yeast. The results of these experiments are outlined in Table 5. Results obtained using $GPAl_{41}$-$G\alpha$i2 to couple the human C5a receptor to the pheromone response pathway in autocrine strains of yeast are disclosed in Example 10 above.

EXAMPLE 12

Screening for Modulators of G-Alpha Activity

Screens for modulators of Gα activity may also be performed as shown in the following examples for illustration purposes, which are intended to be non-limiting.

The strains used in this experiment are characterized in Table 9. Strains CY4874 and CY4877 are isogenic but for the presence of Q205L mutation in the cloned $G\alpha_{i2}$ gene cloned into plasmid 1. Strains CY4901 and CY4904 each have a chromosomally integrated chimeric Gα fusion comprising 41 amino acids of gpa1 at the N terminus of the human $G\alpha_{i2}$ gene and are isogenic but for the presence of a constitutively activating mutation in the C5a receptor gene of CY4901. Strain CY5058 is a gpa1 mutant which carries only the yeast Gβγ subunits and no Gα subunit. This strain is a control strain to demonstrate specificity of action on the Gα subunit.

I. Suppression of Activation by Mutation of Gα

The Q205L mutation is a constitutively activated GTPase deficient mutant of the human $G\alpha_{i2}$ gene. Antagonist compounds, chemicals or other substances which act on $G\alpha_{i2}$ can be recognized by their action to reduce the level of activation and thus reduce the signal from the fus1-lacZ reporter gene on the second plasmid (Plasmid 2).

A. GTPase⁻ $G\alpha_{i2}$ Mutants
   test component=gpa$_{41}$-$G\alpha_{i2}$ ($Q_{205}L$)
   control component=gpa$_{41}$-$G\alpha_{i2}$ As well as the CY4874 and CY4877 constructs detailed above, similar strains with fus1-His3 or fus2-CAN1 growth readouts may also be used. The fus1-His3 strains are preferred for screening for agonists and the fus2-CAN1 strains are preferred for antagonist screens.

| Readout | test strain | effect of Gα$_{i2}$ antagonist | control strain |
|---|---|---|---|
| fus1-HIS3 | CY4868 | inhibit growth on −HIS +AT(Aminotriazole) | CY4871 |
| fus1-lacZ | CY4874 | reduce β-gal activity | CY4877 |
| fus2-CAN1 | CY4892 | induce growth on canavanine | CY4386 |

In each case an antagonist should cause the test strain to behave more like the control strain.

B. GTPase⁻ Gα$_S$ Mutants (Gα Specificity)

test component=Gα$_S$(Q$_{227}$L)
  control component=Gα$_S$

| Readout | test strain | effect of Gα$_{i2}$ antagonist | control strain |
|---|---|---|---|
| fus1-HIS3 | CY4880 | none | CY4883 |
| fus1-lacZ | CY4886 | none | CY4889 |
| fus2-CAN1 | CY4895 | none | CY4898 |

In each case a non-specific antagonist would cause the test strain to behave more like the control strain.

Additional media requirements: -TRP for Gα plasmid maintenance in fus1-HIS3 and fus2-CAN1 screens and -TRP -URA for Gα and fus1-lacZ plasmid maintenance in fus1-lacZ screen.

II. Suppression of Activation by Receptors

Constitutively Activated C5a Receptors test component=C5aR* (P$_{184}$L, activated C5a Receptor)
  control component=C5aR The C5aR* mutation has a Leucine residue in place of the Proline residue of the wild-type at position 184 of the amino acid sequence.

| Readout | test strain | effect of Gα$_{i2}$ antagonist | control strain |
|---|---|---|---|
| fus1-HIS3 | CY4029 | inhibit growth on −HIS +AT(Aminotriazole) | CY2246 |
| fus1-lacZ | CY4901 | reduce β-gal activity | CY4904 |
| fus2-CAN1 | CY4365 | induce growth on canavanine | CY4362 |

In each case an antagonist should cause the test strain to behave more like the control strain.

Additional media requirements: -LEU for receptor plasmid maintenance in fus1-HIS3 and fus2-CAN1 screens and -LEU-URA for receptor and fus1-lacZ plasmid maintenance in fus1-lacZ screen, non-buffered yeast media (pH 5.5).

TABLE 1

| ABC TRANSPORTERS* | | |
|---|---|---|
| Species | System | Substrate |
| Bacteria | | |
| Salmonella typhimurium | OppABCDF | Oligopeptides |
| Streptococcus pneumoniae | AmiABCDEF | Oligopeptides |
| Bacillus subtilis | Opp (SpoOK) | Oligopeptides |
| E. coli | Dpp | Dipeptides |
| Bacilus subtilis | DciA | Dipeptides |
| S. typhimurium | HisJQMP | Histidine |
| E. coli | HisJQMP | Histidine |
| E. coli | MalEFGK | Maltose |
| S. typhimurium | MalEFGK | Maltose |
| Enterobacter aerogenes | MalEFGK | Maltose |
| E. coli | UgpABCE | sn-Glycerol-3-phosphate |
| E. coli | AraFGH | Arabinose |
| E. coli | RbsACD | Ribose |
| E. coli | GlnHPQ | Glutamine |
| S. typhimurium | ProU (VWX) | Glycine-betaine |
| E. coli | ProU (VWX) | Glycine-betaine |
| E. coli | LivHMGF (JK) | Leucine-isoleucine-valine |
| E. coli | PstABC | Phosphate |
| Pseudomonas stutzeri | NosDYF | Copper |
| E. coli | ChlJD | Molybdenum |
| E. coli | CysPTWAM | Sulphate-Thiosulfate |
| E. coli | BtuCDE | Vitamin B12 |
| E. coli | FhuBCD | Fe$^{3+}$-ferrichrome |
| E. coli | FecBCDE | Fe$^{3+}$-dicitrate |
| S. marcescens | SfuABC | Fe$^{3+}$ |
| Mycoplasma | p37, 29, 69 | ? |
| E. coli | Phn/Psi | Alkyl-phosphonates (?) |
| Streptomyces peucetius | DrrAB | Daunomycin/Doxorubicin |
| Streptomyces fradiae | TlrC | Tylosin |
| Staphylococcus | MsrA | Erythromycin resistance |
| Agrobacterium tumefaciens | OccJQMP | Octopine |
| E. coli | HlyB | Haemolysin |
| Pasturella | LtkB | leukotoxin |
| E. coli | CvaB | Colicin V |
| Erwinia chrysanthemi | PrtD | Proteases |
| Bordetella pertussis | CyaB | Cyclolysin |
| Streptococcus pneumoniae | ComA | Competence factor |
| Rhizobium meliloti | NdvA | β-1,2-glucan |
| Agrobacterium tumefaciens | ChvA | β-1,2-glucan |
| Haemophilus influenzae | BexAB | Capsule polysaccharide |
| E. coli | KpsMT | Capsule polysaccharide |
| Niesseria | CrtCD | Capsule polysaccharide |
| E. coli | FtsE | Cell division |
| E. coli | UvrA | DNA repair |
| Rhizobium leguminosarum | NodI | Nodulation |
| Rhizobium meliloti | OFR1 | ? |
| Cyanobacteria | | |
| Anabaena | HetA | Differentiation |
| Synchococcus | CysA | Sulphate |

TABLE 1-continued

ABC TRANSPORTERS*

| Species | System | Substrate |
|---|---|---|
| Yeast | | |
| S. cerevisiae | STE6 | a-mating peptide |
| S. cerevisiae | ADP1 | ? |
| S. cerevisiae | EF-3 | Translation |
| Protozoa | | |
| Plasmodium | pfMDR | Chloroquine |
| Lieshmania | ltpgpA | Methotrexate/heavy metals |
| Insect | | |
| Drosophila | white-brown | Eye pigments |
| Drosophila | Mdr49 | Hydrophobic drugs? |
|  | Mdr65 | ? |
| Plants | | |
| Liverwort chloroplast | MbpX | ? |
| Animals | | |
| Man | CFTR | Chloride |
| Mouse | CFTR | Chloride |
| Xenopus | CFTR | Chloride |
| Cow | CFTR | Chloride |
| Dogfish | CFTR | Chloride |
| Man | MDR1 | Hydrophobic drugs |
|  | MDR3 | ? |
| Mouse | MDR1 | Hydrophobic drugs |
|  | MDR2 | ? |
|  | MDR3 | Hydrophobic drugs |
|  | MDR3 | Hydrophobic drugs |
| Hamster | Pgp1 | Hydrophobic drugs |
|  | Pgp2 | Hydrophobic drugs |
|  | Pgp3 | ? |
| Man | PMP70 | Polypeptides? |
| Man | RING4-11 | Peptides |
|  | PSF1-PSF2 | Peptides |
| Mouse | HAM1-HAM2 | Peptides |
| Rat | Mtp1 | Peptides |

*Adapted from Higgins, C.F. 1992. ABC Transporters: From Microorganizmz to Man. Annu. Rev. Cell Biol. 8, 67-113.

TABLE 2

HUMAN G PROTEIN-COUPLED SEVEN TRANSMEMBRANE RECEPTORS: REFERENCES FOR CLONING

| Receptor | Reference |
|---|---|
| $\alpha_{1A}$-adrenergic receptor | Bruno et al. (1991) |
| $\alpha_{1B}$-adrenergic receptor | Ramarao et al. (1992) |
| $\alpha_2$-adrenergic receptor | Lomasney et al. (1990) |
| $\alpha_{2B}$-adrenergic receptor | Weinshank et al. (1990) |
| $\beta_1$-adrenergic receptor | Frielle et al. (1987) |
| $\beta_2$-adrenergic receptor | Kobilka et al. (1987) |
| $\beta_3$-adrenergic receptor | Regan et al. (1988) |
| $m_1$ AChR, m2 AChR, $m_3$ AChR, $m_4$ AChR | Bonner et al. (1987) Peralta et al. (1987) |
| m5 AChR | Bonner et al. (1988) |
| $D_1$ dopamine | Dearry et al. (1990) |
|  | Zhou et al. (1990) |
|  | Sunahara et al. (1990) |
|  | Weinshank et al. (1991) |
| $D_2$ dopamine | Grandy et al. (1989) |
| $D_3$ dopamine | Sokoloff et al. (1990) |
| $D_4$ dopamine | Van Tol et al. (1991) |
| $D_5$ dopamine | M. Caron (unpub.) |
|  | Weinshank et al. (1991) |
| A1 adenosine | Libert et al. (1992) |
| adenosine A2b | Pierce et al. (1992) |
| 5-HT1a | Kobilka et al. (1987) |
|  | Fargin et al. (1988) |
| 5-HT1b | Hamblin et al. (1992) |
|  | Mochizuki et al. (1992) |
| 5HT1-like | Levy et al. (1992a) |
| 5-HT1d | Levy et al. (1992b) |
| 5HT1d-like | Hamblin and Metcalf (1991) |
| 5HT1d beta | Demchyshyn et al. (1992) |
| substance K (neurokinin A) | Gerard et al. (1990) |
| substance P (NK1) | Gerard, et al. (1991); |
|  | Takeda et al. (1991) |
| f-Met-Leu-Phe | Boulay et al. (1990) |
|  | Murphy & McDermott (1991) |
|  | DeNardin et al. (1992) |
| angiotensin II type 1 | Furuta et al. (1992) |
| mas proto-oncogene | Young et al. (1986) |
| endothelin ETA | Hayzer et al. (1992) |
|  | Hosoda et al. (1991) |
| endothelin ETB | Nakamuta et al. (1991) |
|  | Ogawa et al. (1991) |
| thrombin | Vu et al. (1991) |
| growth hormone-releasing hormone (GHRH) | Mayo (1992) |
| vasoactive intestinal peptide (VIP) | Sreedharan et al. (1991) |
| oxytocin | Kimura et al., (1992) |
| somatostatin SSTR1 and SSTR2 | Yamada et al. (1992a) |
| SSTR3 | Yamada et al. (1992b) |
| cannabinoid | Gerard et al. (1991) |
| follicle stimulating hormone (FSH) | Minegish et al. (1991) |
| LH/CG | Minegish et al. (1990) |
| thyroid stimulating hormone (TSH) | Nagayama et al. (1989) |
|  | Libert et al. (1989) |
|  | Misrahi et al. (1990) |
| thromboxane A2 | Hirata et al. (1991) |
| platelet-activating factor (PAF) | Kunz et al. (1992) |
| C5a anaphylatoxin | Boulay et al. (1991) |
|  | Gerard and Gerard (1991) |
| Interleukin 8 (IL-8) IL-8RA | Holmes et al. (1991) |
| IL-8RB | Murphy and Tiffany (1991) |
| Delta Opioid | Evans et al. (1992) |
| Kappa Opioid | Xie et al. (1992) |
| mip-1/RANTES | Neote et al. (1993) |
|  | Murphy et al., in press |
| Rhodopsin | Nathans and Hogness (1984) |
| Red opsin, Green opsin, Blue opsin | Nathans, et al. (1986) |
| metabotropic glutamate mGluR1-6 | Tanabe et al. (1992) |
| histamine H2 | Gantz et al. (1991) |
| ATP | Julius, David (unpub.) |
| neuropeptide Y | Herzog et al. (1992) |
|  | Larhammar et al. (1992) |
| amyloid protein precursor | Kang et al. (1987) |
|  | Mita, et al. (1988) |
|  | Lemaire et al. (1989) |
| insulin-like growth factor II | Kiess et al. (1988) |
| bradykinin | Hess et al. (1992) |
| gonadotropin-releasing hormone | Chi et al. (1993) |
| cholecystokinin | Pisegna et al. (1992) |
| melanocyte stimulating hormone receptor | Chhajlane et al. (1992) Mountjoy et al. (1992) |
| antidiuretic hormone receptor | Birnbaumer et al. (1992) |
| glucagon receptor | Sprecher et al. (1993) |
| adrenocorticotropic hormone II | Mountjoy et al. (1992) |

References to Table 2

Bonner, T. I., Buckley, N. J., Young, A. C., and Brann, M. R. (1987). Identification of a family of muscarinic acetylcholine receptor genes. Science 237, 527-532.

Bonner, T. I., Young, A. C., Brann, M. R., and Buckley, N. J. (1988). Cloning and expression of the human and rat m5 muscarinic acetylcholine receptor genes. Neuron 1, 403-410.

Boulay, F., Mery, L., Tardif, M., Brouchon, L., and Vignais, P. (1991) Expression cloning of a receptor for C5a anaphylatoxin on differentiated HL-60 cells. Biochemistry 30, 2993-2999.

Boulay, F., Tardif, M., Brouchon, L., Vignais, P. (1990) The human N-formylpeptide receptor. Characterization of two cDNA isolates and evidence for a new subfamily of G protein-coupled receptors. Biochemistry 29, 11123-11133.

Bruno, J. F., Whittaker, J., Song, J. F., Berelowitz, M. (1991.) Molecular cloning and sequencing of a cDNA encoding a human 1A adrenergic receptor. Biochem. Biophys. Res. Commun. 179, 1485-1490.

De-Nardin-E. Radel-S-J. Lewis-N. Genco-R-J. Hammarskjold-M. (1992) Identification of a gene encoding for the human formyl peptide receptor. Biochem-Int. 26, 381-387.

Dearry, A., Gingrich, J. A., Falardeau, P., Fremeau, R. T., Bates. M. D., Caron, M. G. (1990) Molecular cloning and expression of the gene for a human $D_1$ dopamine receptor. Nature 347, 72-76.

Demchyshyn-L. Sunahara-R-K. Miller-K. Teitler-M. Hoffman-B-J. Kennedy-J-L. Seeman-P. Van-Tol-H-H. Niznik-H-B. A human serotonin 1D receptor variant (5HT1D beta) encoded by an intronless gene on chromosome 6. (1992) Proc-Natl-Acad-Sci-U-S-A. 89, 5522-5526.

Evans, C. J., Keith, D. E. Jr., Morrison, H., Magendzo, K., and Edwards, R. H. (1992) Cloning of a delta opioid receptor by functional expression. Science 258, 1952-1955.

Fargin, A., Raymond, J. R., Lohse, M. J., Kobilka, B. K., Caron, M. G., and Lefkowitz, R. J. (1988). The genomic clone G-21 which resembles a β-adrenergic receptor sequence encodes the $5-HT_{1a}$ receptor. Nature 335, 358-360.

Frielle, T., Collins, S., Daniel, K. W., Caron, M. G., Lefkowitz, R. J., and Kobilka, B. K. (1987) Cloning of the cDNA for the human 1-adrenergic receptor. Proc. Natl. Acad. Sci. U.S.A. 84, 7920-7924.

Furuta-H. Guo-D-F. Inagami-T. (1992) Molecular cloning and sequencing of the gene encoding human angiotensin II type 1 receptor. Biochem-Biophys-Res-Commun. 183, 8-13.

Gantz, I., Munzert, G., Tashiro, T., Schaffer, M., Wang, L., DelValle, J., Yamada, T. (1991b) Molecular cloning of the human histamine H2 receptor. Biochem. Biophys. Res. Commun. 178, 1386-1392.

Gerard, N. P., Eddy, R. L. Jr., Shows, T. B., and Gerard, C. (1990) The human neurokinin A (Substance K) receptor. Molecular cloning of the gene, chromosomal localization, and isolation of cDNA from tracheal and gastric tissues. J. Biol. Chem. 265, 20455-20462.

Gerard, N. P. and Gerard, C. (1991) The chemotactic receptor for C5a anaphylatoxin. Nature 349, 614-617.

Gerard, N. P., Garraway, L. A., Eddy, R. L. Jr., Shows, T. B., Iijima H., Paquet, J.-L. and Gerard, C. (1990) Human substance P receptor (NK-1): Organization of the gene, chromosome localization, functional expression of cDNA clones. Biochem. 30, 10640-10646.

Gerard, C. M., Mollereau, C., Vassart, G., and Parmentier, M. (1991) Molecular cloning of a human cannabinoid receptor which is also expressed in testis. Biochem. J. 279, 129-134.

Grandy, D. K., Marchionni, M. A., Makam, H., Stofko, R. E., Alfanzo, M., Frothingham, L., Fischer, J. B., Burke-Howie, K. J., Bunzow, J. R., Server, A. C. and Civelli, O. (1989) Cloning of the cDNA and gene for a human $D_2$ dopamine receptor. Proc. Natl. Acad. Sci. U.S.A. 86, 9762-9766.

Hamblin, M. W., and Metcalf, M. A. (1991) Primary structure and functional characterization of a human 5-HT1D-type serotonin receptor. Mol. Pharmacol. 40, 143-148.

Hamblin-M-W. Metcalf-M-A. McGuffin-R-W. Karpells-S. (1992) Molecular cloning and functional characterization of a human 5-HT1B serotonin receptor: a homologue of the rat 5-HT1B receptor with 5-HT1D-like pharmacological specificity. Biochem-Biophys-Res-Commun. 184, 752-759.

Hayzer-D-J. Rose-P-M. Lynch-J-S. Webb-M-L. Kienzle-B-K. Liu-E-C. Bogosian-E-A. Brinson-E. Runge-M-S. (1992) Cloning and expression of a human endothelin receptor: subtype A. Am-J-Med-Sci. Oct. 304, 231-238.

Herzog, H., Hort, Y. J., Ball, H. J., Hayes, G., Shine, J., and Selbie, L. A. (1992) Cloned human neuropeptide Y receptor couples to two different second messenger systems. Proc. Natl. Acad. Sci. U.S.A. 89, 5794-5798.

Hirata, M., Hayashi, Y., Ushikubi, F., Yokota, Y., Kageyama, R., Nakanishi, S and Narumiya, S. (1991) Cloning and expression of cDNA for a human thromboxane $A_2$ receptor. Nature 349, 617-620.

Holmes, W. E., Lee, J., Kuang, W.-J., Rice, G. C., and Wood, W. I. (1991) Structure and functional expression of a human interleukin-8 receptor. Science 253, 1278-1280

Hosoda-K. Nakao-K. Hiroshi-Arai. Suga-S. Ogawa-Y. Mukoyama-M. Shirakami-G. Saito-Y. Nakanishi-S. Imura-H. (1991) Cloning and expression of human endothelin-1 receptor cDNA. FEBS-Lett. 287, 23-26.

Kang, J. Lemaire, H.-G., Unterbeck, A., Salbaum, J. M., Masters, C. L., Grzeschik, K.-H., Multhaaup, G., Beyreuther, K., Müller-Hill, B. (1987) The precursor of Alzheimer's disease amyloid protein resembles a cell-surface receptor. Nature 325, 733-736.

Kiess, W., Blickenstaff, G. D., Sklar, M. M., Thomas, C. L., Nissley, S. P. and Sahagian G. G. (1988) Biochemical evidence that the type II insulin-like growth factor receptor is identical to the cation-independent mannose 6-phosphate receptor. J. Biol. Chem. 263, 9339-9344.

Kimura, T., Tanizawa, O., Mori, K., Brownstein, M. J., and Okayama, H. (1992) Structure and expression of a human oxytocin receptor. Nature 356, 526-529.

Kobilka, B. K., Dixon, R. A. F., Frielle, T., Dohlman, H. G., Bolanowski, M. A., Sigal, I. S., Yang-Feng, T. L., Francke, U., Caron, M. G., and Lefkowitz, R. J. (1987) cDNA for the human $β_2$-adrenergic receptor: A protein with multiple membrane spanning domains and a chromosomal location shared with the PDGF receptor gene. Proc. Natl. Acad. Sci. U.S.A. 84, 46-50.

Kobilka, B. K., Frielle, T., Collins, S., Yang-Feng, T., Kobilka, T. S., Francke, U., Lefkowitz, R. J. and Caron, M. G. (1987). An intronless gene encoding a potential member of the family of receptors coupled to guanine nucleotide regulatory proteins. Nature 329, 75-79

Kunz, D., Gerard, N. P., and Gerard, C. (1992) The human leukocyte platelet-activating factor receptor. cDNA cloning, cell surface expression and construction of a novel epitope-bearing analog. J. Biol. Chem. 267, 9101-9106.

Larhammar, D., Blomqvist, A. G., Yee, F., Jazin, E., Yoo, H., Wahlested, C. (1992) Cloning and functional characterization of a human neuropeptide Y/peptide YY receptor of the Y1 type. J. Biol. Chem. 267, 10935-10938.

Lemaire, H. G., Salbaum, J. M., Multhauo, Kang, J., Bayney, R. M., Unterbeck, A., Beyreuther, K., Müller-Hill, B.

(1989) The PreA4$_{695}$ precursor protein of Alzheimer's disease A4 amyloid is encoded by 16 exons. Nuc. Acids. Res. 17, 517-522.

Levy, F. O., Gudermann, T., -Perez-Reyes, E., Birnbaumer, M., Kaumann, A. J., and Birnbaumer, L. (1992b) Molecular cloning of a human serotonin receptor (S12) with a pharmacological profile resembling that of the 5-HT1d subtype. J. Biol. Chem. 267, 7553-7562.

Levy, F. O., Gudermann, T., Birnbaumer, M., Kaumann, A. J., and Birnbaumer, L. (1992a) Molecular cloning of a human gene (S31) encoding a novel serotonin receptor mediating inhibition of adenylyl cyclase. FEBS. Lett., 296, 201-206.

Libert, F., Lefort, A., Gerard, C., Parmentier, M., Perret, J., Ludgate, M., Dumont, J., Vassart, G. (1989) Cloning, sequence and expression of the human thyrotropin (TSH) receptor: Evidence for the binding of autoantibodies. Biochem. Biophys. Res. Commun. 165, 150-155.

Libert, F., Van Sande, J., Lefort, A., Czernilofsky, A., Dumont, J. E., Vassart, G., Ensinger, H. A., and Mendla, K. D. (1992) Cloning and functional characterization of a human A1 adenosine receptor. Biochem. Biophys. Res. Commun. 187, 919-926.

Lomasney, J. W., Lorenz, W., Allen, L. F., King, K., Regan, J. W., Yang-Feng, T. L., Caron, M. G., and Lefkowitz, R. J. (1990) Expansion of the $\alpha_2$-adrenergic receptor family: cloning and characterization of a human $\alpha_2$-adrenergic receptor subtype, the gene for which is located on chromosome 2. Proc. Natl. Acad. Sci. U.S.A. 87, 5094-5098.

Mayo, K. E. (1992) Molecular cloning and expression of a pituitary-specific receptor for growth hormone-releasing hormone. Mol. Endocrin. 6, 1734-1744.

Minegish, T., Nakamura, K., Takakura, Y., Ibuki, Y., and Igarashi, M. (1991) Cloning and sequencing of human FSH receptor cDNA. Biochem. Biophys. Res. Commun. 175, 1125-1130.

Minegish, T., Nakamura, K., Takakura, Y., Miyamoto, K., Hasegawa, Y., Ibuki, Y., and Igarashi, M. (1990) Cloning and sequencing of human LH/hCG receptor cDNA. Biochem. Biophys. Res. Commun. 172, 1049-1054.

Misrahi, M., Loosfelt, H., Atger, M., Sar, S., Guiochen-Mantel, A., Milgrom, E. (1990) Cloning sequencing and expression of human TSH receptor. Biochem. Biophys. Res. Commun. 166, 394-403.

Mita, S., Sadlock, J., Herbert, J., Schon, E. A. (1988) A cDNA specifying the human amyloid precursor protein (ABPP) encodes a 95-kDa polypeptide. Nuc. Acids Res. 16, 9351.

Mochizuki-D. Yuyama-Y. Tsujita-R. Komaki-H. Sagai-H. (1992) Cloning and expression of the human 5-HT1B-type receptor gene. Biochem-Biophys-Res-Commun. 185, 517-523.

Murphy, P. M. and McDermott, D. (1991) Functional expression of the human formyl peptide receptor in Xenopus oocytes requires a complementary human factor. J. Biol. Chem. 266, 12560-12567.

Murphy, P. M. and Tiffany, H. L. (1991) Cloning of complementary DNA encoding a functional human interleukin-8 receptor. Science 253, 1280-1283.

Nagayama, Y., Kaufman, K. D., Seto, P., and Rapoport, B. (1989) Molecular cloning, sequence and functional expression of the cDNA for the human thyrotropin receptor. Biochem. Biophys. Res. Commun. 165, 1184-1190.

Nakamuta-M. Takayanagi-R. Sakai-Y. Sakamoto-S. Hagiwara-H. Mizuno. Saito-Y. Hirose-S. Yamamoto-M. Nawata-H. (1991) Cloning and sequence analysis of a cDNA encoding human non-selective type of endothelin receptor. Biochem-Biophys-Res-Commun. 177, 34-39.

Nathans, J., and Hogness, D. S. (1984) Isolation and nucleotide sequence of the gene encoding human rhodopsin. Proc. Natl. Acad. Sci. U.S.A. 81, 4851-4855.

Nathans, J., Thomas, D., and Hogness, D. S. (1986) Molecular genetics of human color vision: The genes encoding blue, green, and red pigments. Science 232, 193-202.

Neote, K. DiGregorio, D., Mak, J. Y., Horuk, R., and Schall, T. J. (1993) Molecular cloning, functional expression, and signaling characteristics of a C—C chemokine receptor. Cell 72, 415-425.

Ogawa-Y. Nakao-K. Arai-H. Nakagawa-O. Hosoda-K. Suga-S. Nakanishi-S. Imura-H. (1991) Molecular cloning of a non-isopeptide-selective human endothelin receptor. Biochem-Biophys-Res-Commun. 178, 248-255.

Peralta, E. G., Ashkenazi, A., Winslow, J. W., Smith, D. H., Ramachandran, J., and Capon, D. J. (1987b). Distinct primary structures, ligand-binding properties, and tissue-specific expression of four human muscarinic acetylcholine receptors. EMBO J. 6, 3923-3929.

Pierce, K. D., Furlong, T. J., Selbie, L. A., and Shine, J. (1992) Molecular cloning and expression of an adenosine A2b receptor from human brain. Biochem. Biophys. Res. Commun. 187, 86-93.

Ramarao-C-S. Denker-J-M. Perez-D-M. Gaivin-R-J. Riek-R-P. Graham-R-M. (1992) Genomic organization and expression of the human $\alpha$ 1B-adrenergic receptor. J-Biol-Chem. 267, 21936-21945.

Regan, J. W., Kobilka, T. S., Yang-Feng, T. L., Caron, M. G., and Lefkowitz, R. J. (1988) Cloning and expression of a human kidney cDNA for a novel $\beta_2$-adrenergic receptor. Proc. Natl. Acad. Sci. U.S.A. 85, 6301-6305.

Sokoloff, P., Giros, B., Martres, M.-P., Bouthenet, M. L., Schwartz, J.-C. (1990) Molecular cloning and characterization of a novel dopamine receptor ($D_3$) as a target for neuroleptics. Nature 347, 146-151.

Sreedharan, S. P., Robichon, A., Peterson, K. E., and Goetzl, E. J. (1991) Cloning and expression of the human vasoactive intestinal peptide receptor. Proc. Natl. Acad. Sci. U.S.A. 88, 4986-4990.

Sunahara, R. K., Niznik, H. B., Weiner, D. M., Stormann, T. M., Brann, M. R., Kennedy, J. L., Gelernter, J. E., Rozmahel, R., Yang, Y., Israel, Y., Seeman, P., O'Dowd, B. F. (1990) Human dopamine $D_1$ receptor encoded by an intronless gene on chromosome 5. Nature 347, 80-83.

Takeda, Y., Chou, K. B., Takeda, J., Sachais, B. S., and Krause, J. E. (1991) Molecular cloning, structural characterization and functional expression of the human substance P receptor. Biochem. Biophys. Res. Commun. 179, 1232-1240.

Tanabe, Y., Hasu, H., Shigemoto, R., Nakanishi, S. (1992) A family of metabotropic glutamate receptors. Neuron 8, 169-179.

Van Tol, H. H., Bunzow, J. R., Guan, H. C., Sunahara, R. K. Seeman, P., Niznik, H. B., Civelli, O. (1991) Cloning of the gene for a human dopamine D4 receptor with high affinity for the antipsychotic clozapine. Nature 350, 610-614.

Vu, T.-K. H., Hung, D. T., Wheaton, V. I., and Coughlin, S. R. (1991) Molecular cloning of a functional thrombin receptor reveals a novel proteolytic mechanism of receptor activation. Cell 64, 1057-1068.

Weinshank, R. L., Zgombick, J. M., Macchi, M., Adham, N., Lichtblau, H., Branchek, T. A., and Hartig, P. R. (1990) Cloning, expression and pharmacological characterization of a human $\alpha_{2B}$-adrenergic receptor. Mol. Pharmacol. 38, 681-688.

Weinshank-R-L. Adham-N. Macchi-M. Olsen-M-A. Branchek-T-A. Hartig-P-R. (1991) Molecular cloning and characterization of a high affinity dopamine receptor (D1 beta) and its pseudogene. J-Biol-Chem. 266, 22427-22435.

Xie, G.-X., Miyajima, A., and Goldstein, A. (1992) Expression cloning of cDNA encoding a seven-helix receptor from human placenta with affinity for opioid ligands. Proc. Natl. Acad. Sci. U.S.A. 89, 4124-4128.

Yamada, Y., Post, S. R., Wang, K., Tager, H. S., Bell, G. I., Seino, S. (1992a) Cloning and functional characterization of a family of human and mouse somatostatin receptors expressed in brain, gastrointestinal tract and kidney. Proc. Natl. Acad. Sci. U.S.A. 89, 251-255.

Yamada, Y., Reisine, T., Law, S. F., Ihara, Y., Kubota, A., Kagimoto, S., Seino, M., Seino, Y., Bell, G. I., Seino, S., (1992b) Somatostatin receptors, an expanding gene family: Cloning and functional characterization of human SSTR3, a protein coupled to adenylyl cyclase. Mol. Endocrin. 6, 2136-2142.

Young, D., Waitches, G., Birchmeier, C., Fasano, O., and Wigler, M. (1986) Isolation and characterization of a new cellular oncogene encoding a protein with multiple transmembrane domains. Cell 45, 711-719.

Zhou, Q.-Y., Grandy, D. K., Thambi, L., Kushner, J. A., Van Tol, H. H. M., Cone, R., Pribnow, D., Salon, J., Bunzow, J. R., Civelli, O. (1990) Cloning and expression of human and rat $D_1$ dopamine receptors. Nature 347, 76-80.

Birnbaumer, M., Seibold, A., Gilbert, S., Ishido, M., Barberis, C., Antaramian, A., Brabet, P., Rosenthal, W., (1992) Molecular cloning of the receptor for human antidiuretic hormone. Nature 357,333-5.

Chhajlan, V., Wikberg, J.-E., (1992) Molecular cloning and expression of melanocycte stimulating hormone receptor cDNA. FEBS Lett. 309, 417-420.

Chi, L., Zhou, W., Prikhosan, A., Flanagan, C., Davidson, J. S., Golembo, M., Illing, N., Millar, R. P., Sealfon, S. C. (1993) Cloning and characterization of human gonadotropin-releasing hormone receptor. Mol. Cell Endrocrinol, 91,R1-R6.

Hess, J.-F., Borkowski, J.-A., Young, G.-S., Strader, C.-D., Ransom, R.-W., (1992) Cloning and pharmacological characterization of a human bradykinin (BK-2) receptor. Biochem-Biophys-Res-Commun. 184, 260-8.

Mountjoy, K. G., Robbins, L. S., Mortrud, M. T., Cone R. D., (1992) The cloning of a family of genes that encode the melanocortin receptors. Science 257, 1248-1251.

Pisegna, J. R., de-Weerth, A., Huppi, K., Wank, S. A., (1992) Molecular cloning of the human brain and gastric cholecystokinin receptor: structure, functional expression and chromosomal localization. Biochem-Biophys-Res-Commun. 189,296-303.

Zhou, Q. Y., Grandy, D. K., Thambi, L., Kushner, J. A., Van Tol, H. H. M., Cone, R., Pribnow, D., Salon, J., Bunzow, J. R., Civelli, O., (1990) Cloning and expression of human and rat $D_1$ dopamine receptors. Nature 347,76-80.

TABLE 3

Detection of C5a production in yeast by ELISA.

| | R−L− | R+L− | R−L+ | R+L+ |
|---|---|---|---|---|
| [C5a] in culture | n.d. | n.d. | 0.64 ng/ml = 77 nM | 0.5 ng/ml = 60 nM |
| [C5a] released from lysed cells* | n.d. | n.d. | 0.8 ng/ml = 97 nM | 0.6 ng/ml = 73 nM |

C5a was detected by enzyme-linked immunosorbent assay (ELISA). Molar concentrations were calculated using MW = 8273 as predicted by C5a sequence.
*Determined by pelleting cells, resuspending cells in the original volume, breaking yeast with glass beads and assaying the resulting supernatant.
n.d. = not done

TABLE 4

Coupling of the C5a receptor to Gα chimeras in yeast.
ChimeraExpressionResult
Context $GPA1_{41}$-Gαi2 single copy, Good signal to noise ratio:
integrated, efficient coupling to yeast
GPA1 promoterβγ.
$GPA1_{41}$-Gαi3 single copy, Poor signal to noise ratio:
integrated, high background due to poor
GPA1 promoter coupling to yeast βγ, high
LIRMA*.
GPA1βam-Gαi2 low copy plasmid, Signal equal to that with
GPA 1 promoter $GPA1_{41}$-Gαi2, however, background
is greater.
GPA1βam-Gα16 low copy plasmid, Poor signal to noise ratio,
GPA1 promoter high background due to poor
coupling to yeast βγ, high
LIRMA*.
GPA1βam-Gα slow copy plasmid, Unacceptably high background
GPA1 promoter due to poor coupling to
yeast β', high LIRMA*.

*LIRMA = Ligand Independent Receptor Mediated Activation. With this phenomenon, there is an increase in growth on selective media for strains containing heterologous receptor in the absence of ligand. It is possible that some receptor antagonists would decrease LIRMA. It has been noted (Milano, et al. 1994) that specific antagonists reduce LIRMA of the β2 adrenergic receptor when that receptor is overexpressed in transgenic mice.

LIRMA may be exploited in several ways, including the identification of antagonists capable of reducing the Phenomenon. A subset of antagonists would be expected to affect the receptor conformation in such a way as to prevent the downstream signalling that occurs in the absence of agonist. LIRMA can be exploited to identify new G protein-coupled receptors by expressing cDNA clones in yeast strains expressing those chimeric G proteins which couple only poorly to yeast βγ. In addition, LIRMA may permit the identification of inhibitors that are specific for G proteins.

TABLE 5

Sequence alignments of N-terminal
regions of Gα subunits and N-terminal
sequences of $GPA_{41}$-Gα hybrid proteins.

A. Alignment of GPA1 with Gα Subunits

GPA1
MGC.TVSTQTIGDESDPFLQNKRANDVIEQSLQLEKQRDKNEIKLLLLGA
GESGKSTVLKQLKLLHQ..... (SEQ ID NO: 82)

Gαs
MGCLGTS..KTEDQRNEEKAQREANKKIEKQLQKDKQVYRATHRLLLLGA
GESGKSTIVKQMRILHV..... (SEQ ID NO: 83)

Gαi2
MGC.TVS........AEDKAAAERSKMIDKNLREDGEKAAREVKLLLLGA
GESGKSTIVKQMKIIHE..... (SEQ ID NO: 84)

Gαi3
MGC.TVS........AEDKAAVERSKMIDRNLREDGEKAAKEVKLLLLGA
GESGKSTIVKQMKIIHE..... (SEQ ID NO: 85)

Gα16
MARSLTWRCCPWCLTEDEKAAARVDQEINRILLEQKKQDRGELKLLLLGP
GESGKSTFIKQMRIIHG..... (SEQ ID NO: 86)

TABLE 5-continued

Sequence alignments of N-terminal
regions of Gα subunits and N-terminal
sequences of GPA$_{41}$-Gα hybrid proteins.

B. GPA$_{41}$-Gα Hybrids

GPA$_{41}$-GαS
MGC.TVSTQTIGDESDPFLQNKRANDVIEQSLQLEKQRDKNERKLLLLGA
GESGKSTIVKQMRILHV..... (SEQ ID NO: 87)

GPA$_{41}$-Gαi2
MGC.TVSTQTIGDESDPFLQNKRANDVIEQSLQLEKQRDKNEVKLLLLGA
GESGKSTIVKQMKIIHE..... (SEQ ID NO: 88)

GPA$_{41}$-Gαi3
MGC.TVSTQTIGDESDPFLQNKRANDVIEQSLQLEKQRDKNEVKLLLLGA
GESGKSTIVKQMKIIHE..... (SEQ ID NO: 89)

GPA$_{41}$-Gα16
MGC.TVSTQTIGDESDPFLQNKRANDVIEQSLQLEKQRDKNELKLLLLGP
GESGKSTFIKQMRIIHG..... (SEQ ID NO: 90)

TABLE 6

Coupling of Gα switch region hybrids to the
pheromone response pathway.

| Protein | GPA1 amino acid sequences | Gαs amino acid sequences | Phenotype |
|---|---|---|---|
| GPA1 | 1-472 | none | Couples with Gβγ |
| GαS | none | 1-394 | Couples with Gβγ weakly |
| GPA$_{41}$-S | 1-41 | 42-394 | Couples with Gβγ weakly |
| SGS | 297-333 | 1-201 + 237-394 | Does not couple with Gβγ |
| GPA$_{41}$-SGS | 1-41 + 297-333 | 42-201 + 237-394 | Couples with Gβγ weakly |

TABLE 8

G protein-coupled receptors that couple through Gαi:

M2 muscarinic acetylcholine
M4 muscarinic acetylcholine
adenosine A1
adenosine A3
$\alpha_{2A}$-adrenergic
$\alpha_{2B}$-adrenergic
$\alpha_{2C}$-adrenergic
bradykinin B$_2$
cannabinoid
D2 dopamine
D4 dopamine
ET$_B$ endothelin
formyl-methionyl peptide receptor FPR$_1$
metabotropic glutamateR$_2$
metabotropic glutamateR$_3$
metabotropic glutamateR$_4$
5HT$_{1A}$ (serotonin)
5HT$_{1B}$ (serotonin)
5HT$_{1D}$ (serotonin)
5HT$_{1E}$ (serotonin)
5HT$_{1F}$ (serotonin)
neuropeptide Y
delta opioid
prostaglandin EP3
somatostatin 2
somatostatin 3
somatostatin 4
thrombin
C5a
platelet activating factor
angiotensin AT$_1$
angiotensin AT$_2$
IL-8
MCP1A
MCP1B

TABLE 7

Gα Subunit Alignment—"Switch Region"

β2β3α2β4

GPA1 RIDTTGITETEFNIGSSKFKVLDAGGQRSERKKWIHCFEGITAVLFVLAMSEYDQMLFEDER
(SEQ ID NO: 111)

GαS  .VL.S..F..K.QNDKVN.HMF.V....D......Q..NDV..II..V.S.S.NMVIR..NQ
(SEQ ID NO: 112)

Gαi2 .VK....V..H.TFKDLH..MF.V................V..II.CV.L.A..LV.ADE.M
(SEQ ID NO: 113)

Gαi3 .VK....V..H.TFKDLY..MF.V................V..II.CV.L.D..LV.A...E
(SEQ ID NO: 114)

Gαo  .VK....V..H.TFKNLH.RLF.V................DV..II.CN.L.G...V.H...T
(SEQ ID NO: 115)

Gα11 .VP....I.YP.DLENII..MV.................NV.SIM.LV.L.....C.E.NNQ
(SEQ ID NO: 116)

Gα16 .MP....N.YC.SVQKTNL.IV.................N.I.LIYLASL.....V.V.SDN
(SEQ ID NO: 117)

TABLE 9

STRAINS

| NUMBERα | HOST GENOTYPE | PLASMID 1 | PLASMID 2 | PLASMID 3 |
|---|---|---|---|---|
| CY4874 | gpa1*1163 far1*1442 tbt1-1 fus1-HIS3 can1 ste14::trp1::LYS2 ste3*1156 lys2 ura3 leu2 trp1 his3 | TRP1 GPA1p-gpa41/Gαi20205L CEN6 ARS4 AmpR | URA3 2mu-ori REP3 AmpR fus1-lacZ | |
| CY4877 | gpa1*1163 far1*1442 tbt1-1 fus1-HIS3 can1 ste14::trp1::LYS2 ste3*1156 lys2 ura3 leu2 trp1 his3 | TRP1 GPA1p-gpa41/Gαi2 hybrid CEN6 ARS4 AmpR | URA3 2mu-ori REP3 AmpR fus1-lacZ | |
| CY4901 | far1*1442 tbt1-1 fus1-HIS3 can1 ste14::trp1::LYS2 ste3*1156 gpa1(41)-Gαi2 lys2 ura3 leu2 trp1 his3 | LEU2 PGKpC5aR(P184L) 2mu-ori REP3 AmpR | URA3 2mu-ori REP3 AmpR fus1-lacZ | |
| CY4904 | far1*1442 tbt1-1 fus1-HIS3 can1 ste14::trp1::LYS2 ste3*1156 gpa1(41)-Gαi2 lys2 ura3 leu2 trp1 his3 | LEU2 PGKpC5aR 2mu-ori REP3 AmpR | URA3 2mu-ori REP3 AmpR fus1-lacZ | |
| CY5058 | gpa1*1163 far1*1442 tbt1-1 fus1-HIS3 can1 ste14::trp1::LYS2 ste3*1156 lys2 ura3 leu2 trp1 his3 | LEU2 PGKp 2mu-ori REP3 AmpR | URA3 2mu-ori REP3 AmpR f1ori | AmpR TRP1 2mu fus1-lacZ |

General References

Anderson M. P., Gregory R. J., Thompson S., Souza D. W., Paul, S. et al. (1991) Demonstration that CFTR is a chloride channel by alteration of its anion selectivity. Science 253, 202-205.

Artemeyev N. O., Rarick H. M., Mills J. S., Skiba N. P., and Hamm H. E. (1992) Sites of interaction between rod G-protein α-subunit and cGMP-phosphodiesterase γ-subunit. J. Biol. Chem. 267, 25067-25072.

Banerjee S., Anderson G. D., Luthra H. S., David C. S. (1989) Influence of complement CS and V beta T cell receptor mutations on susceptibility to collagen-induced arthritis in mice. J. Immunol. 142: 2237-2243.

Barr P. J., Mason O. B., Landsberg K. E., Wong P. A. et al. (1991-) cDNA and gene structure for a human subtilisin-like protease with cleavage specificity for paired basic amino acid residues. DNA Cell Biol. 10, 319-328.

Benjannet, S., Rondeau N., Day R., Chretien M., Seidah N. G. (1991) PC1 and PC2 are proprotein convertases capable of cleaving proopiomelanacortin at distinct pairs of basic residues. Proc. Natl. Acad. Sci. USA 88:3564-3568.

Bianchi A. B., Fischer S. M., Robles A. I., Rinchik E. M., Conti C. J. (1993) Overexpression of cyclin D1 in mouse skin carcinogenesis. Oncogene8, in press. like protease with cleavage specificity for paired basic amino acid residues. DNA Cell Biol. 10, 319-328.

Benjannet, S., Rondeau N., Day R., Chretien M., Seidah N. G. (1991) PC1 and PC2 are proprotein convertases capable of cleaving proopiomelanacortin at distinct pairs of basic residues. Proc. Natl. Acad. Sci. USA 88:3564-3568.

Bianchi A. B., Fischer S. M., Robles A. I., Rinchik E. M., Conti C. J. (1993) Overexpression of cyclin D1 in mouse skin carcinogenesis. Oncogene 8, in press.

Birkenbach M., Josefsen K., Yalamanchili R., Lenoir G., Kieff E. (1993) Epstein-Barr Virus-induced genes: First lymphocyte-specific G protein-coupled peptide receptors J. Virol. 67, 2209-2220.

Bray P., Carter A., Simons C., Guo V., Puckett C., Kamholz J., Spiegel A., Nirenberg M. (1986): Human cDNA clones for four species of Gαs signal transduction protein. Proc Natl Acad Sci USA 83:8893:8897.

Bray p., Carter A., Guo V., Puckett C., Kamholz J., Spiegel A., Nirenberg M. (1987): Human cDNA clones for an α subunit of Gi signal-transducing protein. Proc Natl Acad Sci USA 84:5115-5119.

Buratowski S., Hahn S., Sharp P. A., Guarente L. (1988) function of a yeast. TATA element-binding protein in a mammalian transcription system. Nature 334, 37.

Burkholder A. C. and Hartwell L. H. (1985) The yeast α-factor receptor: Structural properties deduced from the sequence of the STE2 gene. Nuc. Acids Res. 13, 8463.

Cavallini B., Huet J., Plassat, J.-L., Sentenac A., Egly J.-M., Chambon P. (1988) A yeast activity can substitute for the HeLa cell TATA box factor. Nature 334, 77.

Chen W J, Andres D. A., Goldstein J. L., Brown M. S. (1991) Cloning and expression of a cDNA encoding the subunit of rat p21$^{ras}$ protein farnesyltransferase. Cell 66:327-334.

Choi K., Chen C.-J., Kriegler M., Roninson I. B. (1988) An altered pattern of cross-resistance in multidrug resistant human cells results from spontaneous mutation in the mdr1 (P-glycoprotein) gene. Cell 53, 519-529.

Clark K L, Dignard D., Thomas D Y, Whiteway M. (1993) Interactions among the subunits of the G proteins involved in Saccharomyces cerevisiae mating. Mol. Cell. Biol. 13:1-8.

Coleman D. E., Berghuis A. M., Lee E., Linder M. E., Gilman A. G., Sprang S. R. (1994) Structures of Active Conformations of Giα1 and the Mechanism of GTP Hydrolysis. Science 265:1405-1412.

Conklin, B. R., Farfel, Z., Lustig, K. D., Julius, D., and H. R. Blurne (1993) Substitution of three amino acids switches receptor specificity of Gqα to that of Giα. Nature 363,274-276.

Crawford M. H., Grover F. L., Kolb W. P., McMahan C. A. et al. (1988) Complement and neutrophil activation in the pathogenesis of ischemic myocardial injury. Circulation 78: 1449-1458.

Crews C. M., Allessandrini A., Erikson R. L. (1992) The primary structure of MEK, a protein kinase that phophorylates the ERK gene product. Science 258, 478-480.

Cross F. (1988) DAF1, a mutant gene affecting size control, pheromone arrest, and cell cycle kinetics of Saccharomyces cerevisiae. Mol. Cell. Biol. 8, 4675-4684.

Dassa E. (1990) Cellular localization of the MALg protein from the maltose transport system in Escherichia coli K12. Mol. Gen. Genet. 222:33-36.

Dassa E. and Hofnung M. (1985) Sequence of gene malG in E. coli K12: homologies between integral membrane components from binding protein-dependent transport systems. EMBO J. 4:2287-2293.

Dietzel C. and Kurjan J. (1987) Effects of expression of mammalian Gα proteins on the yeast pheromone response signal transduction pathway. Cell 50, 1001-1010.

Dmochowska A., Dignard D., Henning D., Thomas D. Y., Bussey H. (1987) Yeast KEX1 gene encodes a putative protease with a carboxypeptidase B-like function involved in killer toxin and α-factor precursor processing. Cell 50, 573.

Duchateau J., Haas M., Schreyen H., Radoux L. et al. (1984) Complement activation in patients at risk of developing the adult respiratory distress syndrome. Am. Rev. Respir. Dis. 130: 1058-1064.

Ehrmann M., Boyd D., Beckwith J. (1990) Genetic analysis of membrane protein topology by a sandwich gene fusion approach. Proc. Natl. Acad. Sci. 87, 7574-7578.

Elledge S. J. and Spottswood M. R. (1991) A new human p34 protein kinase, CDK2, identified by complementation of a cdc28 mutation in *Saccharomyces cerevisiae*, is a homolog of Xenopus Eg1. EMBO J. 10, 2653-2659.

Emter O., Mechler B., Achstetter T., Muller H., Wolf D. H. (1983) Yeast pheromone α-factor is synthesized as a high molecular weight precursor. Biochem. Biophys. Res. Commun. 116, 822-829.

Endicott J. A., Sarangi F., Ling V. (1991) Complete cDNA sequences encoding the Chinese hamster P-glycoprotein gene family. DNA Sequence 2, 89-101.

Engleman D. A., Steitz T. A., Goldman A. (1986) Identifying nonpolar transbilayer helices in amino acid sequences of membrane proteins. Ann. Rev. Biophys. Chem. 15, 321-353.

Etienne G., Armau E., Tiraby G. (1990) A screening method for antifungal substances using *Saccharomyces cerevisiae* strains resistant to polyene macrolides. J. Antibiot. 43, 199-206.

Fikes-J. D., Becker D. M., Winston F., Guarente L. (1990) Striking conservation of TFIID in *Schizosaccaharomyces pombe* and *Saccharomyces cerevisiae*. Nature 346, 291.

Franke A. E., Andrews G. C., Stimler-Gerard N., Gerard C. J. and Showell H. J. (1988) Human C5a anaphylatoxin: Gene synthesis, expression, and recovery of biologically active material from *Escherichia coli*. Methods in Enzymology 162: 653-668.

Gallego C., Gupta S. K., Winitz S., Eisfelder B. J., Johnson G. L. (1992) Myristoylation of the Gαi2 polypeptide, a G protein α subunit, is required for its signaling and transformation functions. Proc. Natl. Acad. Sci. USA 89, 9695-9699.

Garritsen, A., van Galen, P. J. M., and W. F. Simonds (1993) The N-terminal coiled-coil domain of β is essential for γ association: A model for G-protein βγ subunit interaction. Proc. Natl. Acad. Sci. USA 90, 7706-7710.

Gasch A. A., Hoffman M., Horikoshi M., Roeder R., Chua N. (1990) Arabodopsis thaliana contains two genes for TFIID. Nature 346, 390.

Gelfand J. A., Donelan M., Hawiger A., Burke J. F. (1982) Alternative complement pathway activation increases mortality in a model of burn injury in mice. J. Clin. Invest 70: 1170-1176.

Gerard N. P. and Gerard C. (1990) Construction and expression of a novel recombinant anaphylatoxin, C5a-N19, a probe for the human C5a recentor. Biochemistry 29, 9274-9281.

Glotzer M., Murray A. W., Kirschner M. W. (1991) Cyclin is degraded by the ubiquitin pathway. Nature 349, 132-138.

Gomez R., Goodman L E; Tripathy S K; O'Rourke E; et al. Purified yeast protein farnesyltransferase is structurally and functionally similar to its mammalian counterpart. (1993) Biochem. J. 289, 25-31.

Gotoh Y., Nishida E., Shimanuki M., Toda T., Imai Y., Yamamoto M. (1993) *Schizosaccharomyces pombe* SPK1 is a tyrosine-phosphorylated protein functionally related to Xenopus mitogen-activated protein kinase. Mol. Cell. Biol. 13, 6427-6434.

Graf R., Mattera R., Codina J., Estes M., Birnbaumer L. (1992) A truncated recombinant α subunit of Gi3 with a reduced affinity for βγ dimers and altered guanosine 5'-3-0-(Thio) triphosphate binding. J. Biol. Chem. 267, 24307-24314.

Gros P., Dhir R., Croop J., Talbot F. (1991) A single amino acid substitution strongly modulates the activity and substrate specificity of the mouse mdr1 and mdr3 drug efflux pumps. Proc. Natl. Acad. Sci. 88, 7289-7293.

Guarente L. (1983) Yeast promoters and lacZ fusions designed to study expression of cloned genes in yeast. Methods Enzymol. 101, 181-191.

Guarente L. (1988) UASs and enhancers: Common mechanism of transcriptional activation in yeast and mammals. Cell 52, 303.

Guarente L. in The molecular and cellular biology of the yeast Saccharomyces: Gene Expression, Jones E. W., Pringle J. R., Broach J. R., eds., Cold Spring Harbor Laboratory Press, New York, 1992, p49-98.

Hadwiger J. A., Wittenberg C., Richardson H. E., de Barros Lopes M., Reed S. I. (1989) A family of cyclin homologs that control the G1 phase in yeast. Proc. Natl. Acad. Sci. 86, 6255-6259.

Hagen D. C., McCaffrey G., Sprague G. F. (1986) Evidence the yeast STE3 gene encodes a receptor for the peptide pheromone a-factor: gene sequence and implications for the structure of the presumed receptor. Proc. Natl. Acad. Sci. 83, 1418.

Hammerschmidt D. E., Weaver L. J., Hudson L. D., Craddock P. R., Jacob H. S. (1980) Association of complement activation and elevated plasma-C5a with adult respiratory distress syndrome. Pathophysiological relevance and possible prognostic value. Lancet 1:947-949.

Hara M., Akasaka K., Akinaga S., Okabe M., Nakano H., Gomez R., Wood D., Uh M., Tamanoi F. (1993) Identification of Ras farnesyltransferase inhibitors by microbial screening. Proc. Natl. Acad. Sci. 90, 2281-2285.

Harbury P. B., Zhang T., Kim P. S. Alber T. (1993) A switch between two-, three-, and four-stranded coiled coils in GNC4 leucine zipper mutants. Science 262, 1401-1407.

Harshman K. D., Moye-Rowley W. S., Parker C. S. (1988) Transcriptional activation by the SV40 AP-1 recognition element in yeast is mediated by a factor similar to AP-1 that is distinct from GCN4. Cell 53, 321.

He B., Chen P., Chen S.-Y., Vancura K. L., Michaelis S., Higgins C. F., Haag P. D., Nikaido K., Aedeshir F., Garcia G. et al. (1982) Complete nucleotide sequence and identification of membrane components of the histidine transport operon of *S. typhimurium*. Nature 298, 723-727.

Hoey T., Dynlacht B. D., Peterson M. G., Pugh B. F., Tjian R. (1990) Isolation and characterization of the Drosophila gene encoding the TATA box binding protein, TFIID. Cell 61, 1179.

Hoffman A., Sinn E., Yamamoto T., Wang J., Roy A., Horikoshi M., Roeder R. G. (1990) Highly conserved core domain and unique N terminus with presumptive regulatory motifs in a human TATA factor (TFIID). Nature 346, 387.

Howe O P. H., Draetta G., Leof E. B. (1991) Transforming growth factor 1 inhibition of p34cdc2 phosphorylation and histone H1 kinase activity is associated with G1/S-phase growth arrest. Mol. Cell. Biol. 11, 1185-1194.

Hrycyna C. A., Sapperstein S. K., Clarke S., Michaelis S. (1991) The *Saccharomyces cerevisiae* STE14 gene encodes a methyltransferase that mediates C-terminal methylation of a-factor and RAS proteins. EMBO J. 10, 1699.

Hughes D. A., Ashworth A., Marshall C. J. (1993) Complementation of byr1 in fission yeast by mammalian MAP kinase kinase requires coexpression of Raf kinase. Nature 364, 349-352.

Hyde S. C., Emsley P., Hartshorn M., Mimmack M. M., Gileadi U. et al. (1990) Structural model of ATP-binding proteins associated with cystic fibrosis, multidrug resistance and bacterial transport. Nature 346, 362-365.

Jabbar, M. A., Sivasubramanian, N., Nayak, D. P. (1985) Influenza viral (A/WSN/33) hemagglutinin is expressed and glycosylated in the yeast *Saccharomyces cerevisiae*. Proc. Natl. Acad. Med. U.S.A. 82, 2019-2023.

Journot L., Pantaloni C., Poul M.-A., Mazarguil H., Bockaert J., Audigier Y. (1990) Amino acids 367-376 of the Gsα subunit induce membrane association when fused to soluble amino-terminal delted Giα subunit. J. Biol. Chem. 265, 9009-9015.

Julius D., Brake A., Blair L., Kunisawa R., Thorner J. (1984) Isolation of the putative structural gene for the lysine-arginine-cleaving endopeptidase required for processing of yeast prepro-αfactor. Cell 37, 1075-1089.

Julius D., Schekman, Thorner J. (1984) Glycosylation and processing of prepro-α-factor through the yeast secretory pathway. Cell 36, 309-318.

Julius D., Blair L., Brake A., Sprague G., Thorner J. (1983. Yeast α-factor is processed from a larger precursor polypeptide: the essential role of a membrane-bound dipeptidyl aminopeptidase. Cell 32, 839.

Kakidani H. and Ptashne M. (1988) GAL4 activates gene expression in mammalian cells. Cell 52, 161.

Kang, Y.-S., Kane J., Kurjan J., Stadel J. M., Tipper D. J. (1990) Effects of expression of mammalian Gα and hybrid mammalian-yeast Gα proteins on the yeast pheromone response signal transduciton pathway. Mol. Cell. Biol. 10, 2582-2590.

Kao C. C., Lieberman P. M., Schmidt M. C., Zhou Q., Pei R., Berk A. J. (1990) Cloning of a transcriptionally active human TATA binding factor. Science 248, 1646.

Kay B. K., Adey N. B., He Y.-S., Manfredi J. P., Mataragnon A. H., Fowlkes D. F. (1993) An M13 phage library displaying random 38-amino-acid peptides as a source of novel sequences with affinity to selected targets. Gene 128, 59-65.

Keyomarsi K. and Pardee A. B. (1993) Redundant cyclin overexpression and gene amplification in breast cancer cells. Proc. Natl. Acad. Sci. 90, 1112-1116.

Khavari P. A., Peterson C. L., Tamkun J. W., Mendel D. B., Crabtree G. R. (1993) BRG1 contains a conserved domain of the SWI2/SNF2 family necessary for normal mitotic growth and transcription. Nature 366, 170-174.

King K., Dohlman H. G., Thorner J., Caron M. G., Lefkowitz R. J. (1990) Control of yeast mating signal transduction by a mammalian β2-adrenergic receptor and Gsα subunit. Science 250, 121-123.

Kingsman S. M., Kingsman A. J., Mellor J. (1987) The production of mammalian proteins in *Saccharomyces cerevisiae*. TIBTECH 5, 53-57.

Koff A., Cross F., Fisher A., Schumacher J., Leguellec K., Phillipe M., Roberts J. M. (1991) Human cyclin E, a new cyclin that interacts with two members of the CDC2 gene family. Cell 66, 1217-1228.

Koff A., Ohtsuli M., Polyak K., Roberts J. M. Massague J. (1993) Negative regulation of G1 in mammalian cells: inhibition of cyclin E-dependent kinase by TGF-β. Science 260, 536-539.

Kohl N. E., Mosser S., deSolms S. J., Giuliani E. A., Pompliano D. L., Graham S. L., Smith R. L., Scolnick E. M., Oliff A., Gibbs J. B. (1993) Selective inhibition of ras-dependent transformation by a farnesyltransferase inhibitor. Science 260, 1934-1937.

Kohl N E, Diehl R. E., Schaber M. D., Rands E., Soderman D. D., He B., Moores S. L., Pompliano D. L., Ferro-Novick S., Powers S. et al. (1991) Structural homology among mammalian and *Saccharomyces cerevisiae* isoprenyl-protein transferases. J. Biol. Chem. 266, 18884-18888.

Korner, J., Chun J., Harter D., Axel R. (1991) Isolation and functional expression of a mammalian prohormone processing enzyme, murine prohormone convertase 1. Proc. Natl. Acad. Sci USA 88:6834-6838.

Kouba M; Vanetti M; Wang X; Schafer M; Hollt V (1993) Cloning of a novel putative G-protein-coupled receptor (NLR) which is expressed in neuronal and lymphatic tissue. FEBS Lett 321, 173-178.

Kramer R. A., Schaber M. D., Skalka A. M., Ganguly K., Wong-Staal F., Reddy E. P. (1086) HTLV-III gag protein is processed in yeast cells by the virus pol-protease.

Kreil G. (1990) Processing of precursors by dipeptidylaminopeptidases: a case of molecular ticketing. Trends Biochem. Sci. 15, 23.

Kuchler K., Sterne R. E., Thorner J. (1989) *Saccharomyces cerevisiae* STE6 gene product: a novel pathway for protein export in eukaryotic cells. EMBO J. 8, 3973.

Kurjan, J., Herskowitz, I. (1982) Structure of a yeast pheromone gene (MF): a putative α-factor precursor contains four tandem copies of mature α-factor. Cell 30, 933-943.

Kurjan J. (1985) α-factor structural gene mutations in yeast: effects on α-factor production and mating. Mol. Cell. Biol. 5, 787-796.

Kyte and Doolittle (1982) A simple method for displaying the hydropathic character of a protein. J. Molec. Biol. 157, 105-132.

Lambright D G, Noel J P, Hamm, H E, Sigler, P B (1994) Structural determinants for activation of the α-subunit of a heterotrimeric G protein. Nature 369:621-628.

Lammie G. A., Fantl V., Smith R., Schuuring E., Brookes S., Michalides R., Dickson C., Arnold A. Peters G. (1991) D11S287, a putative oncogene on chromosome 11q13, is amplified and expressed in squamous cell and mammary carcinomas and linked to BCL-1. Oncogene 6, 439-444.

Leberer E., Dignard D., Hougan L., Thomas D Y, Whiteway M. (1992) Dominant-negative mutants of a yeast G-protein b subunit identify two functional regions involved in pheromone signalling. EMBO J. 11:4805-4813.

Lee E., Taussig R., Gilman A. G. (1992) The G226A Mutant of Gsα Highlights the Requirement for Dissociation of G Protein Subunits. J. Biol. Chem. 267:1212-1218.

Lee K. S., Irie K., Gotoh Y., Watanabe Y., Arakai H., Nishida E., Matsumoto K., Levin D. E. (1993) A yeast mitogen-activated protein kinase homolog (Mpk1p) mediates signalling by protein kinase C. Mol. Cell. Biol. 13, 3067-3075.

Lee M. G. and Nurse P. (1987) Complementation used to clone a human homologue of the fission yeast cell cycle control gene cdc2. Nature 327, 31-35.

Lew D. J., Dulic V., Reed S. I. (1991) Isolation of three novel human cyclins by rescue of G1 cyclin (Cln) function in yeast. Cell 66, 1197-1206.

Linder M. E., Pang I.-H., Duronio R. J., Gordon J. I., Sternweis P. C., Gilman A. G. (1991) J. Biol. Chem. 266, 4654-4659.

Lupas, A. N., Lupas J. M., Stock J. B. (1992) Do G protein subunits associate via a three-stranded coiled coil? FEBS Lett. 314, 105-108.

Ma J., Przibilla J., Bogorad L., Ptashne M. (1988) Yeast activators stimulate plant gene expression. Nature 334, 631.

Manney T. R., Duntze W., Betz R. (1981) The isolation, characterization, and physiological effects of the *S. cerevisiae* sex pheromones. In *Sexual interactions in eukaryotic microbes* (ed. D. H. O'Day et al.), p 21. Academic Press, New York.

Markby, D. S., Onrust, R., and Bourne, H. R. (1993) Separate GTP binding and GTPase activating domains of a Gα subunit. Science 262: 1805-1901.

Masters, Stroud, and Bourne (1986) Protein Engineering 1:47-54.

Matsushime H., Roussel M. F., Ashmun R. A., Scherr C. J. (1991) Colony-stimulating factor 1 regulates novel cyclins during the G1 phase of the cell cycle. Cell 65, 701-713.

Mattera R., Codina J., Crozat A., Kidd V., Woo S L C, Birnbaumer L. (1986): Identification by molecular cloning of two forms of the α-subunit of the human liver stimulatory (Gs) regulatory component of adenylate cyclase. FEBS Lett 206:36-41.

McDonnell D. P., Nawaz Z., Densmore C., Weigel N. L. et al. (1991) High level expression of biologically active estrogen receptor in *Saccharomyces cerevisiae*. J. Steroid Biochem. Mol. Biol. 39, 291-297.

Metzger, D., Losson R., Bornert, J. M., Lemoine Y., Chambon P. (1992) Promoter specificity of the two transcriptional activation functions of the human oestrogen receptor in yeast. Nuc. Acids Res. 20, 2813-2817.

Metzger D., White J. H., Chambon P. (1988) The human cestrogen receptor functions in yeast. Nature 334, 31.

Milano, C. A., Allen, L. F., Rockman, H. A., Dolber., P. C., McMinn, T. R., Chien, K. R., Johnson, T. D., Bond R. A., Lefkowitz R. J. (1994) Enhanced myocardial function in transgenic mice overexpressing the β2-adrenergic receptor. Science 264, 582-586.

Mimura C. S., Holbrook S. R., Ames G. F.-L. (1991) Structural model of the nucleotide binding conserved component of periplasmic permeases. Proc. Natl. Acad. Sci. 88, 84-88.

Moir D T; Davidow L S. (1991) Production of proteins by secretion from yeast. Methods Enzymol 194, 491-507.

Motokura T., Bloom T., Kim H. G., Juppner H., Ruderman J. V., Kronenberg H. M., Arnold A. (1991) A novel cyclin encoded by a bcl1-linked candidate oncogene. Nature 350, 512-515.

Moye-Rowley W. S., Harshman K. D., Parker C. S. (1989) Yeast YAP1 encodes a novel form of the jun family of transcriptional activator proteins. Genes Dev. 3, 283.

Mumby, S. M., Heukeroth R. O., Gordon J. I., Gilman A. G. (1990) G protein Gα-subunit expression, myristoylation, and membrane association in COS cells. Proc. Natl. Acad. Sci. USA 87, 728-732.

Nakafuku M., Itoh H. Nakamura S., Kazioro Y. (1987) Occurrence in *Saccharomyces cerevisiae* of a gene homologous to the cDNA coding for the α subunit of mammalian G proteins. Proc. Natl. Acad. Sci. 84, 2140-2144.

Nakagawa T., Hosaka M., Torii S., Watanabe T. et al. (1993) Identification and functional expression of a new member of the mammalian Kex-2-like processing endoprotease family: its striking structural similarity to PACE4. J. Biochem. (Tokyo) 113, 132-135.

Nakayama K., Hosaka M., Hatsuzawa K., Murakami K. (1991) Cloning and functional expression of a novel endoprotease involved in prohormone processing at dibasic sites. J. Biochem. 109, 803-806.

Nakayama-K., Kim W. S., Torii S., Hosaka M. et al. (1992) Identification of a fourth member of the mammalian endoprotease family homologous to the yeast Kex2 protease. Its testis specific expression. J. Biol. Chem. 267, 5897-5900.

Nakayama N., Miyajima A., Arai K. (1985) Nucleotide sequences of STE2 and STE3, cell type-specific sterile genes from *Saccharomyces cerevisiae*. EMBO J. 4, 2643.

Nash R., Tokiwa G, Awand S., Erickson K., Futcher A. B. (1988) WHI1+ gene of *Saccharomyces cerevisiae* tethers division to cell size and is a cyclin homolog. EMBO J. 7, 4335-4346.

Neer E. J., Pulsifer L., Wolf L. G. (1988) The amino terminus of G protein a subunits is required for interaction with βγ. J. Biol. Chem. 263, 8996-9000.

Neiman A. M., Stevenson B. J., Xu H. P., Sprague G. F. et al. (1993) Functional homology of protein kinases required for sexual differentiation in *Schizosaccharomyces pombe* and *Saccharomyces cerevisiae* suggests a conserved signal transduction module in eukaryotic organisms. Mol. Biol. Cell. 4, 107-120.

Neote, K. DiGregorio, D., Mak, J. Y., Horuk, R., and Schall, T. J. (1993) Molecular cloning, functional expression, and signaling characteristics of a C—C chemokine receptor. Cell 72, 415-425.

Noel J. P., Hamm H. E., Sigler P. B. (1993) The 2.2 A crystal structure of transducin-αcomplexed with GTPγS. Nature 366, 654-663.

Norman C., Runswick M., Pollock R., Treisman R. (1988) Isolation and properties of cDNA clones encoding SRF, a transcription factor that binds to the c-fos serum response element. Cell 55, 989.

Oeda, K., Sakaki, T., Ohkawa, H. (1985) Expression of rat liver cytochrome P-450MC cDNA in *Saccharomyces cerevisiae*. DNA 3, 203-210.

Ogden, J. E., Stanway, C., Kuim, S., Mellor, J., Kingsman, A. J., and Kingsman, S. M. (1986) Efficient expression of the *Saccharomyces cerevisiae* PGK gene depends on an upstream activation sequence but does not require TATA sequences. Mol. Cell. Biol. 6,4335.

Olson L. M., Moss G. S., Baukus O., Das Gupta T. K. (1985) The role of C5 in septic lung injury. Ann. Surg. 202: 771-776.

Overduin P., Boos W., Tomassen J. (1988) Nucleotide sequence of the ugp genes of *Escherichia coli* K-12: homology to the maltose system. Mol. Microbiol. 2, 767-775.

Peterson M. G., Tanese N., Pugh B. F., Tjian R. (1990) Functional domains and upstream activation properties of cloned human TATA binding protein. Science 248, 1625.

Pines J. and Hunter T. (1990) Human cyclin A is adenovirus E1A-associated protein p60 and behaves differently from cyclin B. Nature 346, 760-763.

Powers S. (1991) RAM2, an essential gene of yeast, and RAM1 encode the two polypeptide components of the farnesyltransferase that prenylates a-factor and Ras proteins. Proc Natl Acad Sci 88:11373-11377.

Pronin, A. N., and N. Gautam (1992) Interaction between G-protein β and γ subunit types is selective. Proc. Natl. Acad. Sci. USA 89: 6220-6224.

Rarick H. M., Artemyev, N. O., and Hamm, H. E. A site on rod G protein a subunit that mediates effector activation. (1992) Science 256, 1031-1033.

Reyes M., Treptow M. A., Schuman H. A. (1986) Transport of p-nitrophenyl-maltoside by the maltose transport system of *Escherichia coli* and its subsequent hydrolysis by a cytoplasmicα-maltosidase. J. Bacteriol. 165, 918-922.

Rogers S., Wells R., Rechsteiner M. (1986) Amino acid sequences common to rapidly degraded proteins: the PEST hypothesis. Science 234, 364-368.

Russell M. and Johnson G. L. (1993) G protein N-terminal αi2/αs chimeras reveal amino acids important in regulating αs activity. Mol. Pharmacol. 44:255-263

Scharer, E. and R. Iggo (1992). "Mammalian p53 can function as a transcription factor in yeast." Nuc. Acids Res. 20 (7): 1539-1545.

Schafer W. R., Kim R., Sterne R., Thorner J., Kim S.-H., Rine J. (1989) Genetic and pharmacological suppression of oncogenic mutations in RAS genes of yeast and humans. Science 245, 379.

Schafer W. R., Trueblood C. E., Yang C.-C., Maayer M. P., Rosenberg S., Poulter C. D., Kim S.-H., Rine J. (1990) Enzymatic coupling of cholesterol intermediates to a mating pheromone precursor and to the Ras protein. Science 249, 1133.

Schena M. and Yamamoto K. R. (1988) Mammalian glucocorticoid receptor derivatives enhance transcription in yeast. Science 241, 965.

Scherr C. J. (1993) Mammalian G1 cyclins. Cell 73, 1059-1065.

Schultz R. M., Silberman S., Persky B. et al. (1988) Inhibition by human recombinant tissue inhibitor of metalloproteinases of human amnion invasion and lung colonization by murine B16-F10 melanoma cells. Cancer Res. 48, 5539.

Seideh N. G., Fournier H., Boileau G., Benjannet S. et al. (1992) The cDNA structure of the procine pro-hormone convertase PC2 and the comparative processing by PC1 and PC2 of the N-terminal glycopeptide segment of porcine POMC. FEBS Lett., 310, 235-239.

Singh A., Chen E. Y., Lugovoy J. M., Chang C. N., Hitzman R. A., Seeburg P. H. (1983) *Saccharomyces cerevisiae* contains two discrete genes coding for the α-factor pheromone. Nuc. Acids Res. 11, 4049-4063.

Slepak V. Z., Wilkie T. M., Simon, M. I. (1993) Mutational analysis of G protein α subunit Goα expressed in *Escherichia coli*. J. Biol. Chem. 268, 1414-1423.

Smeekens S. P. and Steiner D. F. (1990) Identification of a human insulinoma cDNA encoding a novel mammalian protein structurally related to the yeast dibasic processing protease Kex2. J. Biol. Chem. 265, 2997-3000.

Smith R. A., Sisk R., Lockhart P., Mathewes S. et al. (1993) Isolation of glucagon antagonists by random molecular mutagenesis and screening. Mol. Pharmacol. 43, 741-748.

Speigel A. M., Backlund P. S., Jr., Butrynski J. E., Zones T. L. J., Simonds W. F. (1991) The G protein connection: molecular basis of membrane association. TIBS 16, 338-3441.

Steube K; Chaudhuri B; Marki W; Merryweather J P; Heim J. α-factor-leader-directed secretion of recombinant human-insulin-like growth factor I from *Saccharomyces cerevisiae*. Precursor formation and processing in the yeast secretory pathway. (1991) Eur J Biochem 198, 651-657.

Strubin M. and Struhl K. (1992) Yeast and human TFIID with altered DNA-binding specificity for TATA elements. Cell 68, 721-730.

Struhl, K. (1986) Constitutive and inducible *Saccharomyces cerevisiae* promoters: Evidence for two distinctive molecular mechanisms. Mol. Cell. Biol. 6, 3847.

Struhl K. (1989) Molecular mechanisms of transcriptional regulation in yeast. Annu. Rev. Biochem.58, 1051.

Sullivan, K. A., et al (1987) Nature 330, 758-760

Takahashi, H., Hakamata Y., Watanabe Y., Kikuno R. et al. (1983) Complete nucleotide sequence of the human corticotropin-beta-lipotropin precursor gene. Nucleic Acids Research 11:6847-6858.

Thomas G., Thorne B. A., Thomas L., Allen R. G., Hruby D. E., Fuller R., Thorner J. (1988) Yeast KEX2 endopeptidase correctly cleaves a neuroendocrine prohormone in mammalian cells. Science 241, 226.

Thomas L., Cooper A., Bussey H., Thomas G. (1990) Yeast KEX1 protease cleaves a prohormone processing intermediate in mammalian cells. J. Biol. Chem. 265, 321.

Valdiva R. H., Wang L., Winans S. C. (1991) Characterization of a putative periplasmic transport system for octopine accumulation encoded by *Agrobacterium tumefaciens* T: plasmid pTi46. J. Bacteriol. 173, 6398-6405.

Vogt P. K., Bos T. J., Doolittle R. F. (1987) Homology between the DNA-binding domain of the GCN4 regulatory protein of yeast and the carboxy-terminal region of a protein coded for by the oncogene jun. Proc. Natl. Acad. Sci. 84, 3316.

Waters M. G., Evans E. A., Blobel G. (1988) Prepro-α-factor has a cleavable signal sequence. J. Biol. Chem. 263, 6209.

Webster N., Jin J. R., Green S., Hollis M., Chambon P. (1988). The yeast $UAS_G$ is a transcriptional enhancer in human HeLa cells in the presence of the GAL4 transactivator. Cell 52, 169.

Weisman H. F., Bartow T., Leppo M. K., Marsh H. C. Jr. et al. (1990) Soluble human complement receptor type 1: in vivo inhibitor of complement suppressing post-ischemic myocardial inflammation and necrosis. Science 249: 146-151.

West, J. P. et al (1985) J. Biol. Chem. 260, 14428-14430.

Whiteway M., Clark K. L, Leberer E., Degnard D., and Thomas D. Y. (1994) Genetic Identification of Residues Involved in Association of α and β G-Protein Subunits. Mol. Cell. Biol. 14:3233-3239.

Wood C. R., Boss M. A., Kenten J. H., Calvert J. E., Roberts N. A., Emtage J. S. (1985) The synthesis and in vivo assembly of functional antibodies in yeast. Nature 314, 446-449.

Xiong Y., Connolly T., Futcher B., Beach D. (1991) Human D-type cyclin. Cell 65, 691-699.

What is claimed is:

1. A method of detecting ligand binding to a heterologous G protein coupled receptor comprising:
   a) providing transformed yeast cells comprising a reporter gene under control of a pheromone-responsive promoter, a heterologous G protein-coupled receptor gene, each said gene being under the control of a separate promoter, a mutation in a SCG1/GPA1 gene, and a hybrid G.alpha. protein;
   b) combining said cells with a compound to be tested; and
   c) detecting if said compound binds to said heterologous G protein coupled receptor.

2. The method of claim 1, wherein said heterologous G protein coupled receptor is a mammalian G protein coupled receptor.

3. The method of claims 1 or 2, wherein said hybrid G.alpha. protein comprises yeast G.alpha. protein sequences and heterologous G.alpha. protein sequences.

4. The method of claims 1 or 2, wherein the reporter gene is selected from the group consisting of HIS3, G418r, URA3, LYS2, CAN1, Lacz, and CYH2 and the pheromone-responsive promoter is FUS 1.

5. The method of claim 4, wherein said reporter gene is selected from the group consisting of HIS3, G418r, URA3, LYS2, CAN1, and Lacz.

6. The method of claim 1, wherein said heterologous G protein-coupled receptor is selected from the group consisting of .beta.2 adrenergic receptor, .alpha.2 adrenergic receptor, 5HT 1-A receptor, muscarinic acetylcholine receptor, growth hormone releasing factor receptor, and somatostatin receptor.

7. The method of claim 1, wherein said heterologous G protein-coupled receptor gene encodes a receptor selected from the group consisting of .beta.2 adrenergic receptor, .alpha.2-adrenergic receptor, 5HT-1A receptor, muscarinic acetylcholine receptor, growth hormone releasing factor receptor, somatostatin receptor, cholecystokinin receptor, and adenosine receptor.

8. The method of claim 7, wherein said heterologous G protein-coupled receptor is selected from the group consisting of .beta.2 adrenergic receptor, .alpha.2 adrenergic receptor, 5HT 1-A receptor, muscarinic acetylcholine receptor, growth hormone releasing factor receptor, and somatostatin receptor.

9. The method of claims 1 or 2, wherein said transformed yeast cell further comprises a heterologous G.alpha. subunit.

10. The method of claim 9, wherein said heterologous G.alpha. subunit is selected from the group consisting of a Gs subunit, a Gi subunit, a Go subunit, a Gz subunit, a Gq subunit, a G11 subunit, and a G16 subunit.

* * * * *

UNITED STATES PATENT AND TRADEMARK OFFICE
CERTIFICATE OF CORRECTION

| | | |
|---|---|---|
| PATENT NO. | : 7,611,854 B2 | Page 1 of 1 |
| APPLICATION NO. | : 10/600003 | |
| DATED | : November 3, 2009 | |
| INVENTOR(S) | : Dana M. Fowlkes et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1642 days.

Signed and Sealed this

Nineteenth Day of October, 2010

David J. Kappos
*Director of the United States Patent and Trademark Office*

SEQUENCE LISTING (1) GENERAL INFORMATION:

(iii) NUMBER OF SEQUENCES: 119

(2) INFORMATION FOR SEQ ID NO: 1:

(i) SEQUENCE CHARACTERISTICS:
      (A) LENGTH: 89 amino acids
      (B) TYPE: amino acid (C) STRANDEDNESS: single
        (D) TOPOLOGY: linear (ii) MOLECULE TYPE: peptide (xi) SEQUENCE DESCRIPTION: SEQ ID NO: 1:

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

(2) INFORMATION FOR SEQ ID NO: 2:

(i) SEQUENCE CHARACTERISTICS:
        (A) LENGTH: 76 amino acids
        (B) TYPE: amino acid
        (D) TOPOLOGY: linear (ii) MOLECULE TYPE: peptide (xi) SEQUENCE DESCRIPTION: SEQ ID NO: 2:

Trp His Trp Leu Gln Leu Lys Pro Gly Gln Pro Met Tyr Lys Arg Glu
1               5                   10                  15

Ala Glu Ala Glu Ala Trp His Trp Leu Gln Leu Lys Pro Gly Gln Pro
            20                  25                  30

Met Tyr Lys Arg Glu Ala Asp Ala Glu Ala Trp His Trp Leu Gln Leu
        35                  40                  45

Lys Pro Gly Gln Pro Met Tyr Lys Arg Glu Ala Asp Ala Glu Ala Trp
    50                  55                  60

His Trp Leu Gln Leu Lys Pro Gly Gln Pro Met Tyr
65                  70                  75

(2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO: 3:

AAGCTTAAAA GAATG                                                15

(2) INFORMATION FOR SEQ ID NO: 4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
        (B) LOCATION: 1..24

(xi) SEQUENCE DESCRIPTION: SEQ ID NO: 4:

AAA GAA GAA GGG GTA TCT TTG CTT AAGCTCGAGA TCT                            37
Lys Glu Glu Gly Val Ser Leu Leu
 1               5

(2) INFORMATION FOR SEQ ID NO: 5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 5:

Lys Glu Glu Gly Val Ser Leu Leu
 1               5

(2) INFORMATION FOR SEQ ID NO: 6:

(i) SEQUENCE CHARACTERISTICS:
        (A) LENGTH: 77 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO: 6:

CGTGAAGCTT AAGCGTGAGG CAGAAGCTNN KNNKNNKNNK NNKNNKNNKN NKNNKNNKNN         60

KNNKNNKTGA TCATCCG                                                       77

(2) INFORMATION FOR SEQ ID NO: 7:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 7:

Lys Arg Glu Ala Glu Ala Xaa Xaa Xaa Xaa Xaa Xaa Xaa Xaa Xaa Xaa
 1               5                  10                  15

Xaa Xaa Xaa (2) INFORMATION FOR SEQ ID NO: 8:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO: 8:

Met Gln Pro Ser Thr Ala Thr Ala Ala Pro Lys Glu Lys Thr Ser Ser
 1               5                  10                  15

Glu Lys Lys Asp Asn Tyr Ile Ile Lys Gly Val Phe Trp Asp Pro Ala
                20                  25                  30

Cys Val Ile Ala
            35

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 9:

```
AAGCTTTCGA ATAGAAATG                                          19
```

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: synthetic DNA (ix) FEATURE:
        (A) NAME/KEY: CDS
        (B) LOCATION: 1..27

(xi) SEQUENCE DESCRIPTION: SEQ ID NO: 10:

```
GCC GCT CCA AAA GAA AAG ACC TCG AGC TCGCTTAAG                 36
Ala Ala Pro Lys Glu Lys Thr Ser Ser
 1               5
```

(2) INFORMATION FOR SEQ ID NO: 11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 11:

```
Ala Ala Pro Lys Glu Lys Thr Ser Ser
 1               5
```

(2) INFORMATION FOR SEQ ID NO: 12:

(i) SEQUENCE CHARACTERISTICS:
        (A) LENGTH: 79 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 12:

```
GGTACTCGAG TGAAAAGAAG GACAACNNKN NKNNKNNKNN KNNKNNKNNK NNKNNKNNKT    60

GTGTTATTGC TTAAGTACG                                                79
```

(2) INFORMATION FOR SEQ ID NO: 13:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO: 13:

```
Ser Ser Glu Lys Lys Asp Asn Xaa Xaa Xaa Xaa Xaa Xaa Xaa Xaa Xaa
1               5                  10                  15

Xaa Cys Val Ile Ala
        20

(2) INFORMATION FOR SEQ ID NO: 14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 14:

GTTAAGAACC ATATACTAGT ATCAAAAATG TCTG                                 34

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 15:

TGATCAAAAT TTACTAGTTT GAAAAGTAA TTTCG                                 35

(2) INFORMATION FOR SEQ ID NO: 16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 16:

GGCAAAATAC TAGTAAAATT TTCATGTC                                        28

(2) INFORMATION FOR SEQ ID NO: 17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 17:

GGCCCTTAAC ACACTAGTGT CGCATTATAT TTAC                                 34

(2) INFORMATION FOR SEQ ID NO: 18:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 18:
```

```
CTAAAGAAGA AGGGGTATCT TTGCTTAAGC TCGAGATCTC GACTGATAAC AACAGTGTAG        60
```

(2) INFORMATION FOR SEQ ID NO: 19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 19:

```
CATACACAAT ATAAAGCTTT AAAAGAATGA G                                      31
```

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 20:

```
GCTACTTAAG CGTGAGGCAG AAGCT                                             25
```

(2) INFORMATION FOR SEQ ID NO: 21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: synthetic DNA (ix) FEATURE:
        (D) OTHER INFORMATION: /note= The 3'-end of this sequence
            is linked to the 5'-end of SEQ ID NO:118 by (NNN)n
            where n is any chosen integer.

(xi) SEQUENCE DESCRIPTION: SEQ ID NO: 21:

```
CGGATGATCA                                                              10
```

(2) INFORMATION FOR SEQ ID NO: 22:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 22:

```
CCAAAATAAG TACAAAGCTT TCGAATAGAA ATGCAACCAT C                           41
```

(2) INFORMATION FOR SEQ ID NO: 23:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: synthetic DNA

```
        (xi) SEQUENCE DESCRIPTION: SEQ ID NO: 23:

GCCGCTCCAA AAGAAAAGAC CTCGAGCTCG CTTAAGTTCT GCGTACAAAA ACGTTGTTC        59

(2) INFORMATION FOR SEQ ID NO: 24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GGTACTCGAG TGAAAAGAAG GACAAC                                            26

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (ix) FEATURE:
        (D) OTHER INFORMATION: /note= The 3'-end of this sequence
            is linked to the 5'-end of SEQ ID NO:119 by (NNN)n
            where n is any chosen integer.

(xi) SEQUENCE DESCRIPTION: SEQ ID NO: 25:

CGTACTTAAG CAATAACACA                                                   20

(2) INFORMATION FOR SEQ ID NO: 26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 26:

CGTGAAGCTT AAGCGTGAGG CAGAAGCT                                          28

(2) INFORMATION FOR SEQ ID NO: 27:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CGGATGATCA MNNMNNMNNM NNMNNMNNMN NMNNMNNMNN MNNMNNMNNA GCTTCTG          57

(2) INFORMATION FOR SEQ ID NO: 28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA
```

(xi) SEQUENCE DESCRIPTION: SEQ ID NO: 28:

GGTACTCGAG TGAAAGAAG GACAAC                                   26

(2) INFORMATION FOR SEQ ID NO: 29:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 29:

CGTACTTAAG CAATAACACA MNNMNNMNNM NNMNNMNNMN NMNNMNNMNN MNNGTTGTCC    60

(2) INFORMATION FOR SEQ ID NO: 30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 30:

GGGAAGCTTA TGCCGAGATC GTGCTGCCAG CCGC                         34

(2) INFORMATION FOR SEQ ID NO: 31:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 31:

GGGGAAGACT TCTGCCCTGC GCCGCTGCTG CC                           32

(2) INFORMATION FOR SEQ ID NO: 32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 32:

GGGGAAGACC CGCAGGAGGC AGAAGCTTGG TTGCAG                       36

(2) INFORMATION FOR SEQ ID NO: 33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 33:

GGGAGATCTT CAGTACATTG GTTGGCC                                 27

(2) INFORMATION FOR SEQ ID NO: 34:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

```
Arg Asn Ser Ser Ser Ser Gly Ser Ser Gly Ala Gly Gln Lys Arg Glu
1               5                   10                  15

Ala Glu Ala Trp His Trp Leu Gln Leu Lys Pro Gly Gln Pro Met Tyr
            20                  25                  30
```

(2) INFORMATION FOR SEQ ID NO: 35:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 35:

CCGCGTCTCA CATGCCCAAG AAGAAGCCG                                    29

(2) INFORMATION FOR SEQ ID NO: 36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 36:

CCGTCTAGAT GCTGGCAGCG TGGG                                          24

(2) INFORMATION FOR SEQ ID NO: 37:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

TTAAGCGTGA GGCAGAAGCT TATCGATA                                    28

(2) INFORMATION FOR SEQ ID NO: 38:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

CGCACTCCGT CTTCGAATAG CTATCTAG                                    28

(2) INFORMATION FOR SEQ ID NO: 39:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

```
CTGGATGCGA AGACAGCTNN KNNKNNKNNK NNKNNKNNKN NKNNKNNKNN KNNKTGATCA      60

GTCTGTGACG C                                                          71
```

(2) INFORMATION FOR SEQ ID NO: 40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

```
GCGTCACAGA CTGATCA                                                    17
```

(2) INFORMATION FOR SEQ ID NO: 41:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

```
GCCGTCAGTA AAGCTTGGCA TTGGTTGCAG CCTATGTACT GATCAGTCTG TGACGC          56
```

(2) INFORMATION FOR SEQ ID NO: 42:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 42:

```
TGG CAT TGG TTG CAG CTA AAA CCT GGC CAA CCA ATG TAC                   39
Trp His Trp Leu Gln Leu Lys Pro Gly Gln Pro Met Tyr
 1               5                  10
```

(2) INFORMATION FOR SEQ ID NO: 43:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 43:

Trp His Trp Leu Gln Leu Lys Pro Gly Gln Pro Met Tyr
  1               5                  10

(2) INFORMATION FOR SEQ ID NO: 44:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 44:

CTGGATGCGA AGACTCAGCT                                               20

(2) INFORMATION FOR SEQ ID NO: 45:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 45:

CGGATGATCA GTACATTGGT TGGCCAGGTT TTAGCTGCAA CCAATGCCAA GCTGAGTCTT   60

CGCATCCAG                                                          69

(2) INFORMATION FOR SEQ ID NO: 46:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..39

(xi) SEQUENCE DESCRIPTION: SEQ ID NO: 46:

TGG CAT TGG CTA CAG CTA ACG CCT GGG CAA CCA ATG TAC                 39
Trp His Trp Leu Gln Leu Thr Pro Gly Gln Pro Met Tyr
  15              20                  25

(2) INFORMATION FOR SEQ ID NO: 47:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (xi) SEQUENCE DESCRIPTION: SEQ ID NO: 47:

Trp His Trp Leu Gln Leu Thr Pro Gly Gln Pro Met Tyr
  1               5                  10

(2) INFORMATION FOR SEQ ID NO: 48:

(i) SEQUENCE CHARACTERISTICS:
         (A) LENGTH: 39 base pairs
         (B) TYPE: nucleic acid

```
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 48:

TGG CAT TGG CTG GAG CTT ATG CCT GGC CAA CCA TTA TAC            39
Trp His Trp Leu Glu Leu Met Pro Gly Gln Pro Leu Tyr
    15                  20                  25

(2) INFORMATION FOR SEQ ID NO: 49:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 49:

Trp His Trp Leu Glu Leu Met Pro Gly Gln Pro Leu Tyr
 1               5                  10

(2) INFORMATION FOR SEQ ID NO: 50:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 50:

TGG CAT TGG ATG GAG CTA AGA CCT GGC CAA CCA ATG TAC            39
Trp His Trp Met Glu Leu Arg Pro Gly Gln Pro Met Tyr
    15                  20                  25

(2) INFORMATION FOR SEQ ID NO: 51:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 51:

Trp His Trp Met Glu Leu Arg Pro Gly Gln Pro Met Tyr
 1               5                  10

(2) INFORMATION FOR SEQ ID NO: 52:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

(B) LOCATION: 1..33

(xi) SEQUENCE DESCRIPTION: SEQ ID NO: 52:

TAT GCT CTG TTT GTT CAT TTT TTT GAT ATT CCG                33
Tyr Ala Leu Phe Val His Phe Phe Asp Ile Pro
    15                  20

(2) INFORMATION FOR SEQ ID NO: 53:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 53:

Tyr Ala Leu Phe Val His Phe Phe Asp Ile Pro
 1               5                  10

(2) INFORMATION FOR SEQ ID NO: 54:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..33

(xi) SEQUENCE DESCRIPTION: SEQ ID NO: 54:

TTT AAG GGT CAG GTG CGT TTT GTG GTT CTT GCT                33
Phe Lys Gly Gln Val Arg Phe Val Val Leu Ala
    15                  20

(2) INFORMATION FOR SEQ ID NO: 55:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 55:

Phe Lys Gly Gln Val Arg Phe Val Val Leu Ala
 1               5                  10

(2) INFORMATION FOR SEQ ID NO: 56:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..33

(xi) SEQUENCE DESCRIPTION: SEQ ID NO: 56:

CTT ATG TCT CCG TCT TTT TTT TTG CCT GCG                    33
Leu Met Ser Pro Ser Phe Phe Phe Leu Pro Ala
    15                  20

(2) INFORMATION FOR SEQ ID NO: 57:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 57:

Leu Met Ser Pro Ser Phe Phe Phe Leu Pro Ala
 1               5                  10

(2) INFORMATION FOR SEQ ID NO: 58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 58:

CGGGATCCGA TGCAATTTTC AACATGC                                27

(2) INFORMATION FOR SEQ ID NO: 59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 59:

GCTCTAGATG CTACTGATCC CGC                                    23

(2) INFORMATION FOR SEQ ID NO: 60:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 60:

CGCCGCATGA CTCCATTG                                          18

(2) INFORMATION FOR SEQ ID NO: 61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 61:

GGGGTACCAA TAGGTTCTTT CTTAGG                                 26

(2) INFORMATION FOR SEQ ID NO: 62:

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

GGTGGGAGGG TGCTCTCTAG AAGGAAGTGT TCACC                            35

(2) INFORMATION FOR SEQ ID NO: 63:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 63:

GCCCAGGAGA CCAGACCATG GACTCCTTCA ATTATACCAC C                     41

(2) INFORMATION FOR SEQ ID NO: 64:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 64:

CCCCTTAAGC GTGAGGCAGA AGCTACTCTG CAAAAGAAGA TC                    42

(2) INFORMATION FOR SEQ ID NO: 65:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 65:

GAAGATCTTC AGCGGCCGAG TTGCATGTC                                   29

(2) INFORMATION FOR SEQ ID NO: 66:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 66:

GATATATTAA GGTAGGAAAC CATGGGGTGT ACAGTGAG                         38

(2) INFORMATION FOR SEQ ID NO: 67:

(i) SEQUENCE CHARACTERISTICS:
        (A) LENGTH: 34 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO: 67:

CGAGCGCTCG AGGGAACGTA TAATTAAAGT AGTG                              34

(2) INFORMATION FOR SEQ ID NO: 68:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 68:

GCGCGGTACC AAGCTTCAAT TCGAGATAAT ACCC                              34

(2) INFORMATION FOR SEQ ID NO: 69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 69:

CCCGAATCCA CCAATTTCTT TACG                                        24

(2) INFORMATION FOR SEQ ID NO: 70:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 70:

GCGGCGTCGA CGCGGCCGCG TAACAGT                                     27

(2) INFORMATION FOR SEQ ID NO: 71:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 71:

CTGCTGGAGC TCCGCCTGCT GCTGCTGGGT GCTGGAG                          37

(2) INFORMATION FOR SEQ ID NO: 72:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA -continued (xi) SEQUENCE DESCRIPTION: SEQ ID NO: 72:

CTGCTGGTCG ACGCGGCCGC GGGGGTTCCT TCTTAGAAGC AGC                43

(2) INFORMATION FOR SEQ ID NO: 73:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 73:

GGGCTCGAGC CTTCTTAGAG CAGCTCGTAC                               30

(2) INFORMATION FOR SEQ ID NO: 74:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 74:

CTGCTGGAGC TCAAGTTGCT GCTGTTGGGT GCTGGGG                       37

(2) INFORMATION FOR SEQ ID NO: 75:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 75:

CTGCTGGTCG ACGCGGCCGC GCCCCTCAGA AGAGGCCGCG GTCC               44

(2) INFORMATION FOR SEQ ID NO: 76:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 76:

GGGCTCGAGC CTCAGAAGAG GCCGCAGTC                                29

(2) INFORMATION FOR SEQ ID NO: 77:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 77:

CTGCTGGAGC TCAAGCTGCT GCTACTCGGT GCTGGAG                       37

(2) INFORMATION FOR SEQ ID NO: 78:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 78:

```
CTGCTGGTCG ACGCGGCCGC CACTAACATC CATGCTTCTC AATAAAGTC                49
```

(2) INFORMATION FOR SEQ ID NO: 79:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 79:

```
GGGCTCGAGC ATGCTTCTCA ATAAAGTCCA C                                   31
```

(2) INFORMATION FOR SEQ ID NO: 80:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 80:

```
GCATCCATCA ATAATCCAG                                                 19
```

(2) INFORMATION FOR SEQ ID NO: 81:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 81:

```
GAAACAATGG ATCCACTTCT TAC                                            23
```

(2) INFORMATION FOR SEQ ID NO: 82:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

```
Met Gly Cys Thr Val Ser Thr Gln Thr Ile Gly Asp Glu Ser Asp Pro
1               5                   10                  15

Phe Leu Gln Asn Lys Arg Ala Asn Asp Val Ile Glu Gln Ser Leu Gln
            20                  25                  30
```

-continued

```
Leu Glu Lys Gln Arg Asp Lys Asn Glu Ile Lys Leu Leu Leu Leu Gly
        35                  40                  45

Ala Gly Glu Ser Gly Lys Ser Thr Val Leu Lys Gln Leu Lys Leu Leu
    50                  55                  60

His Gln
65
```

(2) INFORMATION FOR SEQ ID NO: 83:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

```
Met Gly Cys Leu Gly Thr Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val
65
```

(2) INFORMATION FOR SEQ ID NO: 84:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 84:

```
Met Gly Cys Thr Val Ser Ala Glu Asp Lys Ala Ala Ala Glu Arg Ser
1               5                   10                  15

Lys Met Ile Asp Lys Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu
    50                  55
```

(2) INFORMATION FOR SEQ ID NO: 85:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

```
Met Gly Cys Thr Val Ser Ala Glu Asp Lys Ala Ala Val Glu Arg Ser
1               5                   10                  15

Lys Met Ile Asp Arg Asn Leu Arg Glu Asp Gly Glu Lys Ala Ala Lys
```

```
                   20                  25                  30
Glu Val Lys Leu Leu Leu Gly Ala Gly Glu Ser Gly Lys Ser Thr
               35                  40                  45

Ile Val Lys Gln Met Lys Ile Ile His Glu
               50                  55

(2) INFORMATION FOR SEQ ID NO: 86:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Met Ala Arg Ser Leu Thr Trp Arg Cys Cys Pro Trp Cys Leu Thr Glu
1               5                  10                  15

Asp Glu Lys Ala Ala Ala Arg Val Asp Gln Glu Ile Asn Arg Ile Leu
               20                  25                  30

Leu Glu Gln Lys Lys Gln Asp Arg Gly Glu Leu Lys Leu Leu Leu Leu
               35                  40                  45

Gly Pro Gly Glu Ser Gly Lys Ser Thr Phe Ile Lys Gln Met Arg Ile
               50                  55                  60

Ile His Gly
65

(2) INFORMATION FOR SEQ ID NO: 87:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Met Gly Cys Thr Val Ser Thr Gln Thr Ile Gly Asp Glu Ser Asp Pro
1               5                  10                  15

Phe Leu Gln Asn Lys Arg Ala Asn Asp Val Ile Glu Gln Ser Leu Gln
               20                  25                  30

Leu Glu Lys Gln Arg Asp Lys Asn Glu Arg Lys Leu Leu Leu Leu Gly
               35                  40                  45

Ala Gly Glu Ser Gly Lys Ser Thr Ile Val Lys Gln Met Arg Ile Leu
               50                  55                  60

His Val
65

(2) INFORMATION FOR SEQ ID NO: 88:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Met Gly Cys Thr Val Ser Thr Gln Thr Ile Gly Asp Glu Ser Asp Pro
1               5                  10                  15
```

Phe Leu Gln Asn Lys Arg Ala Asn Asp Val Ile Glu Gln Ser Leu Gln
            20                  25                  30

Leu Glu Lys Gln Arg Asp Lys Asn Glu Val Lys Leu Leu Leu Leu Gly
            35                  40                  45

Ala Gly Glu Ser Gly Lys Ser Thr Ile Val Lys Gln Met Lys Ile Ile
        50                  55                  60

His Glu
65

(2) INFORMATION FOR SEQ ID NO: 89:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Met Gly Cys Thr Val Ser Thr Gln Thr Ile Gly Asp Glu Ser Asp Pro
1               5                   10                  15

Phe Leu Gln Asn Lys Arg Ala Asn Asp Val Ile Glu Gln Ser Leu Gln
            20                  25                  30

Leu Glu Lys Gln Arg Asp Lys Asn Glu Val Lys Leu Leu Leu Leu Gly
            35                  40                  45

Ala Gly Glu Ser Gly Lys Ser Thr Ile Val Lys Gln Met Lys Ile Ile
        50                  55                  60

His Glu
65

(2) INFORMATION FOR SEQ ID NO: 90:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

Met Gly Cys Thr Val Ser Thr Gln Thr Ile Gly Asp Glu Ser Asp Pro
1               5                   10                  15

Phe Leu Gln Asn Lys Arg Ala Asn Asp Val Ile Glu Gln Ser Leu Gln
            20                  25                  30

Leu Glu Lys Gln Arg Asp Lys Asn Glu Leu Lys Leu Leu Leu Leu Gly
            35                  40                  45

Pro Gly Glu Ser Gly Lys Ser Thr Phe Ile Lys Gln Met Arg Ile Ile
        50                  55                  60

His Gly
65

(2) INFORMATION FOR SEQ ID NO: 91:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
              (A) NAME/KEY: CDS
              (B) LOCATION: 1..39

(xi) SEQUENCE DESCRIPTION: SEQ ID NO: 91:

TGG CAT TGG TTG CAG CTA AAA CCT GGC CAG CCT ATG TAC            39
Trp His Trp Leu Gln Leu Lys Pro Gly Gln Pro Met Tyr
             15                  20

(2) INFORMATION FOR SEQ ID NO: 92:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (xi) SEQUENCE DESCRIPTION: SEQ ID NO: 92:

Trp His Trp Leu Gln Leu Lys Pro Gly Gln Pro Met Tyr
 1               5                  10

(2) INFORMATION FOR SEQ ID NO: 93:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..39

(xi) SEQUENCE DESCRIPTION: SEQ ID NO: 93:

TGG CAT TGG TTG TCC TTG TCG CCC GGG CAG CCT ATG TAC            39
Trp His Trp Leu Ser Leu Ser Pro Gly Gln Pro Met Tyr
             15                  20                  25

(2) INFORMATION FOR SEQ ID NO: 94:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (xi) SEQUENCE DESCRIPTION: SEQ ID NO: 94:

Trp His Trp Leu Ser Leu Ser Pro Gly Gln Pro Met Tyr
 1               5                  10

(2) INFORMATION FOR SEQ ID NO: 95:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..39

(xi) SEQUENCE DESCRIPTION: SEQ ID NO: 95:

```
TGG CAT TGG TTG TCC CTG GAC GCT GGC CAG CCT ATG TAC         39
Trp His Trp Leu Ser Leu Asp Ala Gly Gln Pro Met Tyr
    15                  20                  25
```

(2) INFORMATION FOR SEQ ID NO: 96:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 96:

```
Trp His Trp Leu Ser Leu Asp Ala Gly Gln Pro Met Tyr
 1               5                  10
```

(2) INFORMATION FOR SEQ ID NO: 97:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..39

(xi) SEQUENCE DESCRIPTION: SEQ ID NO: 97:

```
TGG CAT TGG TTG ACC TTG ATG GCC GGG CAG CCT ATG TAC         39
Trp His Trp Leu Thr Leu Met Ala Gly Gln Pro Met Tyr
    15                  20                  25
```

(2) INFORMATION FOR SEQ ID NO: 98:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 98:

```
Trp His Trp Leu Thr Leu Met Ala Gly Gln Pro Met Tyr
 1               5                  10
```

(2) INFORMATION FOR SEQ ID NO: 99:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..39

(xi) SEQUENCE DESCRIPTION: SEQ ID NO: 99:

```
TGG CAT TGG TTG CAG CTG TCG GCG GGC CAG CCT ATG TAC         39
Trp His Trp Leu Gln Leu Ser Ala Gly Gln Pro Met Tyr
    15                  20                  25
```

(2) INFORMATION FOR SEQ ID NO: 100:

```
    (i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 100:

Trp His Trp Leu Gln Leu Ser Ala Gly Gln Pro Met Tyr
 1               5                  10

(2) INFORMATION FOR SEQ ID NO: 101:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..39

(xi) SEQUENCE DESCRIPTION: SEQ ID NO: 101:

TGG CAT TGG TTG AGG TTG CAG TCC GGC CAG CCT ATG TAC        39
Trp His Trp Leu Arg Leu Gln Ser Gly Gln Pro Met Tyr
 15              20                 25

(2) INFORMATION FOR SEQ ID NO: 102:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 102:

Trp His Trp Leu Arg Leu Gln Ser Gly Gln Pro Met Tyr
 1               5                  10

(2) INFORMATION FOR SEQ ID NO: 103:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..39

(xi) SEQUENCE DESCRIPTION: SEQ ID NO: 103:

TGG CAT TGG TTG CGC TTG TCC GCC GGG CAG CCT ATG TAC        39
Trp His Trp Leu Arg Leu Ser Ala Gly Gln Pro Met Tyr
 15              20                 25

(2) INFORMATION FOR SEQ ID NO: 104:

(i) SEQUENCE CHARACTERISTICS:
        (A) LENGTH: 13 amino acids
        (B) TYPE: amino acid
        (D) TOPOLOGY: linear (ii) MOLECULE TYPE: peptide
```

(xi) SEQUENCE DESCRIPTION: SEQ ID NO: 104:

Trp His Trp Leu Arg Leu Ser Ala Gly Gln Pro Met Tyr
  1               5                  10

(2) INFORMATION FOR SEQ ID NO: 105:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 105:

TGG CAT TGG TTG TCG CTC GTC CCG GGG CAG CCT ATG TAC      39
Trp His Trp Leu Ser Leu Val Pro Gly Gln Pro Met Tyr
 15              20                  25

(2) INFORMATION FOR SEQ ID NO: 106:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 106:

Trp His Trp Leu Ser Leu Val Pro Gly Gln Pro Met Tyr
  1               5                  10

(2) INFORMATION FOR SEQ ID NO: 107:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 107:

TGG CAT TGG TTG TCC CTG TAC CCC GGG CAG CCT ATG TAC      39
Trp His Trp Leu Ser Leu Tyr Pro Gly Gln Pro Met Tyr
 15              20                  25

(2) INFORMATION FOR SEQ ID NO: 108:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 108:

Trp His Trp Leu Ser Leu Tyr Pro Gly Gln Pro Met Tyr
  1               5                  10

(2) INFORMATION FOR SEQ ID NO: 109:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 109:

```
TGG CAT TGG TTG CGG CTG CAG CCC GGG CAG CCT ATG TAC                    39
Trp His Trp Leu Arg Leu Gln Pro Gly Gln Pro Met Tyr
    15                  20                  25
```

(2) INFORMATION FOR SEQ ID NO: 110:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 110:

```
Trp His Trp Leu Arg Leu Gln Pro Gly Gln Pro Met Tyr
 1               5                  10
```

(2) INFORMATION FOR SEQ ID NO: 111:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

```
Arg Ile Asp Thr Thr Gly Ile Thr Glu Thr Glu Phe Asn Ile Gly Ser
 1               5                  10                  15

Ser Lys Phe Lys Val Leu Asp Ala Gly Gly Gln Arg Ser Glu Arg Lys
                20                  25                  30

Lys Trp Ile His Cys Phe Glu Gly Ile Thr Ala Val Leu Phe Val Leu
                35                  40                  45

Ala Met Ser Glu Tyr Asp Gln Met Leu Phe Glu Asp Glu Arg
                50                  55                  60
```

(2) INFORMATION FOR SEQ ID NO: 112:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

```
Arg Val Leu Thr Ser Gly Ile Phe Glu Thr Lys Phe Gln Asn Asp Lys
 1               5                  10                  15

Val Asn Phe His Met Phe Asp Val Gly Gly Gln Arg Asp Glu Arg Lys
                20                  25                  30

Lys Trp Ile Gln Cys Phe Asn Asp Val Thr Ala Ile Ile Phe Val Val
```

```
                      35                  40                  45
Ala Ser Ser Ser Tyr Asn Met Val Ile Arg Glu Asp Asn Gln
 50                  55                  60

(2) INFORMATION FOR SEQ ID NO: 113:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

Arg Val Lys Thr Thr Gly Ile Val Glu Thr His Phe Thr Phe Lys Asp
 1               5                  10                  15

Leu His Phe Lys Met Phe Asp Val Gly Gly Gln Arg Ser Glu Arg Lys
                20                  25                  30

Lys Trp Ile His Cys Phe Glu Gly Val Thr Ala Ile Ile Phe Cys Val
                35                  40                  45

Ala Leu Ser Ala Tyr Asp Leu Val Leu Ala Asp Glu Glu Met
 50                  55                  60

(2) INFORMATION FOR SEQ ID NO: 114:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

Arg Val Lys Thr Thr Gly Ile Val Glu Thr His Phe Thr Phe Lys Asp
 1               5                  10                  15

Leu Tyr Phe Lys Met Phe Asp Val Gly Gly Gln Arg Ser Glu Arg Lys
                20                  25                  30

Lys Trp Ile His Cys Phe Glu Gly Val Thr Ala Ile Ile Phe Cys Val
                35                  40                  45

Ala Leu Ser Asp Tyr Asp Leu Val Leu Ala Glu Asp Glu Glu
 50                  55                  60

(2) INFORMATION FOR SEQ ID NO: 115:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 115:

Arg Val Lys Thr Thr Gly Ile Val Glu Thr His Phe Thr Phe Lys Asn
 1               5                  10                  15

Leu His Phe Arg Leu Phe Asp Val Gly Gly Gln Arg Ser Glu Arg Lys
                20                  25                  30

Lys Trp Ile His Cys Phe Glu Asp Val Thr Ala Ile Ile Phe Cys Asn
                35                  40                  45

Ala Leu Ser Gly Tyr Asp Gln Val Leu His Glu Asp Glu Thr
 50                  55                  60
```

(2) INFORMATION FOR SEQ ID NO: 116:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 116:

```
Arg Val Pro Thr Thr Gly Ile Ile Glu Tyr Pro Phe Asp Leu Glu Asn
 1               5                  10                  15

Ile Ile Phe Lys Met Val Asp Ala Gly Gly Gln Arg Ser Glu Arg Lys
                20                  25                  30

Lys Trp Ile His Cys Phe Glu Asn Val Thr Ser Ile Met Phe Leu Val
                35                  40                  45

Ala Leu Ser Glu Tyr Asp Gln Cys Leu Glu Glu Asn Asn Gln
            50                  55                  60
```

(2) INFORMATION FOR SEQ ID NO: 117:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

```
Arg Met Pro Thr Thr Gly Ile Asn Glu Tyr Cys Phe Ser Val Gln Lys
 1               5                  10                  15

Thr Asn Leu Lys Ile Val Asp Ala Gly Gly Gln Arg Ser Glu Arg Lys
                20                  25                  30

Lys Trp Ile His Cys Phe Glu Asn Ile Ile Ala Leu Ile Tyr Leu Ala
                35                  40                  45

Ser Leu Ser Glu Tyr Asp Gln Val Leu Val Glu Ser Asp Asn
            50                  55                  60
```

(2) INFORMATION FOR SEQ ID NO: 118:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (ix) FEATURE:
        (D) OTHER INFORMATION: /note= The 5'-end of this sequence
            is linked to the 3'-end of SEQ ID NO:21 by (NNN)n
            where n is any chosen integer.

(xi) SEQUENCE DESCRIPTION: SEQ ID NO: 118:

AGCTTCTGCC TCACGCTTAA GTAGC                                          25

(2) INFORMATION FOR SEQ ID NO: 119:

(i) SEQUENCE CHARACTERISTICS:
        (A) LENGTH: 26 base pairs
        (B) TYPE: nucleic acid
        (C) STRANDEDNESS: single
        (D) TOPOLOGY: linear

```
          (ii) MOLECULE TYPE: synthetic DNA (ix) FEATURE:
               (D) OTHER INFORMATION: /note= The 5'-end of this sequence
                   is linked to the 3'-end of SEQ ID NO:25 by (NNN)n
                   where n is any chosen integer.

(xi) SEQUENCE DESCRIPTION: SEQ ID NO: 119:

GTTGTCCTTC TTTTCACTCG AGTACC                                              26
```